US011788088B2

(12) United States Patent
Clarke et al.

(10) Patent No.: US 11,788,088 B2
(45) Date of Patent: Oct. 17, 2023

(54) CRISPR/CAS SYSTEM AND METHOD FOR GENOME EDITING AND MODULATING TRANSCRIPTION

(71) Applicant: THE BOARD OF TRUSTEES OF THE UNIVERSITY OF ILLINOIS, Urbana, IL (US)

(72) Inventors: Ryan E. Clarke, Chicago, IL (US); Bradley J. Merrill, Chicago, IL (US); Matthew S. MacDougall, Chicago, IL (US); Hannah M. Pennington, Chicago, IL (US); Brian R. Shy, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 608 days.

(21) Appl. No.: 16/650,496

(22) PCT Filed: Sep. 21, 2018

(86) PCT No.: PCT/US2018/052211
§ 371 (c)(1),
(2) Date: Mar. 25, 2020

(87) PCT Pub. No.: WO2019/067322
PCT Pub. Date: Apr. 4, 2019

(65) Prior Publication Data
US 2020/0308581 A1    Oct. 1, 2020

Related U.S. Application Data

(60) Provisional application No. 62/563,128, filed on Sep. 26, 2017, provisional application No. 62/563,131, filed on Sep. 26, 2017, provisional application No. 62/563,133, filed on Sep. 26, 2017.

(51) Int. Cl.
*C12N 15/113*    (2010.01)
*C12N 9/22*    (2006.01)

(52) U.S. Cl.
CPC .............. *C12N 15/113* (2013.01); *C12N 9/22* (2013.01); *C12Y 603/02019* (2013.01); *C07K 2319/06* (2013.01); *C07K 2319/80* (2013.01); *C07K 2319/95* (2013.01); *C12N 2310/121* (2013.01); *C12N 2310/122* (2013.01); *C12N 2310/123* (2013.01); *C12N 2310/20* (2017.05)

(58) Field of Classification Search
CPC .............................. C12N 9/22; C12N 2310/20
See application file for complete search history.

(56) References Cited

U.S. PATENT DOCUMENTS

| | | | |
|---|---|---|---|
| 2005/0257277 A1* | 11/2005 | Lu ........................ | C12N 15/111 435/456 |
| 2015/0232881 A1* | 8/2015 | Glucksmann ......... | C12N 15/111 435/468 |
| 2016/0298096 A1 | 10/2016 | Charpentier et al. | |
| 2016/0376610 A1 | 12/2016 | Davis et al. | |
| 2017/0166875 A1* | 6/2017 | Maizels ............... | C12Y 301/00 |
| 2019/0119678 A1* | 4/2019 | Grimm ................ | C12N 15/113 |
| 2019/0233806 A1* | 8/2019 | Garreau de Loubresse ............... C12N 15/113 |
| 2019/0314521 A1* | 10/2019 | Jaskula-Ranga ..... | A61K 48/005 |
| 2019/0352634 A1* | 11/2019 | Fulga .................... | C12N 15/63 |

FOREIGN PATENT DOCUMENTS

| | | | |
|---|---|---|---|
| CN | 104531632 A | 4/2015 | |
| CN | 105647885 B | 8/2017 | |
| WO | 2012024625 A2 | 2/2012 | |
| WO | 2015/035139 | 3/2015 | |
| WO | 2015/153940 | 10/2015 | |
| WO | 2015/168404 | 11/2015 | |
| WO | 2016106244 A1 | 6/2016 | |
| WO | 2016210271 A1 | 12/2016 | |
| WO | WO-2016196539 A2 * | 12/2016 | ............. A61K 38/46 |
| WO | WO-2016196655 A1 * | 12/2016 | ........... C12N 15/102 |
| WO | 2017/024047 | 2/2017 | |
| WO | 2017024047 A1 | 2/2017 | |
| WO | 2017106616 A1 | 6/2017 | |
| WO | 2017/158153 | 9/2017 | |
| WO | 2017160752 A1 | 9/2017 | |
| WO | 2018/231730 | 12/2018 | |

OTHER PUBLICATIONS

Cong et al. (Science vol. 339, pp. 819-823) (Year: 2013).*
Oesinghaus et al. Nature Communications 10:2092, pp. 1-11 (Year: 2019).*
Wasch et al. Oncogene 29, 1-10 (Year: 2010).*
Supplemental Search Report and Search Opinion dated Sep. 16, 2021 in EP18862655.0.
Gao et al. "Self-Processing of Ribozyme-flanked RNAs into Guide RNAs in vitro and in vivo for CRISPR-mediated Genome Editing" J. Int. Plant Bio. 2016 56(4): 343-349.
Ferry et al., "Rational Design of Inducible CRISPR Guide RNAs for de nono Assembly of Transciprtional Programs" Nature Comm. 2017 vol. 8:14633.
Supplementary European Search Report dated May 28, 2021 for EP 18862655.0, filed Sep. 21, 2018.
Gutschner, T., M. Haemmerle, G. Genovese, G.F. Draetta and L. Chin (2016) "Post-translational Regulation of Cas9 during G1 Enhances Homology-Directed Repair," Cell Rep. 14(6):1555-1566.

(Continued)

*Primary Examiner* — Brian Whiteman
(74) *Attorney, Agent, or Firm* — LICATA & TYRRELL P.C.

(57) ABSTRACT

A CRISPR/Cas system and method for editing or regulating transcription of a genome of a cell are provided, wherein the system includes a Cas endonuclease fused with one or more degron sequences and at least one activatable cognate single guide RNA harboring an inactivation sequence in a non-essential region of the cognate sgRNA, wherein said inactivation sequence comprises one or more endonuclease recognition sites of, e.g., a ribozyme.

8 Claims, 15 Drawing Sheets
Specification includes a Sequence Listing.

(56) References Cited

OTHER PUBLICATIONS

Howden, S.E., B. McColl, A. Glaser, J. Vadolas, S. Petrou, M.H. Little, A.G. Elefanty and E.G. Stanley (2016) "A Cas9 Variant for Efficient Generation of Indel-Free Knockin or Gene-Corrected Human Pluripotent Stem Cells," Stem Cell Rep. 7(3):508-517.

Maji, B., C.L. Moore, B. Zetsche, S.E. Volz, F. Zhang, M.D. Shoulders and A. Choudhary (2017) "Multidimensional chemical control of CRISPR-Cas9," Nat. Chem. Biol. 13(1):9-11.

Nissim, L., S.D. Perli, A. Fridkin, P. Perez-Pinera and T.K. Lu (2014) "Multiplexed and programmable regulation of gene networks with an integrated RNA and CRISPR/Cas toolkit in human cells," Mol. Cell. 54(4):698-710.

Senturk, S., N.H. Shirole, D.G. Nowak, V. Corbo, D. Pal, A. Vaughan, D.A. Tuveson, L.C. Trotman, J.B. Kinney and R. Sordella (2017) "Rapid and tunable method to temporally control gene editing based on conditional Cas9 stabilization," Nat. Commun. 8:14370.

Tsai, S.Q., N. Wyvekens, C. Khayter, J.A. Foden, V. Thapar, D. Reyon, M.J. Goodwin, M.J. Aryee and J.K. Joung (2014) "Dimeric CRISPR RNA-guided FokI nucleases for highly specific genome editing," Nat. Biotechnol. 32(6):569-576.

Xu, L., L. Zhao, Y. Gao, J. Xu and R. Han (2017) "Empower multiplex cell and tissue-specific CRISPR-mediated gene manipulation with self-cleaving ribozymes and tRNA," Nucl. Acids Res. 45(5):e28.

International Search Report and Written Opinion in PCT/US2018/052211 dated Jan. 28, 2019.

International Preliminary Report on Patentability in PCT/US2018/052211 dated Apr. 9, 2020.

* cited by examiner

ANALYSIS OF GENETIC BARCODE AND CELLULAR ACTIVITIES

1  #4  #9  #13  #17

CELLS EXPOSED TO LIGAND INITIATE A DESIGNED GENETIC PROGRAM

GENE 1
GENE 2
GENE 3

BIOPROCESSOR IMPLEMENTATION WITHIN A SINGLE CELL

PROGRAM 1
PROGRAM 2
PROGRAM 3
PROGRAM 4

CRISPR/CAS SYSTEM AND METHOD FOR GENOME EDITING AND MODULATING TRANSCRIPTION

INTRODUCTION

This application is the national phase under 35 U.S.C. § 371 of PCT International Application No. PCT/US2018/052211, filed Sep. 21, 2018, which claims the benefit of priority of U.S. Provisional Application Nos. 62/563,128, filed Sep. 26, 2017; 62/563,131, filed Sep. 26, 2017; and 62/563,133, filed Sep. 26, 2017, the contents of which are incorporated herein by reference in their entireties.

This invention was made with government support under Grant Number RO1 HD081534 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled "UIC0076USNPSeqList ST25," 120,911 bytes in size, generated May 13, 2023, and filed via EFS-Web, is provided in lieu of a paper copy. This Sequence Listing is hereby incorporated by reference into the specification.

BACKGROUND INFORMATION

In early studies with mammalian cells, the introduction of a DNA double-strand break (DSB) at a unique position in the genome using the homing endonuclease I-SceI was found to stimulate gene targeting by homologous recombination. Subsequently, artificial sequence-specific nucleases, such as zinc finger and TALE nucleases, and more recently RNA-guided Clustered Regularly Interspersed Short Palindromic Repeats (CRISPR)/CRISPR-associated (Cas) (CRISPR/Cas) nucleases have been used to target predetermined genomic sites. With CRISPR/Cas9, a single guide RNA (sgRNA or gRNA) with a spacer sequence complementary to the target DNA directs DNA cleavage by the Cas9 endonuclease. Modification of the genome sequence takes place during DSB repair, and the molecular pathways that come into play determine the type of sequence change. Canonical nonhomologous end-joining (NHEJ) and alternative end-joining pathways such as microhomology-mediated end-joining (MMEJ) proceed by ligation of DNA ends after they have been processed and result in targeted but imprecise indels (generally small insertions or deletions), Microhomologies of two or more nucleotides may be exposed after DNA cleavage through resection and may be used during repair by MMEJ. In contrast to end-joining pathways, homology-dependent repair (HDR) using an exogenous DNA repair template supports precise genome editing. Typically, a transgene with arms homologous to sequences flanking the DSB can be used and the transgene will thus be precisely integrated.

Among the barriers limiting efficiency of CRISPR/Cas9-based genome editing is the presence of non-coding regions or weakly-transcribed genes, which appear to be refractory to CRISPR/Cas9 mutagenesis, and the low frequency of HDR relative to NHEJ repair, which makes it difficult to generate precise changes to genomic sequences. In order to enhance genome editing by HDR, different strategies have been developed. For example, when cells are synchronized in S/G2 phases, the cell-cycle phases to which DNA repair by homologous recombination are restricted, and HDR can be increased up to five-fold. NHEJ inhibition, for instance, following Ligase 4 inactivation, can also increase HDR. Another approach has been to fuse a canonical Cdh1 or Cdc20 degron such as the Geminin degron to Cas9 in order to induce its degradation in G1 and restrict target DNA cleavage to S/G2 phases (Gutschner, et al. (2016) Cell Rep. 14:1555-1566; Maji, et al. (2017) Nat. Chem. Biol. 13:9-11; Howden, et al. (2016) Stem Cell Rep. 7:508-517). See also WO 2017/024047 A1, US 2016/0376610, and CN 105647885 B. Similarly, the PEST degron has been fused to Cas9 to shorten the half-life of Cas9 (CN 201410656081).

Another limitation of the current CRISPR method is the constitutive endonuclease activity when Cas9 and its sgRNA are co-expressed. This can be particularly problematic when targeting genes that are developmentally important or essential for viability. Furthermore, it has been shown that constitutive expression of Cas9 can increase the number of off-target mutations and can trigger a DNA damage response. One approach to address this has been the fusion of a FKBP12-derived destabilizing domain to Cas9, which conditionally regulates protein stability (Senturk, eta 1. (2017) Nat. Commun. 8:14370; US 2016/0298096).

When multiple sgRNAs are expressed, the Cas9 can be guided to simultaneously manipulate multiple genomic loci, which can be achieved by co-transfection of multiple sgRNAs in separate constructs. Although this approach is highly effective, it would be a challenge for certain applications where the vector capacity and/or vector numbers are limited for simultaneous production of multiple gRNAs. Several strategies have been developed to express multiple gRNAs from a single transcript. One is to use Csy4 endoribonuclease, which can process a transcript containing gRNAs fused with Csy4-cleavable RNA (Nissim, et al. (2014) Mol. Cell. 54:698-710; Tsai, et al. (2014) Nat. Biotechnol. 32:569-576). In addition, multiple sgRNAs have been expressed using self-cleaving ribozymes from a single expression cassette under the control of the U6 promoter (Xu, et al. (2017) Nucl. Acids Res. 45(5):e28).

SUMMARY OF THE INVENTION

This invention provides a CRISPR/Cas system, which includes a Cas endonuclease and a cognate single guide RNA (sgRNA), wherein: (a) the Cas endonuclease is fused with one or more degron sequences, wherein said degron has (i) a non-canonical Cdc20 or Cdh1 recognition motif, or (ii) a sequence targeted by a ligase selected from the group of EMI1, TRP1, CBL-PTK, CBL-MET, COP1, CRL4-CDT2, Kelch KEAP1, Kelch KLHL3, MDM2-SWIB, ODPH-VHL, SCF-SKP2, SCF-SKP2-CKS1, SCF-CULLIN, SCF-FBW7, SCF-FBX05, SCF-TRCP1, SCF-CUL4, E6-AP, SIAH, HECT domain family, RING finger family, U box family, and combinations thereof; (b) the cognate sgRNA is an activatable sgRNA harboring an inactivation sequence in a non-essential region of the activatable sgRNA, wherein said inactivation sequence comprises one or more endonuclease recognition sites; or (c) a combination of (a) and (b). In some embodiments, the system includes an array of activatable sgRNAs, where the cognate sgRNA targets at least one activatable sgRNA in the array of activatable sgRNAs.

In certain aspects of the Cas fusion protein, the Cas endonuclease is a Cas9 endonuclease. In some embodiments of the Cas fusion protein, the one or more degron sequences are fused to the Cas endonuclease with one or more linkers disposed therebetween. In other embodiments of the Cas fusion protein the one or more degron sequences are fused to the Cas endonuclease at the N-terminus, C-terminus, or N-terminus and C-terminus of the Cas endonuclease.

In certain aspects of the activatable sgRNA, the activatable sgRNA targets a transcribed strand of a nucleic acid molecule. In other aspects of the activatable sgRNA, the inactivation sequence is a cis-acting ribozyme. In some embodiments, the cis-acting ribozyme is encoded by a nucleic acid molecule of SEQ ID NO:2, SEQ ID NO:3 or SEQ ID NO:4. In other embodiments, the activatable sgRNA is encoded by a nucleic acid molecule of SEQ ID NO:14-22. Also included is a nucleic acid having a coding sequence, a 5'-untranslated region and a 3'-untranslated region, wherein said nucleic acid has inserted in the 5'-untranslated region or 3'-untranslated region an activatable sgRNA.

Polynucleotides and vectors encoding the Cas fusion protein and/or activatable sgRNA are also provided as is a method of using the CRISPR/Cas system for editing or modulating transcription of a genome of a cell by introducing the Cas fusion protein and/or activatable sgRNA into the cell. When used in the method of the invention, expression of the Cas endonuclease, activatable sgRNA or Cas endonuclease and activatable sgRNA may be controlled by one or more regulatable promoters. Moreover, in some embodiments, at least two cognate sgRNAs that target two or more sequences are introduced into the cell, wherein the at least two cognate sgRNAs are optionally activatable sgRNA that may be sequentially activated to introduce two or more edits in the genome or modulate transcription of a gene of interest. Further, in other embodiments, the at least one cognate sgRNA is inserted in nucleic acids encoding a 5'- or 3'-untranslated region of a gene.

DETAILED DESCRIPTION OF THE INVENTION

Figure 1:
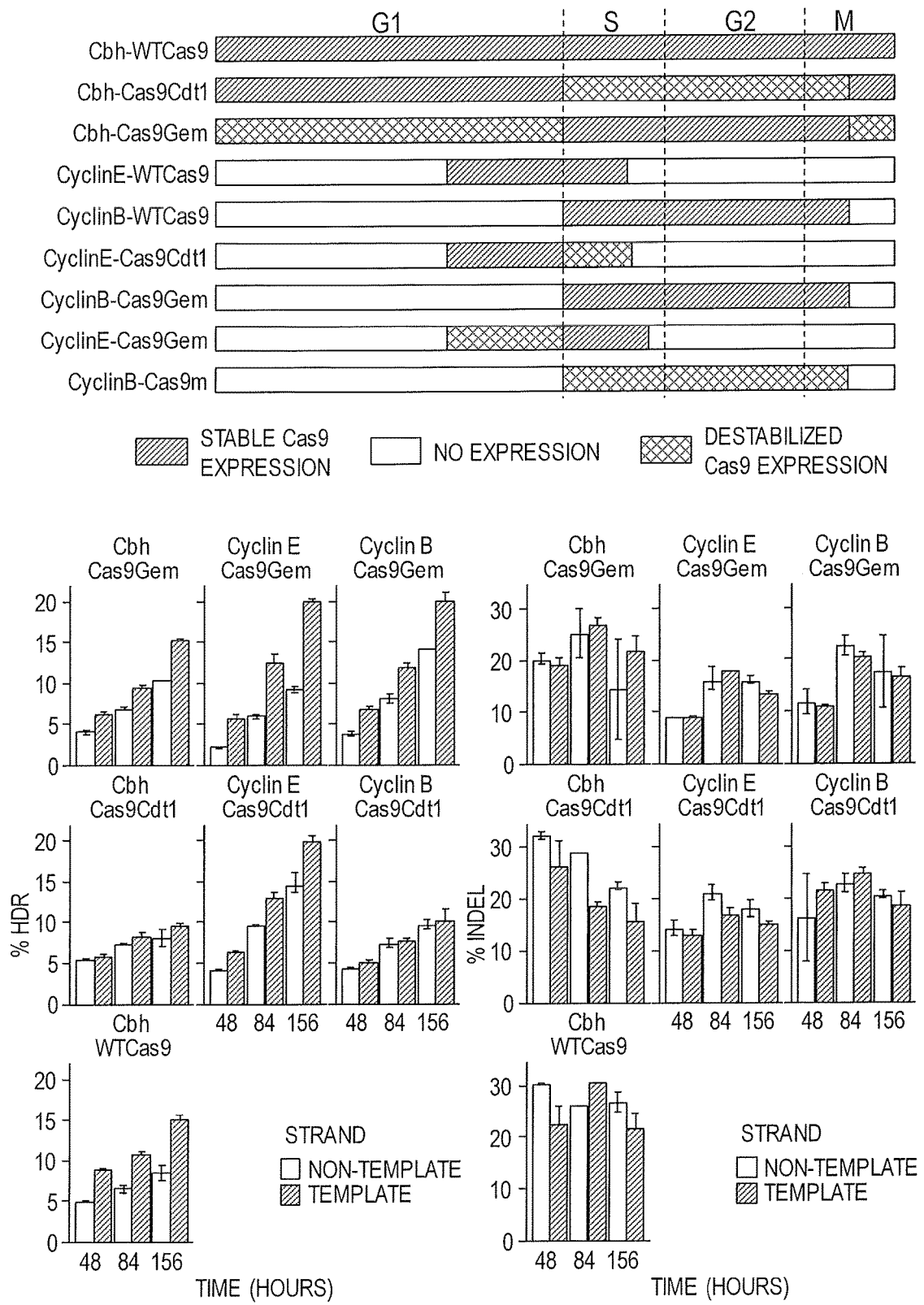
FIG. 1 depicts validated Cas9 variant constructs and their expression/degradation characteristics (top). Measurement of HDR (left bottom) and indel frequencies (right bottom) after targeting of Ctnnb1 for EGFP insertion was performed over the course of 7 days. Mouse embryonic stem cells (mESC) were transiently transfected with respective HDR reagents and Cas9 was targeted to either the template or non-template strand to assess strand biased effects on precise genome edits. HDR frequencies were analyzed via flow cytometry and indel frequencies were measured through deep sequencing of the non-HDR allele. Expression of Cas9 variants using the Cyclin E promoter substantially increases HDR frequencies while reducing indels when compared to constitutively expressed WT-Cas9. Destabilization of Cas9 with the Cdt1 variant enhances indel activity of the non-template sgRNA while reducing HDR frequencies, suggesting an ability to overcome the strand-bias handicapped kinetics that non-template sgRNA typically experience. In general, template sgRNA mediate similar indel mutagenesis as non-template but are superior for HDR.

The Cas9 endonuclease has been adopted for genome editing across many species for its versatility and facile programmability. However, Cas9 is essentially a single-turnover nuclease as it remains bound to the double-strand break it generates, and many regions of a genome are refractory to genome editing. It has now been demonstrated that the refractory nature of Cas9 is due to Cas9 blocking the steps that follow its nuclease activity (DNA repair), therefore inhibiting completion of a genome edit. In this respect, a translocating RNA polymerase will collide with the Cas9-DSB complex and evict Cas9 from the DNA ends if the sgRNA is annealed to the template strand for the RNA polymerase, ultimately facilitating DNA repair and creating a strand bias for genome editing. To alleviate the strand bias and the need for an RNA polymerase, modifying Cas9 through destabilization also alleviates this "blocking" phenomena through increasing the rate at which Cas9 is removed from the DNA. Furthermore, by controlling the expression and degradation of Cas9 to correspond to the cell cycle, the type of genome edit (error prone "NHEJ" or precise "HDR") can be influenced. In addition to modifying Cas9, it now has been shown that the frequency of mutations can be positively influenced by specifically designing the sgRNA to anneal to the transcribed strand of the gene. Design of sgRNA to anneal to the template strand significantly increases mutation frequencies/kinetics, whereas targeting the non-template strand can result in substantially lower mutation frequencies/kinetics due to slower genome editing kinetics. Moreover, by controlling the functionality of specific sgRNA, genome editing activities are not dependent on transcriptional or translational control of the Cas protein. Indeed, it has now been shown that implementing a series of activatable sgRNA, genome editing can be regulated from target site to target site in more of a temporal manner, sequential genome edits can be executed to function like a domino effect, and cells can be barcoded.

Accordingly, the present invention provides a CRISPR/Cas system and use of the same to in editing a genome of a cell, in particular a eukaryotic cell. The CRISPR/Cas system of this invention includes a Cas endonuclease and an activatable cognate sgRNA, wherein the Cas endonuclease is fused with one or more degron sequences and/or the activatable cognate sgRNA harbors an inactivation sequence in a non-essential region of the activatable cognate sgRNA. Given its improved gene editing capabilities, the CRISPR/Cas system of the invention finds use in gene therapy, drug screening, genetic recording, genetic circuitry, and disease diagnosis and prognosis.

The terms "CRISPR/Cas", "CRISPR/Cas system" and "nucleic acid-targeting system" may be used interchangeably. CRISPR-Cas systems are known in the art. See, for example, U.S. Pat. Nos. 8,697,359; 8,771,945; 8,795,965; 8,865,406; 8,871,445; 8,889,356; 8,895,308; 8,906,616; 8,932,814; 8,945,839; 8,999,641; U.S. application Ser. Nos. 14/704,551; 15/192,095; and PCT Publication Nos. WO2016106244 and WO2014093622. See also, Komor, et al. (2017) Cell 168(1-2):20-36.

The CRISPR/Cas system of this invention includes an RNA-guided nuclease, also referred to herein as a Cas endonuclease or Cas protein, and a cognate guide RNA. As is conventional in the art, the guide RNA, also referred to herein as a single guide RNA, sgRNA, or gRNA, guides a cognate Cas protein to specific sites in the genome for targeted cleavage. As used herein, "cognate" refers to a Cas protein and a sgRNA that are capable of forming a nucleoprotein complex, which directly binds to a target nucleic acid molecule that is complementary to a nucleic acid sequence present in the sgRNA.

As is conventional in the art, "complementarity" refers to the ability of a nucleic acid molecule to form hydrogen bond(s) with another nucleic acid molecule (e.g., through traditional Watson-Crick base-pairing). A percent complementarity indicates the percentage of residues in a nucleic acid molecule that can form hydrogen bonds with a second nucleic acid sequence. When two polynucleotide sequences have 100% complementary, the two sequences are perfectly complementary, i.e., all of the contiguous residues of a first polynucleotide hydrogen bond with the same number of contiguous residues in a second polynucleotide.

Cas Fusion Protein. As indicated, this invention provides a CRISPR/Cas system including a Cas endonuclease fused with one or more degron sequences, generally referred to herein as a "Cas fusion protein" or "fusion protein." Cas endonucleases are known in the art and include, but are not limited to, Cas proteins such as Cas1, Cas1B, Cas2, Cas3, Cas4, Cas5, Cas6, Cas7, Cas8, Cas9 (also known as Csn1 and Csx12), Cas10, Cas12a, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and homologs thereof, or modified versions thereof. In some embodiments, the Cas is a dCas9 protein (Cas9 endonuclease dead protein, e.g., with point mutations D10A and H840A) or fusion protein thereof. Although dCas9 lacks endonuclease activity, it is still capable of binding to its guide RNA and the target nucleic acid molecule. This ability to bind DNA can be used to either block transcription of the targeted gene by fusing the dCas9 to a transcriptional repressor peptide such as KRAB or to activate transcription by fusing the dCas9 with an activation domain such as VP64-p65-Rta (VPR). The nucleic acid and amino acid sequences of these Cas proteins are readily available from public sources including GENBANK and SwissProt. By way of illustration, the *Streptococcus pyogenes* Cas9 protein sequence is available under SwissProt accession number Q99ZW2. Likewise, the *Actinobacillus suis* Cas9 is available under GENBANK accession number WP 014991277. Preferably, the CRISPR enzyme is a Cas9 protein. Representative Cas9 proteins include, but are not limited to Cas9 from Streptococci including *S. pyogenes, S. pneumoniae*, and the like and Cas9 from *Staphylococcus aureus, Neisseria meningitides* and *Treponema denticola*.

Additional RNA-guided nucleases include Cas12a nucleases ("Cas12a" formerly "Cpf1") including Cas12a from Providicella, *Francisella, Acidaminococcus* and Lachnospiracae.

To regulate Cas protein stability and hence the rate at which Cas9 is removed from the DNA, this invention includes a fusion protein composed of a Cas endonuclease fused with one or more degron sequences. As used herein, a "degron" refers to a specific sequence of amino acids in a protein that confers metabolic instability of degradation. A degron sequence can occur at either the N- or C-terminal region, and these are called N-degrons or C-degrons, respectively. A degron may be any amino acid sequence, or combination of sequences, that confers degradation to a protein that it is fused to.

The ordered progression through the cell cycle depends on regulating the abundance of several proteins through ubiquitin-mediated proteolysis. Degradation is precisely timed and specific. One example of such degradation system is the anaphase promoting complex (APC), a ubiquitin protein ligase. APC is activated both during mitosis and late in mitosis/G1, by the WD repeat proteins Cdc20 and Cdh1, respectively. These activators target distinct sets of substrates. APC/C-Cdc20 and –Cdh1 coactivator complexes recognize most of their substrates through recognition of the canonical motifs: the D (destruction)-box degron (Arg-Xaa-Xaa-Leu-Asp (SEQ ID NO:111) or Arg-Xaa-Xaa-Leu (SEQ ID NO:112)) and the KEN box degron (a three amino acid motif of Lys-Glu-Asn). In this respect, a "canonical Cdc20 or Cdh1 recognition motif" refers to the classically characterized Cdc20 and Cdh1 recognition motifs, i.e., the D-box and KEN box motifs. In some embodiments, the degron contains a canonical Cdc20 or Cdh1 recognition motif. Examples of naturally occurring proteins that include a D-box degron are cell cycle-dependent cyclins (CDKs) such as Cyclin A and Cyclin B and other cell cycle-regulated proteins such as Hsl1, Cdc6, Fin1, p21 and Geminin. Representative D-box degron amino acid sequences include RPALSD (SEQ ID NO:113), RPALS (SEQ ID NO:114) and RLALD (SEQ ID NO:115). Examples for naturally occurring proteins that include a KEN box degron are Cdc20, Sgol, Nek2 and B99. Other proteins which contain either a D-box or a KEN box are well-known in the art (Glotzer, et al. (1991) 991, *Nature* 349:132-138; Pfleger & Kirschner (2000) Genes Dev. 14(6):655-665).

In other embodiments, the degron is not a canonical Cdc20 or Cdh1 recognition motif. Accordingly, in some aspects, the degron is a non-canonical Cdc20 or Cdh1 recognition motif. A "non-canonical Cdc20 or Cdh1 recognition motif" refers to a Cdc20 or Cdh1 motif that is a motif other than a D-Box or KEN box motif. Non-canonical Cdc20 and Cdh1 recognition motifs include the LXXK motif, A-motif, CRY-box and RL tail.

"LXXK" degron is a non-canonical APC/Cdh1 target that renders its protein targetable to the proteasome. LXXK degrons include the amino acid sequence LXXK (SEQ ID NO:116), wherein X can be any amino acid residue. A representative LXXK degron sequence is LASK (SEQ ID NO:117).

The A-motif is a sequence that enhances APC-Cdh1 binding to facilitate targeting to the proteasome. A-motif degrons include the amino acid sequence EET. A representative A-motif degron sequence is EETAE (SEQ ID NO:118).

The CRY-box motif is a degron recognized by APC/C for targeting to the proteasome. This degron includes the amino acid sequence CRYXPS (SEQ ID NO:119), where X can be any amino acid residue. A representative CRY-box degron sequence is CRYIPS (SEQ ID NO:120).

The RL tail motif of Emi1/Emi2 serves as a docking site for the APC/C, thereby promoting the interaction and inhibition of the APC/C-Cdh1. This degron includes the amino acid sequence (T/S)KKSKKNL(R/Q)RL (SEQ ID NO: 56), where X can be any amino acid residue. A representative RL tail degron sequence is TKKSKKNLRRL (SEQ ID NO: 57).

In other aspects of this invention, the degron is neither a canonical nor non-canonical cdc20 or Cdh1 recognition motif. In accordance with this aspect of the invention, the degron may mediate ubiquitin-dependent degradation or ubiquitin-independent degradation (e.g., via PEST degrons disclosed herein). In some embodiments, the degron has a sequence targeted by a ligase selected from the group of EMI1, TRP1, CBL-PTK, CBL-MET, COP1, CRL4-CDT2, Kelch KEAP1, Kelch KLHL3, MDM2-SWIB, ODPH-VHL, SCF-SKP2, SCF-SKP2-CKS1, SCF-CULLIN, SCF-FBW7, SCF-FBX05, SCF-TRCP1, SCF-CUL4, E6-AP, SIAH, HECT domain family, RING finger family, U box family, and a combination thereof. Examples of degrons that do not serve as recognition motifs for either Cdc20 or Cdh1 include, e.g., the PHD domain, PIP motif, Cy motif, ABBA motif, and the like (Table 1).

TABLE 1

| Degron | Substrate | Motif Sequence |
|---|---|---|
| APC/C ABBA | Cyclin A2 | FTIHVDEAE (SEQ ID NO: 80) |
| PIP | Cdt1 | QRRVTDFF (SEQ ID NO: 81) |
|  | Cdt1 | QTSMTDFY (SEQ ID NO: 82) |
|  | *** | QXX(V/L/M/I)XX(F/Y)(F/Y) (SEQ ID NO: 83) |
| PHD domain | *** | CHC |
| Cy motif | Cdt1 | RRL |
|  | HIV-1 Viral infectivity factor | RKL |
|  | *** | RXL |
| APC/C TRP1 | Anaphase-promoting complex subunit 10 | SIR |
|  | Cell division cycle protein 20 homolog | GIR |
|  | Fizzy-related protein homolog | RIR |
|  | Kinesin-like protein KIF18A | NLR |
|  | Serine/threonine-protein kinase Nek2 | GMR |
| CBL-PTK | Tyrosine-protein kinase ZAP-70 | DGYTPEP (SEQ ID NO: 84) |
|  | Protein sprouty homolog | NEYTEGP (SEQ ID NO: 85) |
| CBL-MET | Hepatocyte growth factor receptor | DYR |
| COP1 | Transcription factor jun-D | DEPQTVPD (SEQ ID NO: 86) |
|  | Transcription factor AP-1 | EEPQTVPE (SEQ ID NO: 87) |
|  | ETS translocation variant 5 | DEQFVPD (SEQ ID NO: 88) |
| CRL4-CDT2 | Cyclin-dependent kinase inhibitor 1 | TSMTDFYHSKRRL (SEQ ID NO: 58) |
|  | Cyclin-dependent kinase inhibitor 1C | PLISDFFAKRKRS (SEQ ID NO: 59) |
|  | DNA replication factor Cdt1 | RRVTDFFARRRP (SEQ ID NO: 60) |
|  | N-lysine methyltransferase SETD8 | RKLTDFYPVRRS (SEQ ID NO: 61) |

TABLE 1-continued

| Degron | Substrate | Motif Sequence |
|---|---|---|
| Kelch KEAP1 | Nuclear factor erythroid 2-related factor 2 | DEETGE (SEQ ID NO: 89) |
| | Serine/threonine-protein phosphatase PGAM5 | NVESGE (SEQ ID NO: 90) |
| | Inhibitor of nuclear factor kappa-B kinase subunit beta | NQETGE (SEQ ID NO: 91) |
| | Nucleosome-remodeling factor subunit BPTF | DPENGE (SEQ ID NO: 92) |
| | Nuclear factor erythroid 2-related factor 1 | DGETGE (SEQ ID NO: 93) |
| Kelch KLHL3 | Serine/threonine-protein kinase WNK1 | EPEEPEADQH (SEQ ID NO: 62) |
| | Serine/threonine-protein kinase WNK3 | ECEETEVDQH (SEQ ID NO: 63) |
| MDM2-SWIB | Tumor protein 63 | FQHIWDFL (SEQ ID NO: 94) |
| | Tumor protein p73 | FEHLWSSL (SEQ ID NO: 95) |
| | Cellular tumor antigen p53 | FSDLWKLL (SEQ ID NO: 96) |
| | Protein numb homolog | FEAQWAAL (SEQ ID NO: 97) |
| | Numb-like protein | FEAQWAAL (SEQ ID NO: 98) |
| ODPH-VHL | Endothelial PAS domain-containing protein 1 | LAPYIPMDGEDFQL (SEQ ID NO: 64) |
| | Hypoxia-inducible factor 1-alpha | LAPAAGDTIISLDF (SEQ ID NO: 65) |
| SCF-FBW7 | G1/S-specific cyclin-E1 | LLTPPQS (SEQ ID NO: 99) |
| | G1/S-specific cyclin-E1 isoform-3 | LTPPQS (SEQ ID NO: 100) |
| | Transcription factor AP-1 | PGETPPLS (SEQ ID NO: 101) |
| | Uracil-DNA glycosylase H. | PGTPPSS (SEQ ID NO: 102) |
| SCF-SKP2-CKS1 | Cyclin-dependent kinase inhibitor 1B | SVEQTPKK (SEQ ID NO: 103) |
| SCF-TRCP1 | NF-kappa-B inhibitor beta | DSGLGS (SEQ ID NO: 104) |
| | NF-kappa-B inhibitor epsilon | DSGIES (SEQ ID NO: 105) |
| | Catenin beta-1 | DSGIHS (SEQ ID NO: 106) |
| | F-box only protein 5 | DSGYSS (SEQ ID NO: 107) |
| SIAH | POU domain class 2-associating factor 1 | APTAVVLPH (SEQ ID NO: 108) |
| | AF4/FMR2 family member 4 | KPTAYVRPM (SEQ ID NO: 109) |
| | E3 ubiquitin-protein ligase SH3RF1 | RPTAAVTPI (SEQ ID NO: 110) |

*** Consensus sequence. X represents any amino acid residue. See also, Guharoy et al. (2016) *Nat. Commun.* 7: 10239.

In some embodiments, the degron is obtained from the amino acid sequence of Cdt1, and preferably has an amino acid sequence as set forth in SEQ ID NO:76. In another embodiment, the degron is obtained from the amino acid sequence of geminin, and preferably has an amino acid sequence as set forth in SEQ ID NO:77. In other embodiments, the degron is obtained from the amino acid sequence of ornithine decarboxylase, and preferably has an amino acid sequence as set forth in SEQ ID NO:78 or SEQ ID NO:79.

Although a degron of a protein of any organism may be fused to Cas protein in any cell type to confer degradation to the nuclease, the use of a degron of a protein endogenous to a host cell, or a degron of a protein of the most closely related species to the host cell, is preferred.

The degron may be added to the Cas protein on its C-terminus, N-terminus or on both termini by conventional recombinant protein production methods. In this respect, the fusion protein is a non-naturally occurring or engineered CRISPR enzyme associated with at least one degron sequence. The degron may be inserted as a single copy or as multiple copies. Moreover, a Cas fusion protein may include more than one type of degron. In certain embodiments, nucleic acids coding for the Cas fusion protein may be codon optimized for expression in a eukaryotic cell.

In some embodiments, the Cas9 fusion protein of this invention cleaves both strands of DNA to produce a double strand break (DSB). In certain embodiments, the Cas9 fusion protein is a nickase. In other embodiments, the Cas9 fusion protein is a dual nickase. In further embodiments, the Cas9 fusion protein is a deadCas9 (dCas9), e.g., a Cas9 having substantially no nuclease activity, e.g., no more than 5% nuclease activity as compared with a wild-type Cas9 or Cas9 not having had mutations thereto. Moreover, the Cas9 fusion protein may be associated with one or more functional domains (e.g., transcriptional, repressors or activators). More specifically, the Cas9 fusion protein is a dCas9 and/or is associated with one or more functional domains (e.g., transcriptional regulators such as VPR or KRAB).

In some aspects, the Cas9 fusion protein has a Rec2 or HD2 truncation. In some embodiments, the degron may be associated with the Cas endonuclease via a connector protein, for example using a system such as a marker system such as the streptavidin-biotin system. As such, provided is a fusion of a Cas endonuclease with a connector protein specific for a high affinity ligand for that connector, whereas the degron is bound to said high affinity ligand. For example, streptavidin may be the connector fused to the Cas endonuclease, while biotin may be bound to the degron. Upon co-localization, the streptavidin will bind to the biotin, thus connecting the Cas endonuclease to the degron.

Preferably, the Cas endonuclease is fused or covalently attached to the degron. In some embodiments, the fusion may be to the N-terminal end of the Cas endonuclease. In some embodiments, at least one degron is fused to the N-terminus of the Cas endonuclease. In other embodiments, the fusion may be to the C-terminal end of the Cas endonuclease. In further embodiments, at least one degron is fused to the C-terminus of the Cas endonuclease. In some embodiments, one degron may be fused to the N-terminal end of the Cas endonuclease with another degron fused to the C-terminal of the Cas endonuclease. In some embodiments, the Cas endonuclease is associated with at least two degrons and wherein a first degron is fused to the N-terminus of the Cas endonuclease and a second degron is fused to the C-terminus of the Cas endonuclease, the first and second degrons being the same or different. In some embodiments, the fusion may be to the N-terminal end of the degron. In other embodiments, the fusion may be to the C-terminal end of the degron. In some embodiments, the fusion may between the C-terminal end of the Cas endonuclease and the N-terminal end of the degron. In other embodiments, the fusion may between the C-terminal end of the degron and N-terminal end of the Cas endonuclease.

In some embodiments, one or two degrons may be fused to the N-terminal end of the Cas endonuclease with one or two degrons fused to the C-terminal of the Cas endonuclease. In some embodiments, the at least two degrons are associated with the Cas endonuclease and the degrons are the same degron, i.e., the degrons are homologous. In some embodiments, the at least two degrons are associated with the Cas endonuclease and the degrons are different degrons, i.e., the degrons are heterologous. Having two or more degrons which are heterologous may be advantageous as it would provide a greater level of degradation control. A tandem fusion of more than one degron at the N- or C-terminus may enhance degradation. It is envisaged that high levels of degradation would occur in the absence of either stabilizing ligand, intermediate levels of degradation would occur in the absence of one stabilizing ligand and the presence of the other (or another) stabilizing ligand, while low levels of degradation would occur in the presence of both (or two of more) of the stabilizing ligands.

The fusion protein may include the Cas protein directly fused to the degron, or alternatively the Cas protein is fused with the degron via a linker. In some embodiments, the linker is a Gly-Ser linker. In other embodiments, the fusion protein further includes at least one Nuclear Export Signal (NES). In some embodiments, the fusion protein includes two or more NESs. In some embodiments, the fusion protein includes at least one Nuclear Localization Signal (NLS). This may be in addition to an NES. In some embodiments, the fusion protein comprises, consists of, or consists essentially of Cas protein, degron and a localization (nuclear import or export) signal as, or as part of, the linker between the Cas protein and the degron. HA or FLAG® tags may also be used as linkers. In certain aspects, the fusion, protein includes an NLS and/or NES and/or Gly-Ser linker having the amino acid sequence GSGGSGS or (GGGGS)$_3$ (SEQ ID NO:66).

Expression of the fusion protein may be placed under the control of a constitutive promoter or regulatable promoter, e.g., a tissue-specific promoter, chemically-inducible promoter or a cell cycle-regulated promoter such as, e.g., a promoter of a cyclin B, E, A, or D gene controlled by Rb or E2F transcription factors. Placing expression of the fusion protein under control of a cell-cycle promoter will regulate the timing of the expression and subsequent activities of the fusion protein.

"Under control of a regulatable promoter" or "controlled by a regulatable promoter" means that the DNA sequences encoding product of interest will be downstream of the promoter element that controls the transcription of its RNA products. A "regulatable promoter" is any promoter whose activity is affected by a cis- or trans-acting factor. A regulatable promote of this invention can be regulated by cell cycle, i.e., through endogenous transcription factors such as E2F or Rb being recruited to the promoter DNA elements at specific points in a cell's cycle to either repress or turn on transcription of that gene by RNA polymerase II; tissue-specific induction; chemical induction, i.e., via contact with a toxin, growth factor, steroid, heavy metal, etc.; or environmental stimuli, e.g., via light or temperature.

The present invention also provides a polynucleotide encoding the Cas-degron fusion protein. In some embodiments, the encoded fusion protein is operably linked to a first regulatory element. In some embodiments, a degron is also encoded and is operably linked to a second regulatory element. Advantageously, the degron here is to "mop up" the stabilizing ligand and is advantageously the same degron (i.e., the same type of domain) as that associated with the fusion protein. As used herein, the term "mop up" is meant in the sense of performing so as to contribute or conclude activity. In some embodiments, the first regulatory element is a promoter and may optionally include an enhancer. In some embodiments, the second regulatory element is a promoter and may optionally include an enhancer. In some, embodiments, the first regulatory element is an early promoter. In some embodiments, the second regulatory element is a late promoter. In some embodiments, the second regulatory element is, comprises, or consists essentially of an inducible control element, optionally the tet system, or a repressible control element, optionally the tetr system. An inducible promoter may be favorable, e.g., rTTA, to induce tet in the presence of doxycycline.

The present invention further provides a means for delivering the Cas-degron fusion protein of the invention or polynucleotides encoding said fusion protein. Such delivery means can include, e.g., particle(s) of the fusion protein, vector(s) harboring polynucleotide(s) encoding the fusion protein; and/or RNA of the CRISPR/Cas complex. Vectors can include a DNA plasmid, a bacterial artificial chromosome (BAC), a yeast artificial chromosome (YAC), a viral vector, or a nucleic acid complexed with a delivery vehicle such as a liposome or poloxamer. In some embodiments, the vector may be a plasmid or a viral vector such as AAV, or lentivirus. Transient transfection, with plasmids, e.g., into HEK cells may be advantageous, especially given the size limitations of AAV. While SpCas9 fits into AAV, one may reach an upper limit with nucleic acid encoding one or more degrons.

Figure 3:
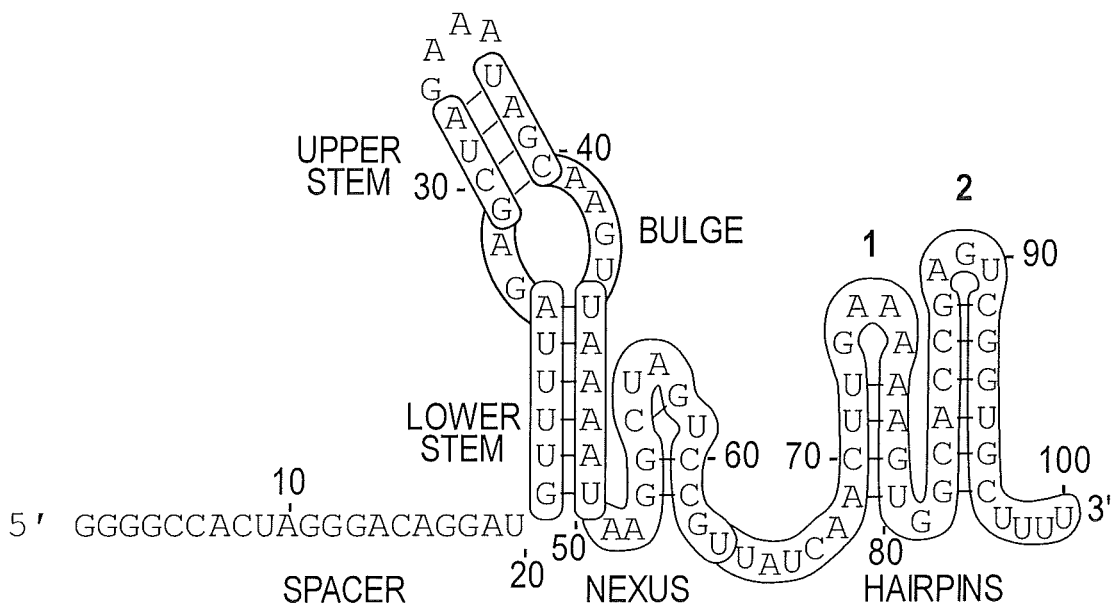
FIG. 3 is an illustration depicting the structure of an unmodified Streptococcus pyogenes sgRNA (SEQ ID NO:1).

Activatable sgRNA. As is known in the art, a single guide RNA ("sgRNA" or "gRNA") refers to a chimeric RNA molecule which is composed of a CRISPR RNA (crRNA) and trans-encoded CRISPR RNA (tracrRNA). A conventional sgRNA (FIG. 3) has a (i) 5' start (typically a G, guanosine nucleotide); (ii) a DNA guiding element or spacer sequence, which is complementary to the target nucleic acid molecule; (iii) a lower and upper stem, bulge, and nexus, which interact with Cas (i.e., the Cas binding element), and (iv) one or more hairpin structures (Briner, et al. (2014) Mol. Cell 56(2):333-339).

In accordance with this invention, the distance from the 5' start to the DNA guiding element or spacer sequence can be 0 (i.e., the start is part of the guiding element) to 40 nt (nucleotides), preferably 0 to 20, or 0 to 10 nt or even 1 to 5 nt in length. The DNA guiding element or sequence can be 8 to 50 nt in length, preferably 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 42, 44, 46, 48 nt in length or any range in between; preferred are 15-30 nt in length an even more preferred length is 17-19 nt, which minimizes off-target events (Wiles, et al. (2015) Mamm. Genome 26:501-510). The distance between the DNA guiding element or sequence and the Cas binding element or sequence may be 0 nt (directly adjacent) to 30 nt, preferably 0 nt to 20 nt or 2 to 10 nt in length.

The DNA guiding element or spacer sequence can be chosen freely to hybridize to a target nucleic acid molecule. sgRNA/CRISPR targeting and methods of selecting suitable DNA guiding sequences and modifications of the guide RNA are disclosed in, e.g., WO 2014/093709, WO 2014/144761, WO 2015/089486, WO 2015/048577, WO 2015/123339, WO 2015/089486, WO 2015/089427, and WO 2015/113063. The guiding element or spacer sequence typically shares 100% sequence identity with the target sequence, although at least 80%, 85%, 90%, and 95% sequence identity to the target sequence is also contemplated so long as the sgRNA provides the necessary specificity for the CRISPR/Cas system. As used herein, "target nucleic acid," "target nucleic acid molecule," "target sequence" or "target DNA molecule" refers to a genomic or mitochondrial DNA site to be edited by the CRISPR/Cas system. The sequence of the sgRNA allows for many variations as long as it is capable of binding Cas and having a complementary region that binds to the target nucleic acid.

In particular embodiments, the sgRNA has a DNA guiding element that is complementary or specifically hybridizes to the template or transcribed strand of the target nucleic acid molecule. The data presented herein indicate that mutagenesis frequencies can be increased by specifically targeting the sgRNA to the template strand of the target nucleic acid molecule. More particularly, during genome editing, the Cas nuclease is targeted to a genomic DNA sequence via the sgRNA. Upon Watson-crick base pairing of sgRNA to the target nucleic acid molecule, Cas introduces a double stranded break. The Cas:sgRNA-DSB (Cas:DSB) state is unusually stable and remains in complex unless a substantial force, such as a translocating RNA polymerase (RNAP) collides with it. Collisions of RNAP with the Cas-DSB disrupt the complex only if the sgRNA is annealed to the template strand for the RNAP. This mechanism for disrupting the Cas-DSB complex increases mutagenesis frequencies substantially and provides an explanation for the observation that the dissociation of Cas-DSB complex is the rate-limiting step of genome editing. Accordingly, selection of an sgRNA that targets the transcribed strand can be used to increase kinetics of genome editing, whereas selection of the non-template can be used to decrease kinetics of genome editing. Modulating the kinetics via template or non-template strand selection is of use in modulating the barcoding and/or bioprocessing technologies described herein.

To select the template strand for a single gene, the orientation of the gene within the genome is first determined. Specifically, it is assessed whether the strand utilized by RNA polymerase as the template is oriented on the plus or minus, strand of the genome. Typically, a user can identify a template sgRNA by accessing the DNA sequence of a gene of interest from a public database. Notably, public databases generally orient genes so that the coding strand is in the 5'→3' orientation. Prospective sgRNA for introducing a genetic knock-out may be chosen to hybridize to a sequence located downstream of the start codon (but within an exon-preferably exons 1, 2, or 3) by using an online sgRNA selection tool (e.g., CRISPOR) or finding a suitable protospacer-adjacent motif (PAM) site (e.g., 5'-NGG-3', 5'-NNNNGATT-3', 5'-NNAGAAW-3' or 5'-NAAAAC-3') on the template strand. Selection of a number of potential sgRNA should be performed for each experiment and each sgRNA should be checked for off-target activity. Furthermore, the user should confirm that the gene of interest is known to be expressed and if the gene exists in a state of closed chromatin (e.g., by looking at DNase hypersensitive site data). Closed chromatin can negatively impact mutation frequencies, and lack of transcription through the Cas target site will reduce the effect of strand selection.

The Cas binding element or sequence of an sgRNA preferably includes a stem loop or at least a double strand region. Preferably the stem loop is 6 to 50 nt in length, e.g., 7, 8, 9, 10, 11, 12, 13, 14, 15, 16, 17, 18, 19, 20, 21, 22, 23, 24, 25, 26, 27, 28, 30, 32, 34, 36, 38, 40, 45, 50 nt or more in length or any range in between these values. The stem loop may have 60% to 100% complementary nucleotides, including A-U (coded by T on the sense-strand of a dsDNA), G-C and G-U (coded by T) base pairs. Preferably the complementary nucleotides are 70% to 95% or 80% to 90% complementary. The sequence of the loop is not essential and may even protrude the Cas binding region, and leave only the stem region in the Cas binding pocket. Upon binding to the specific target nucleic acid via the sgRNA, Cas generates a break (e.g., double- or single-strand break) in the target nucleic acid at the PAM site.

The 3' portion of the sgRNA may be 20 to 600 nt in length. Usually this region can be designed relatively freely. If too long, it may even be digested by naturally occurring enzymes, which will automatically result in a suitable size for the CRISPR/Cas system. Possible lengths are 20 to 400 nt, 25 to 300 nt or 30 to 200 nt. In total, the sgRNA has preferably a size 60 to 2000 nt in length, preferably 70 to 1500 nt, or 80 to 1000 nt, 90 to 800 nt, 100 to 500 nt, 120 to 300 nt in length.

Structural analysis of Cas9 indicates that whereas the bulge and nexus regions of the cognate sgRNA are the most critical features for Cas9 targeting, hairpin 1, hairpin 2, and the upper and lower stem loop regions are relatively tolerant to sequence variations, including nucleotide substitutions, insertions and deletions and even predicted structural disruptions (Briner, et al. (2014) Mol. Cell 56(2):333-339).

Accordingly, the present invention takes advantage of these non-essential regions of the sgRNA to insert inactivation sequences that allow for the production an sgRNA that is nonfunctional until activated. In this respect, in addition, or as an alternative to the Cas-degron fusion protein, this invention also provides an activatable sgRNA. As used herein, an "activatable sgRNA" refers to a modified sgRNA molecule that exists in a state where Cas cannot bind to the modified sgRNA and introduce DNA breaks. In certain embodiments, an activatable sgRNA is integrated or inserted into a genome of interest. During the inactive state, activatable sgRNA are transcribed, but the RNA molecule is non-functional for Cas binding/activity due to the presence of an inactivation sequence located in a non-essential region of the sgRNA. The inactivation sequence is located in regions within or outside of the sgRNA that can handle modification, but that are not dispensable for Cas function. In certain embodiments, a nonessential region refers to a hairpin (e.g., hairpin 1 or hairpin 2 of Cas9 sgRNA), an upper stem loop and/or a lower stem of the sgRNA. In particular embodiments a nonessential region of an sgRNA is a hairpin.

An "inactivation sequence" refers to a nucleic acid sequence that causes the sgRNA to be inactive via (i) steric hindrance of Cas binding through bulky structures that, e.g., disrupt sgRNA folding, intrinsic RNA structures or recruited protein binding; (ii) cis- or trans-ribozyme insertion; or (iii) cellular (endogenous or exogenous) RNase activity (e.g., RNase P/Z). An inactive, activatable sgRNA can be activated through targeting a Cas or specific nuclease to the DNA of each inactivation sequence. This targeting introduces a mutation that destroys a critical region of the inactivation sequence, and restores the ability for Cas to bind the newly modified and functional activatable sgRNA. In certain embodiments, the activatable sgRNA harbors an inactivation sequence in a non-essential region of the sgRNA, wherein said inactivation sequence includes one or more endonuclease recognition sites. The term "endonuclease recognition site" refers to a nucleic acid sequence or structural motif recognized by an endonuclease, which cleaves the nucleic acid at or near the structural motif. In certain embodiments, a pair of endonuclease recognition sites is used that are targeted by the same or different endonucleases. Ideally, the pair of endonuclease recognition sites are at the ends of (i.e., flank) the inactivation sequence to allow endonuclease-mediated removal of the inactivation sequence. In certain embodiments, the endonuclease recognition sites are recognized and cleaved by Cas9. Notably, insertion of an activatable sgRNA into the 5'- or 3'-UTR of an endogenous gene functions to regulate Cas9 activity by linking sgRNA expression (and hence availability for binding with Cas9) to expression of the gene in which the sgRNA is inserted. In this aspect, the activatable sgRNA is expressed in an "off-state," an RNA-guided nuclease (e.g., Cas9) excises the activation sequence from the activatable sgRNA thereby converting the activatable sgRNA to the "on-state" where it can bind to its cognate Cas endonuclease.

In certain embodiments of this invention, the inactivation sequence is a cis-acting ribozyme. A "cis-acting ribozyme" is a catalytic RNA molecule that can act on a target RNA that is adjacent or proximal to its location. Ribozyme cleavage is site-specific and is mediated by hydrogen bonding between complementary bases at target regions. Cis-acting ribozymes are known in the art and include, e.g., Hammerhead, Hepatitis delta virus (HDV), hairpin, Varkud satellite (VS), Group I intron, and Group II intron ribozymes (Doudna & Cech (2002) *Nature* 418:222-228). In certain embodiments, the inactivation sequence is a cis-acting ribozyme encoding by a nucleic acid molecule of SEQ ID NO:2, SEQ ID NO:3 or SEQ ID NO:4.

In particular embodiments of this invention, the activatable sgRNA is encoded by a nucleic acid molecule as set forth in Table 2, wherein "n^n" represents a nucleotide sequence of an endonuclease recognition site, each of which may be recognized by the same or different endonuclease; and "X" represents an inactivation sequence. In certain embodiments, "X" represents a cis-acting ribozyme and "n^n" represents endonuclease recognitions sites for Cas9 endonuclease.

TABLE 2

| sgRNA | Sequence | SEQ ID NO: |
|---|---|---|
| Cas9 | gttttagagctagaaatagcaagttaaaataaggcta gtccgttatcaactn^nxn^n aagtggcaccgagtc ggtgctttt | 14 |
| Sth CRISPR3 | gttttagagctgggn^nxn^n acccagcgagttaaa ataaggcttagtccgtactcaacttgaaaaggtggca ccgattcggtgttttt | 15 |
| Sth CRISPR3 | gttttagagctgggtacccagcgagttaaataaggc ttagtccgtactcaacttgan^nxn^n aaggtggca ccgattcggtgttttt | 16 |
| Sth CRISPR1 | gtttttgtactctggn^nxn^n accagaagctacaa agataaggcttcatgccgaaatcaacaccctgtcatt ttatggcaggtgtttt | 17 |
| Sth CRISPR1 | gtttttgtactctggtaccagaagctacaaagataag gcttcatgccgaaatcaacaccctgtcatn^nxn^n ttatggcaggtgtttt | 18 |
| Cas12a | tagatgttgtcatctttan^nxn^n | 19 |
| Cas12a | tagatgttgtcatn^nxn^n tttaa | 20 |
| Sa CRISPR | gttttagtactctggaaacagaatctactaaaacaag gcan^nxn^n gacgaatgccgtgtttatctcgtcaa cttgttggcgagatttttt | 21 |
| Sa CRISPR | Gttttagtactctggaaacagaatctactaaaacaag gcaagacgaatgccgtgtttatctcgtcaact n^nxn^n tgttggcgagatttttt | 22 |

Sp, *Steptococcus pyogenes*;
Sth, *Streptococcus thermophilus*;
Sa, *Staphylococcus aureus*.

For use in the system and method of this invention, the sgRNA may be provided as an isolated polynucleotide (e.g., DNA molecule) encoding the sgRNA, which may optionally be included in a vector (e.g., a plasmid). In certain embodiments, it is preferable that the activatable sgRNA is integrated into the genome. The activatable sgRNA of this invention is useful in a variety of applications including, for example, lineage tracing wherein an array of activatable sgRNA target each other in a temporally controlled manner; sequential genetic knock-outs wherein mutations are introduced over time in a controlled manner; transcriptional programming using Cas9-VPR and 14nt sgRNAs, Cas9 nucleases with altered PAM specificities, or orthogonal RNA-guided nucleases using an array of activatable sgRNA where some or all sgRNA have a secondary function to either bind to or activate another sgRNA that functions to direct a transcriptional activity of dCas9 (nuclease dead Cas9) or Cas9-14nt sgRNA complex to a target gene; and/or biological circuits, i.e. "if gene A is on turn off gene B".

Accordingly, in certain embodiments of this invention, the system further provides an array of activatable sgRNAs, where the activatable cognate sgRNA targets at least, one activatable sgRNA in the array of activatable sgRNAs. See, e.g., FIG. 7, FIG. 9 and FIG. 10. In some embodiments, the activatable sgRNAs of the array are adjacent to one another. In other embodiments, the activatable sgRNAs of the array are non-adjacent to one another.

The CRISPR/Cas system of this invention may include the use of a conventional Cas protein in combination with an activatable cognate sgRNA; a Cas-degron fusion protein in combination with a conventional sgRNA, or both a Cas-degron fusion protein and an activatable sgRNA. One or both components of the CRISPR/Cas system may be provided in a kit for genome editing, which includes nucleic acids encoding one or both of the Cas-degron fusion protein and activatable sgRNA, e.g., in the form of plasmids, as well as instructions for using the CRISPR/Cas system for genome editing. The kit may optionally include, e.g., ligation components, storage buffers, reaction buffers, and transformation competent cells. The sgRNA of the system and kit can be tailored to specifically target a gene of interest by insertion of a suitable DNA guiding element. In certain embodiments, the sgRNA is targets the template or non-template strand, wherein template strand increases kinetics of activation and non-template reduces kinetics.

In addition to a CRISPR/Cas system, Cas-degron fusion protein, activatable sgRNA, and kit, this invention also provides a method of editing or modulating transcription of a genome of a cell (e.g., nuclear DNA or mitochondrial DNA) by introducing or delivering to the eukaryotic cell at least one Cas endonuclease and at least one cognate sgRNA that targets a nucleic acid sequence of the genome, wherein the Cas endonuclease is fused with one or more degron sequences and/or the cognate sgRNA harbors an inactivation sequence in a non-essential region of the cognate sgRNA. In certain embodiments, introduction of the at least one Cas endonuclease and at least one cognate sgRNA (e.g., activatable sgRNA) includes integration of the Cas endonuclease and/or cognate sgRNA into the genome of the cell that is being edited or transcriptionally regulated. Accordingly, the instant system, kit and method are of use in the manipulation of endogenous genes as well as heterologous genes, A "cell" is intended to include prokaryotic and eukaryotic cells such as fungal cells® (such as yeast), plant cells, animal cells, mammalian cells and human cells. In certain embodiments, the cell is a eukaryotic cell. Depending on the Cas protein selected, genome editing and modulation of transcription can include insertions, deletions, methylations or alterations in transcription of the target nucleic acid (e.g., by dCas9 or dCas9 fusions with transcriptional repressors or activators). Alternations in transcription include suppression of transcription, activation or increase in transcription, which can be facilitated by selection of a suitable Cas9 protein, e.g., a fusion protein with repressors or activators or use of sequentially activated activatable sgRNA (see, e.g., Examples 8, 10 and 12). In certain embodiments, the Cas protein of the instant method is a Cas9 endonuclease. In other embodiments, the expression of the Cas endonuclease, cognate sgRNA or Cas endonuclease and cognate sgRNA are controlled by one or more regulatable promoters described herein, e.g. cell cycle, tissue-specific, chemically or environmentally regulatable promoters. In embodiments relating to the use of cell cycle regulatable promoters to modulate the expression of an sgRNA, it is preferable that the sgRNA is flanked by two cis-acting ribozymes to allow for proper synthesis of the sgRNA.

In some aspects of the method, the cognate sgRNA targets a transcribed strand of the nucleic acid sequence of the genome. In other embodiments, the cognate sgRNA is inserted or embedded in nucleic acids encoding a 5'- or 3'-untranslated region (UTR) of a heterologous or endogenous gene of interest. When introduced into a 5'-UTR or 3'-UTR, the inserted sgRNA preferably does not disrupt gene expression (i.e., transcription) or function of the protein encoded by the gene. Insertion of an activatable sgRNA into the UTR of a heterologous or endogenous gene provides for the expression of said gene as well as the presence of a functional or non-functional activatable sgRNA. In this respect, the instant invention links Cas9 activity to the expression of the gene the sgRNA is embedded within. In particular embodiments, the inactivation sequence of the cognate sgRNA is a cis-acting ribozyme, e.g., encoded by a nucleic acid molecule of SEQ ID NO:2, SEQ ID NO:3 or SEQ ID NO:4. In particular embodiments, the cognate sgRNA is encoded by a nucleic acid molecule of SEQ ID NO:14, SEQ ID NO:15, SEQ ID NO:16, SEQ ID NO:17, SEQ ID NO:18, SEQ ID NO:19, SEQ ID NO:20, SEQ ID NO:21 or SEQ ID NO:22.

In other aspects of the method, at least two cognate sgRNAs that target two or more sequences in the genome are introduced or deliver to the cell. In one embodiment, the at least two activatable sgRNA are sequentially activated to introduce two or more edits in the genome (see, e.g., Example 7). In another embodiment, a first activatable sgRNA of the at least two activatable sgRNA is targeted to the DNA encoding a second activatable sgRNA, so that upon activation the second sgRNA modulates transcription of a gene of interest, e.g., by binding to the promoter (see, e.g., Examples 8, 10 and 12).

The method of this invention can be used to edit or regulate transcription within the genome of a cell for a variety of reasons including, e.g., enhanced biotherapeutics production in eukaryotic cells, enhanced commodity chemical production in prokaryotic or eukaryotic cells, gene drives in organisms or cell cultures, in vivo or ex vivo gene therapy, ex vivo cell transfection for diagnostics or research, ex vivo cellular differentiation, and production of transgenic organisms. In a preferred embodiment, cells are isolated from the subject organism, transfected with an sgRNA and Cas protein or nucleic acids (gene or cDNA) encoding an sgRNA and Cas protein, and re-infused back into the subject organism (e.g., a patient). Various cell types suitable for ex vivo transfection are well known to those of skill in the art. In another embodiment, the isolated cells are subject to genomic integration (e.g., Cas9-mediated HDR or lentiviral transduction) of the described invention wherein the integrated DNA encodes a program to control cellular behavior either outside or once inside of the organism.

When used for the production of transgenic animals, the instant method can include the development of transgenic animals as disease models, as well as animals with desirable traits. Embryos may be treated using the methods and compositions of the invention to develop transgenic animals. In some embodiments, suitable embryos may include embryos from small mammals (e.g., rodents, rabbits, etc.), companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. In other embodiments, suitable embryos may include embryos from fish, reptiles, amphibians, or birds. Alternatively, suitable embryos may be insect embryos, for instance, a Drosophila embryo or a mosquito embryo.

Transgenic organisms contemplated by the methods and compositions of this invention also include transgenic plants and seeds. Examples of suitable transgenes for introduction include exogenous nucleic acid molecules encoding one or more functional polypeptides or RNA, with or without one or more promoters, which impart desirable traits to the organism. Such traits in plants include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; standability; starch, oil, or protein quantity and/or quality; amino acid composition; and the like. Of course, any two or more exogenous nucleic acids of any description, such as those conferring herbicide, insect, disease or drought resistance, male sterility, prolificacy, starch properties, oil quantity and quality, or those increasing yield or nutritional quality may be employed as desired.

The following non-limiting examples are provided to further illustrate the present invention.

Example 1: Cas9 Fusion Proteins

Materials and Methods

Recombinant Cas9 Purification. Cas9 (pMJ806, Addgene) was expressed and purified by a combination of affinity, ion exchange and size exclusion chromatographic steps according to conventional methods (Anders & Jinek (2014) *Methods Enzymol.* 546:1-20).

sgRNA Plasmids and RNA Generation. All sgRNAs were cloned into pSPgRNA (Addgene). RNA was generated via PCR-mediated fusion of the T7 RNA polymerase (RNAP) promoter to the 5' end of the sgRNA sequence. The column-purified PCR products were used as transcription templates in reactions containing 5.0 µg/ml purified recombinant T7 RNAP and 1x transcription buffer: 40 mM Tris (pH8.0), 2 mM spermidine, 10 mM $MgCl_2$, 5 mM DTT, and 2.5 mM rNTPs. Reactions were treated with DNase I and purified using the RNA Clean & Concentrator™ Kit (Zymo Research).

Generation of Cas9 Variant Constructs and Ctnnb1:: EGFP Donor DNA. Nucleotide sequences encoding Cdt1 and Geminin were ordered as gBlock gene fragments (IDT), which were fused to 3'-end of the nucleotide sequences encoding Cas9 (Addgene) using GIBSON ASSEMBLY® (NEB). Nucleic acids encoding the resulting Cas9-Cdt1 and Cas9-Gem fusion proteins are set forth herein in SEQ ID NO:67 and SEQ ID NO:68, respectively. Nucleic acids encoding the Cas9-Cdt1 and Cas9-Gem fusion proteins were respectively inserted downstream of the mouse cyclin B and mouse cyclin E promoters (see SEQ ID NO:69 and SEQ ID NO:70, respectively). The amino acid sequences of the Cas9-Cdt1 and Cas9-Gem fusion proteins are set forth in SEQ ID NO:71 and SEQ ID NO:72, respectively. The Ctnnb1::EGFP donor DNA was generated through PCR amplification of the Ctnnb1::EGFP locus (Shy, et al. (2016) *Nucl. Acids Res.* 44(16):7997-8010) to include 500 bp homology arms. The PCR product was TA cloned and the sequence was verified.

Cell Culture. Mouse embryonic stem (ES) cells: for normal passage of wild-type, Rex1:EGFPd2, or Rosa26:: TetOn-Otx2-mCherry ES cells, single-cell suspensions of 1-2×10$^6$ C57BL/6 mouse ES cells were plated onto 10-cm dishes previously coated with 0.1% gelatin (Millipore). Cells were grown in KnockOut™ Dulbecco's Modified Eagle Medium (DMEM; GIBCO) supplemented with the following: 15% KnockOut™ Serum Replacement (GIBCO), 2 mM L-Glutamine (GIBCO), 1000 U/ml Pen Strep (GIBCO), 1 mM HEPES (Thermo Scientific), 1X MEM Non-Essential Amino Acids (GIBCO), 55 µM 2-mercaptoethanol (GIBCO), 100 U/ml LIF (Millipore), and 3 µM CHIR99021 (Glycogen synthase kinase 3 inhibitor, Sigma). Cells were split 1:10 with 0.25% trypsin-EDTA (GIBCO) every 2-3 days. HEK293 and Neuro2a:HEK293 cells are known in the art. All cells were maintained in DMEM supplemented with 10% fetal bovine serum (FBS; Sigma) and 100 µg/mL Penicillin-Streptomycin. Cell line identity of HEK293 was verified by deep sequencing.

Transfection and Selection Conditions. For ES cells, 1×10$^5$ cells were transfected shortly after being plating in 12-well dishes for about 18 hours. For each well, 5 µl of Lipofectamine™ 2000 and relevant DNAs were incubated in 250 µl OPTI-MEMm (GIBCO). Where appropriate, transfections included 250 ng pPGKpuro (Addgene) to allow for elimination of non-transfected cells. In addition, cells were transfected with 250 ng pX330 Cas9 (wild-type or variant) expression plasmid and 250 ng corresponding pSPgRNA plasmid. For the Ctnnb1::EGFP assay, an additional 400 ng of Ctnnb1::EGFP plasmid was added and after 48 hours cells were split into 2 µg/ml puromycin and selection was applied for 48 hours.

For Neuro2a cells, 0.5×10$^5$ cells were plated the night before transfection in 6-well dishes. For each well, 6 µl of Lipofectamine™ 2000 and relevant DNAs were incubated in 500 µl OPTI-MEM™ (GIBCO) before adding to wells. The Ctnnb1::EGFP assay contained 400 ng Cas9 expression plasmid, 400 ng corresponding pSPgRNA. plasmid, 400 ng pPGKpuro to allow for elimination of non-transfected cells, and 800 ng Ctnnb1::EGFP plasmid. After 48 hours, cells were split into 4 µg/ml puromycin and selection was applied for 96 hours.

For HEK293 cells, 0.5×10$^5$ cells were plated the night before transfection in 6-well dishes. For each well, 6 µl of Lipofectamine™ 2000 and relevant DNAs were incubated in 500 µl OPTI-MEM™ (GIBCO) before adding to wells. All transfections contained 1 µg Cas9 expression plasmid, and 1 µg corresponding pSPgRNA plasmid. For deep sequencing noise controls, cells were transfected with an empty pSPgRNA plasmid.

T7 Endonuclease I Assays. Editing was monitored by T7 Endonuclease I (T7E1) or restriction enzyme digestion. Briefly, edited mouse embryonic stem cells (mESCs) were harvested 36 hours after transfection and genomic DNA was extracted using Bradley lysis buffer with proteinase K, followed by EtOH/NaCl-mediated precipitation and subsequent EtOH washes. Genomic DNA (50 ng) was used as a template in a PCR reaction using PHUSION® high GC buffer (NEB) and standard PCR conditions (98° C. for 30 seconds, 30 cycles of 98° C. for 5 seconds, 64° C. for 10 seconds and 72° C. for 15 seconds, and one cycle of 72° C. for 5 minutes). Aliquots (200 ng) of purified PCR DNA were subjected to T7EI and resolved on a 1.5% agarose gel. Gel images were quantified using ImageJ.

Flow Cytometry. Single-cell suspensions were prepared by trypsinization and re-suspension in 2% FBS/PBS/2 mM EDTA. Cells were analyzed on a LSRFortessa™ flow cytometer. Data analysis was performed using FlowJo v9.3.2. Live cells were gated by forward scatter and side scatter area, singlets were gated by side scatter area and side scatter width. At least 5×10$^5$ singlet, live cells were counted for each sample (higher counts for more infrequent events). Green fluorescence events were quantified by gating the appropriate channel using fluorescence negative cells as control. Cells used in the Ctnnb1::EGFP assay were subject to flow cytometry one week after transfection. Cells used in the Rex1::EGFPd2 disruption assay were subject to flow cytometry 40 hours after transfection.

Western Blotting and Immunofluorescence. For western blot analysis, Neuro2a, HEK293, and mESC were transfected with Cas9 plasmids in equimolar concentrations respectively, and lysates were generated 48 hours after transfection. FLAG®-tagged Cas9 was detected using an aFLAG® antibody (Sigma).

For immunofluorescence, Neuro2a cells were co-transfected with respective Cas9 and mCherry expression plasmids onto 18-mm glass discs. Forty-eight hours after transfection, cells were fixed and permeabilized with 4% paraformaldehyde at room temperature for 10 minutes. Cells were then blocked with 0.3% TRITON™ X-100, 2% FBS, and 1% bovine serum albumin (BSA) for 45 minutes at room temperature. Cas9 was probed with a 1:3000 dilution of aFLAG® antibody, endogenous Cdt1 was probed with a 1:1000 dilution of aCdt1 antibody (Abcam), and endogenous Geminin was probed with a 1:500 dilution of αGeminin antibody (Proteintech). All antibodies were dilution in blocking buffer and incubated overnight at 4° C. Cells were then probed with αMouse-FITC-conjugated secondary antibody for Cas9 detection, and Cdt1/Gem was probed with αRabbit-cy5 conjugate for 45 minutes at room temperature. Cells were then washed 3X, with the second wash containing 300 nM DAPI. Cells were then mounted and imaged on a Zeiss LSM 710 confocal microscope.

Expression and Analysis of Cas9-Degron Fusion Proteins

Degron-tagged, destabilized Cas9 variants have been suggested (Gutschner, et al. (2016) Cell Rep. 14:1555-1566; Maji, et al. (2017) *Nat. Chem. Biol.* 13:9-11; Howden, et al. (2016) *Stem Cell Rep.* 7:508-517). However, these tagged Cas9 variants have been tested for use in inactivating Cas9 rather than stimulating genome editing. To assess whether destabilizing the Cas9 protein could reduce the rate-limiting dissociation step for genome editing, degrons from Cdt1 (target of SCF$^{SkP2}$) and Geminin (target of APC$^{Cdh1}$) were used as cell cycle sensors (Tada (2007) Front. Biosci. 12:1629-41). In addition to being sensors, Cdt1 and Geminin are active in the nucleus thereby enabling active Cas9 to enter the nucleus before being degraded. Indeed, expression of the Cas9Cdt1 and Cas9Gem fusion proteins demonstrated that Cas9 fusion protein levels fluctuated throughout the different phases of the cell cycle when examined through immunofluorescence. Furthermore, western blot analysis revealed that protein levels were different amongst the variants as a result of destabilization and/or cell cycle regulated promoter.

To assess genome editing, mouse embryonic stem (ES) cells were initially used because of their rapid oscillations through the cell cycle with minimal effects based on cell-cycle phase specificity (Ballabeni, et al, (2011) *Proc. Natl. Acad. Sci.* USA 108:19252-7). Destabilized Cas9 fusion proteins were expressed at lower levels than untagged Cas9. However, destabilized Cas9 fusion proteins more effectively generated indel mutations when targeted to EGFP in Rex1: EGFPd2 of ES cells. Destabilizing Cas9 also increased mutagenesis using the non-template sgRNA (sgm3) targeting mCherry, supporting a conclusion that Cas9 destabilization overcomes the rate-limiting dissociation step for genome editing.

To test whether cell cycle regulation and destabilization of Cas9 during S/G2 phases of the cell cycle could increase HDR-mediated editing, constitutively expressed (promoter: Cbh) Cas9Gem, Cas9Cdt1 and cell cycle promoter (Cycline E or B) controlled Cas9Gem, Cas9Cdt1 and WT-Cas9 were compared to constitutively expressed WT-Cas9 for generating on-target insertion of EGFP into the Ctnnb1 gene (Shy, et al. (2016) *Nucl. Acids Res.* 44(16):7997-8010) as well as on target mutations (indels). mESC were transfected with the respective Cas9 construct (FIG. 1) and a template or non-template targeted sgRNA. HDR and indel frequencies were analyzed at 48, 84 and 156 hours after transfection via flow cytometry or targeted deep sequencing, respectively (FIG. 1). Cbh-WTCas9 exhibited a template strand bias for HDR consistent over all time-points. Complementary indel data from this condition shows that template and non-template perform similarly, suggesting that the observed template strand bias in HDR is not a result of a poorly performing non-template sgRNA. Cbh-Cas9Cdt1 alleviated the HDR template strand bias, and indel data shows that this variant enhanced the activity of the non-template sgRNA. This decreased HDR was observed for CyclinB-Cas9Cdt1, which is expressed and renders Cas9 exclusively destabilized. These two findings suggest that destabilization by the Cdt1 variant may reduce HDR frequencies as a result of increased indel frequencies. Interestingly, CyclinE-CasCdt1 expressed Cas9 when it is stabilized during G1, but then abruptly destabilized in S phase before expression is halted. This characteristic led to the highest HDR frequencies observed for the non-template sgRNA, suggesting that timing of expression is critical. Furthermore, expression of Cas9Gem by Cyclin E rendered the highest HDR frequencies for the template sgRNA, and greatly reduced for the non-template. Indel data for this variant are the lowest amongst the variants, suggesting that expression of Cas9Gem when it is destabilized during G1 and then stabilized briefly in S phase is advantageous for increasing the ratio of HDR:indel. Lastly, expression of CasGem during the S/G2 phases by the Cyclin B promoter increases HDR frequencies by the non-template sgRNA to outperform WT-Cas9. These findings demonstrate that cell cycle regulated transcription and Cas9 stabilization reduces protein levels and can increase HDR levels while reducing on target indel accumulation. Furthermore, the destabilization of Cas9, as demonstrated with the Cdt1 variant, increases the activity of non-template sgRNA to alleviate the template strand bias.

Figure 2:
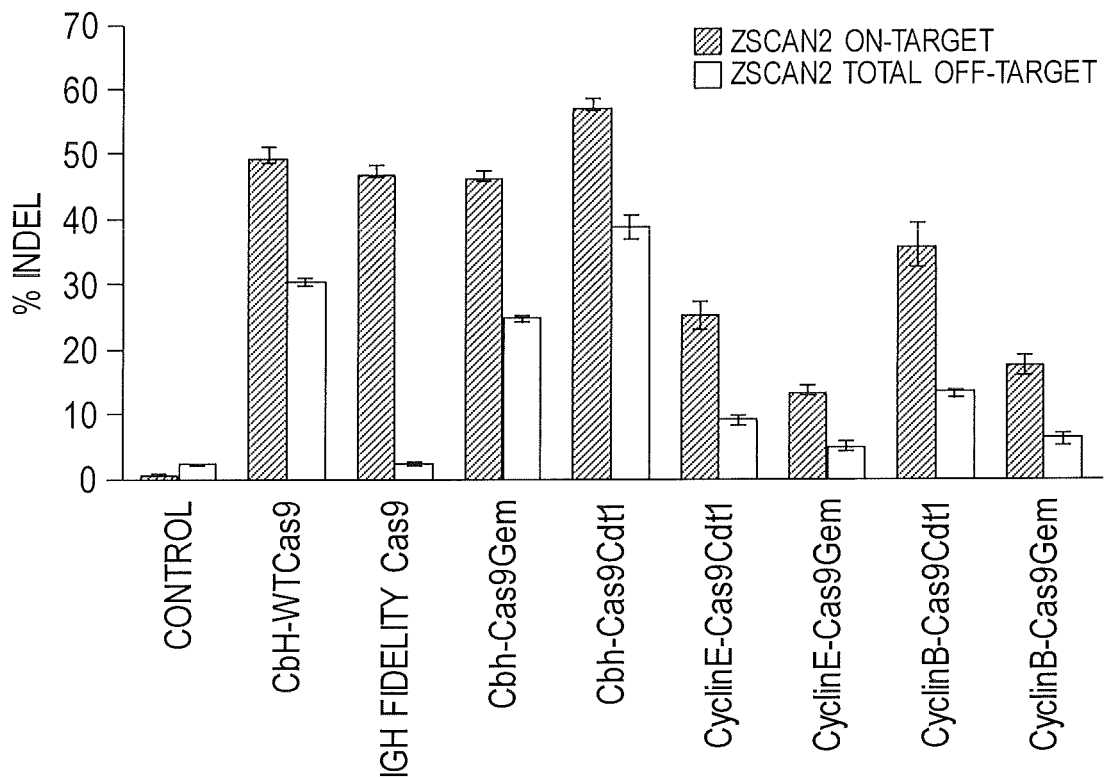
FIG. 2 shows on-target and combined off-target mutation frequencies caused by Cas9 variants using two promiscuous sgRNAs in HEK293 cells.

Increasing the frequency Cas9 DSB could potentially result in increased off-target mutations. To test this possibility, sgRNA with off-target activities were used. This analysis used sgRNA targeted to sites in the endogenous EMX1 and ZSCAN2 genes, which have been previously characterized by GUIDE-seq (Kleinstiver, et al. (2016) *Nature* 529(7487):490-5). On-target and off-target mutations were measured in HEK293 cells by deep sequencing PCR amplicons from genomic DNA of transfected cells. Both destabilized Cas9 fusion proteins displayed reduced off-target mutations for the EMX1 sgRNA (FIG. 2). For the ZSCAN2 sgRNA, Cbh-Cas9Cdt1 displayed increased on-target and off-target mutations, and Cbh-Cas9Gem displayed reduced off-target mutations (FIG. 2). Thus, destabilization did not demonstrably increase off-target mutagenesis and actually decreased it for most of the well-characterized sites examined. Off-target nuclease activity at lower-affinity sites in the genome has been associated with high levels of Cas9 expression. The data presented herein indicates that destabilized Cas9 variants do not increase off-target activity, because reducing Cas9 levels in cells reduces the frequency of binding at low-affinity, off-target sites.

Together, the findings herein demonstrate the importance of the genome in the process of genome editing and show how activity at target sites can affect the rate limiting step in genome editing procedures. Sites where Cas9 is not dislodged from the DSB are mutated less frequently in these experiments, and can be predicted by RNA Pol II translocation through a site. When targets sites reside within genes that are expressed in the cell used for genome editing or necessitate an sgRNA that targets the non-template strand, destabilization of Cas9 can increase efficiency of genome editing. For experiments requiring rapid genome editing outcomes, use of destabilized Cas9 variants can decrease the time needed for iterations of break-and-repair cycles, increasing mutagenesis at target sites. Combining the cell cycle-specific destabilization with cell cycle specific expression offers the potential to target genome editing to specific points in the cell cycle.

Exemplary ubiquitin-dependent destabilized Cas9 fusion proteins include, but are not limited to, Cas9-Cdt1 (SEQ ID NO:71) and Cas9-Gem (SEQ ID NO:72) fusion proteins. It is also contemplated that ubiquitin-independent degrons can also be used including, e.g., the PEST sequence from mouse ornithine decarboxylase (MODC), which is known to reduce the half-life of GFP by introduction of these additional proteolytic signals. Cas9-PEST fusion proteins are set forth herein in SEQ ID NO:73, SEQ ID NO:74 and SEQ ID NO:75.

Example 2: Ribozyme-Mediated Inactivation of CRISPR sgRNAs

Figure 4:
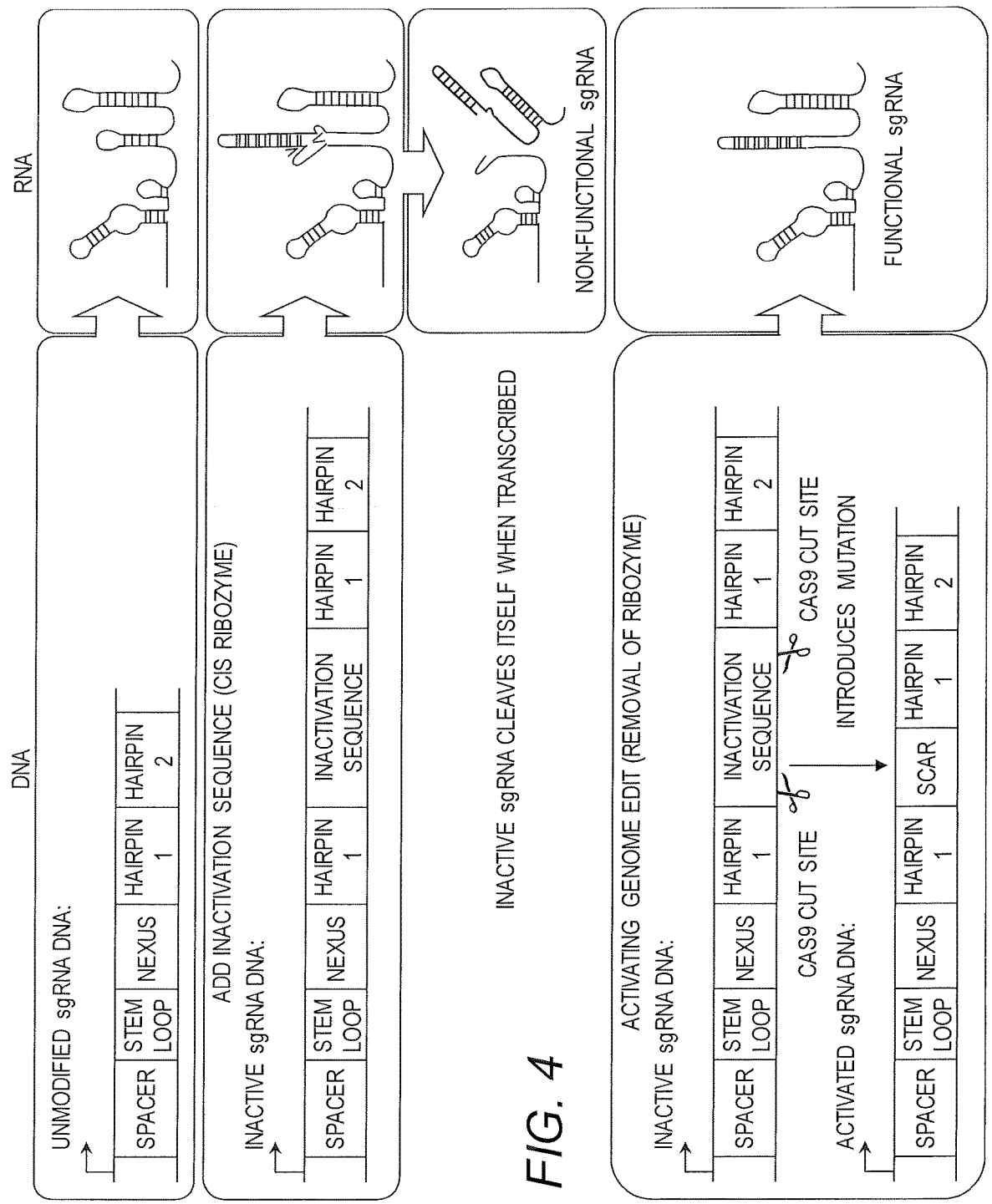
FIG. 4 is a schematic depicting an activatable sgRNA. Insertion of a cis-acting ribozyme sequence into hairpin 1 results in cleavage of the sgRNA upon transcription. The DNA sequence either flanking or encoding the ribozyme is then targeted by Cas9 to introduce a mutation to disrupt its cis-cleavage activities and restore sgRNA functionality.

The sgRNA of *Streptococcus pyogenes* Cas9 (FIG. 3) has been extensively characterized to understand which regions of the RNA can be mutated. This analysis has indicated that whereas the bulge and *nexus* regions of the sgRNA are the most critical features for Cas9 targeting, hairpin 1, hairpin 2, and the upper and lower stem loop regions are relatively tolerant to sequence variations, including nucleotide substitutions, insertions and deletions and even predicted structural disruptions (Briner, et al. (2014) *Mol. Cell* 56(2):333-339). To demonstrate that an sgRNA could be activated by a cis-acting ribozyme, the hairpin 1 module of the sgRNA for Cas9 was selected. Hairpin 1 of the sgRNA was of particular interest for creating an activatable sgRNA for two reasons: (1) hairpin 1 is not dispensable for Cas9 function and thus can be modified to disrupt Cas9 activity and (2) hairpin 1 can handle extensive mutation so long as the base of the hairpin secondary structure is conserved. In light of these characteristics of hairpin 1, a ribozyme was inserted into the middle of hairpin 1 (FIG. 4). The ribozyme basically cleaves the sgRNA in half upon transcription. To destroy its cleavage activities while maintaining a functional hairpin 1, a mutation is introduced into the ribozyme's DNA sequence. Using this approach, three different cis-acting ribozyme-sgRNA variants were generated. Specifically, nucleic acids encoding a hammerhead ribozyme (Hammann, et al. (2012) RNA 18(5):871-85; SEQ ID NO:2), a twister ribozyme (Liu, et al. (2014) Nat. Chem. Biol. 10:739-744; SEQ ID NO:3) or a hepatitis delta virus fusion ribozyme sequence (SEQ ID NO:4) were inserted into hairpin 1 of the *S. pyogenes* sgRNA (see SEQ ID NO:5, SEQ ID NO:6 and SEQ ID NO:7, respectively). Upon in vitro transcription, each of these molecules were shown to efficiently cleave themselves.

Figure 5:
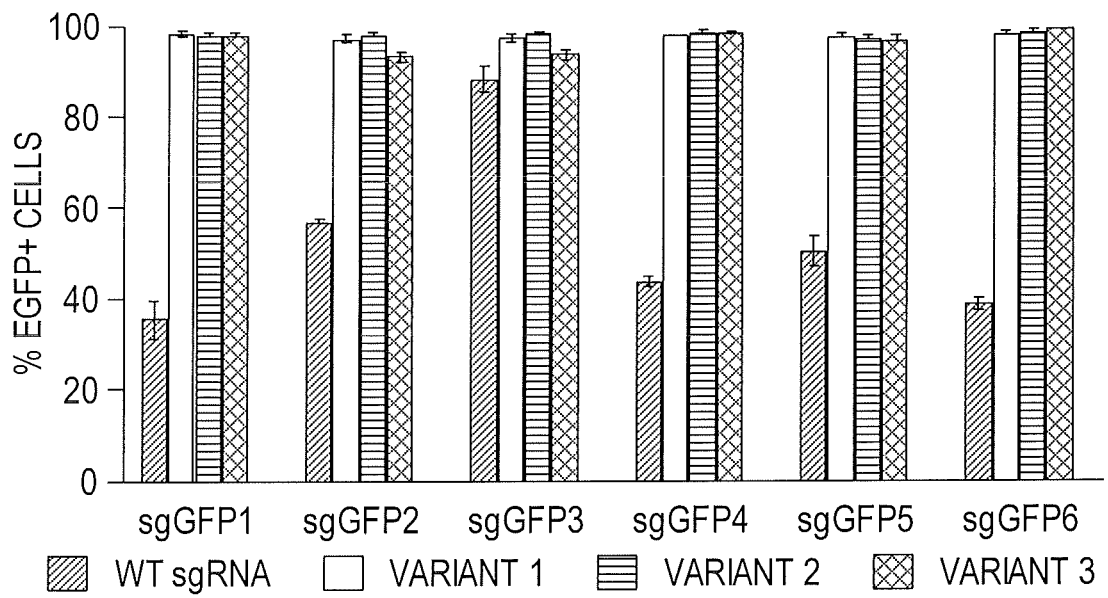
FIG. 5 shows the results of an EGFP disruption assay with activatable sgRNA variants including a ribozyme as an inactivation sequence. Variant 1, SEQ ID NO:5; Variant 2, SEQ ID NO:7; and Variant 3, SEQ ID NO:6. All three ribozyme containing variants were unable to mediate significant mutations within an EGFP transgene in mammalian cells, resulting in nearly 100% of EGFP positive cells in the actiVatable sgRNA conditions. n=3 biological replicates for all conditions which were measured by flow cytometry.

The ability for these ribozyme-sgRNA variants to facilitate Cas9-mediated mutations in live cells was subsequently tested by targeting the variants to GFP in mouse 67N cells. All three variants were targeted to six distinct sequences within GFP, and none mediated significant disruption of the gene, as measured by flow cytometry detection of GFP fluorescence (FIG. 5).

Figure 6:
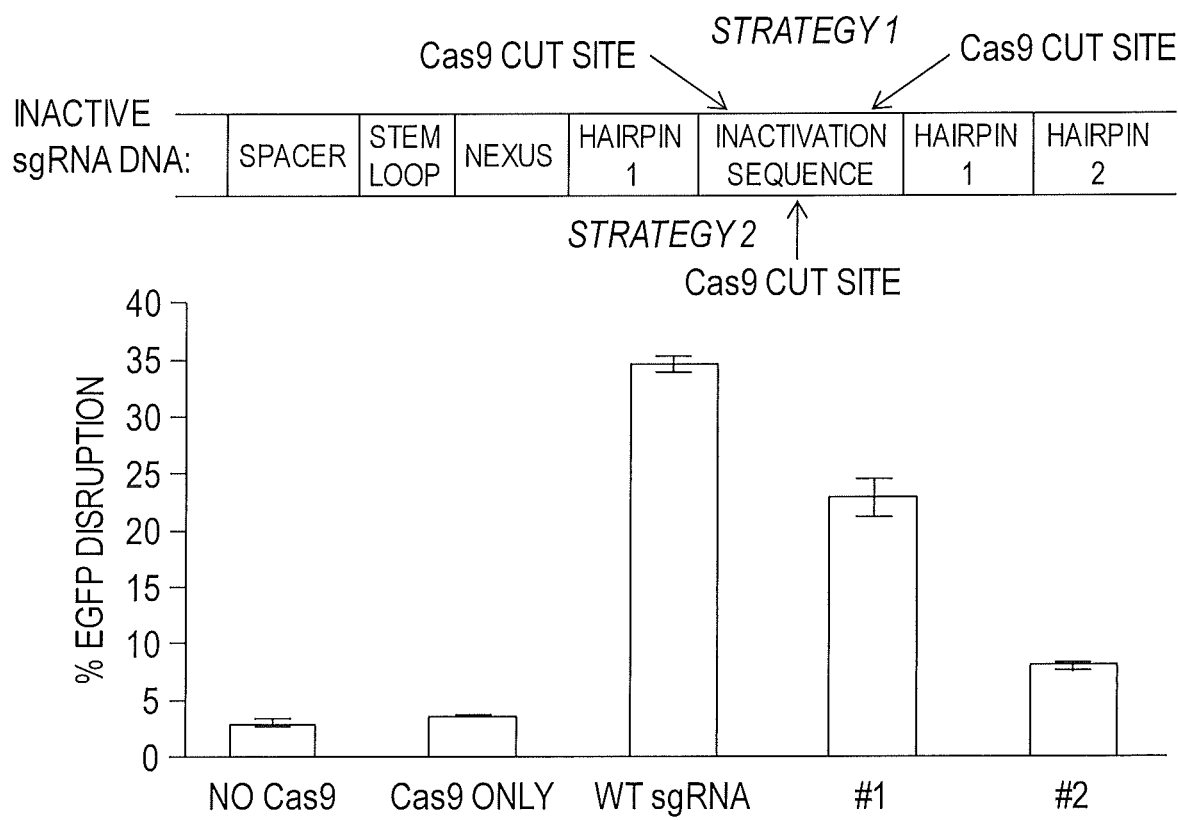
FIG. 6 is a schematic depicting two strategies for converting activatable sgRNA into functional sgRNA through mutagenesis of the ribozyme. Cell lines harboring genomic integration of variant 1 targeted to an EGFP transgene were generated, then transfections of Cas9 only or Cas9 and sgRNA targeted to excise out the entire ribozyme (strategy 1) or to mutate the ribozyme active site (strategy 2) were performed. The graph shows EGFP disruption frequencies mediated by either a wild-type sgRNA (unmodified) targeted directly to EGFP or by sgRNA targeted to the DNA of activatable sgRNA via strategy 1 or 2.

It was subsequently determined whether Cas9 recognition sites flanking or internal to the ribozyme sequence could convert an activatable sgRNA into a function sgRNA through mutagenesis of the ribozyme (FIG. 6).

Transfections of Cas9 and sgRNA targeted to excise out the entire ribozyme (strategy 1) or to mutate the ribozyme active site (strategy 2) were performed. This analysis compared EGFP disruption frequencies mediated by either a wild-type sgRNA or by strategy 1 or 2 (FIG. 6).

In light of these results, sequences encoding cis-acting ribozymes can be inserted anywhere within the sgRNA as long as the ribozyme functions to cleave the sgRNA immediately upon proper folding into its secondary structure during transcription (within seconds in the presence of $Mg^{2+}$). More specifically, nucleotides sequences encoding cis-acting ribozymes can be cloned into nonessential regions (e.g., stem loops and hairpins) of sgRNA molecules thereby serving as a means to activate the sgRNA molecules upon transcription of the same. Activatable sgRNA can be RNAs that bind any RNA-guided nuclease from, e.g., *S. pyogenes*, *S. thermophiles*, *Staphylococcus aureus*, *Francisella novicida*, *Neisseria meningitidis*, or *Brevibacillus laterosporus*, Lachnospiraceae *bacterium*, or *Acidaminococcus* sp. Like cis-acting ribozyme, it is posited that trans-acting ribozymes can be heterologously expressed and designed to target any region of the sgRNA to mediate cleavage of the sgRNA.

Examples of nucleic acid molecules encoding sgRNA variants including ribozymes inserted into nonessential regions are presented in Table 3.

TABLE 3

| sgRNA | Variant Sequence (5'->3') | SEQ ID NO: |
|---|---|---|
| SpCas9 | gttttagagctagaaatagcaagttaaaataaggctag tccgttatcaacttcgggcgcctcagatacggtcgcct gtcaccggatgtgctttccggtctgatgagtccgtgag gacgaaacaggcgattttttaacttcgggcgcctcaga tacgggcccgaagtggcaccgagtcggtgctttt | 5 |
| SpCas9 | gttttagagctagaaatagcaagttaaaataaggctag tccgttatcaacttcgggcgcctcagatacggggtgcc taacactgccaatgccggtcccaagcccggataaaagt ggaggggcatttttaacttcgggcgcctcagatacg ggcccgaagtggcaccgagtcggtgctttt | 6 |

TABLE 3-continued

| sgRNA | Variant Sequence (5'->3') | SEQ ID NO: |
|---|---|---|
| SpCas9 | gttttagagctagaaatagcaagttaaaataaggctag tccgttatcaacttcgggcgcctcagatacgggggtg cttcggatgctgatgagtccgtgaggacgaaacagggc aacctgtccatccggtatcccttttttaacttcgggcg cctcagatacgggcccgaagtggcaccgagtcggtgct tt | 7 |
| Sth CRISPR3 | gttttagagctgggtcgggcgcctcagatacggggggt gcttcggatgctgatgagtccgtgaggacgaaacaggg caacctgtccatccggtatcccaacttcgggcgcctca gatacgggcccgacccagcgagttaaaataaggcttag tccgtactcaacttgaaaaggtggcaccgattcggtgt tttt | 8 |
| Sth CRISPR3 | gttttagagctgggtacccagcgagttaaaataaggct tagtccgtactcaacttgaacgggcgcctcagatacgg ggggtgcttcggatgctgatgagtccgtgaggacgaaa cagggcaacctgtccatccggtatcccaacttcgggcg cctcagatacgggcccgaaggtggcaccgattcggtgt tttt | 9 |
| Sth CRISPR1 | gtttttgtactctggtcgggcgcctcagatacgggggg tgcttcggatgctgatgagtccgtgaggacgaaacagg gcaacctgtccatccggtatcccaacttcgggcgcctc agatacgggcccgaccagaagctacaaagataaggctt catgccgaaatcaacaccctgtcattttatggcaggtg tttt | 10 |
| Sth CRISPR1 | gtttttgtactctggtaccagaagctacaaagataagg cttcatgccgaaatcaacaccctgtcattcgggcgcct cagatacggggggtgcttcggatgctgatgagtccgtg aggacgaaacagggcaacctgtccatccggtatcccaa cttcgggcgcctcagatacgggcccgttatggcaggtg tttt | 11 |
| Sa CRISPR | gttttagtactctggaaacagaatctactaaaacaagg caacgggcgcctcagatacggtcgcctgtcaccggatg tgctttccggtctgatgagtccgtgaggacgaaacagg cgaaacttcgggcgcctcagatacgggcccgaagtggc accgagtcggtgcttttgacgaatgccgtgtttatctc gtcaacttgttggcgagatttttt | 12 |
| Sa CRISPR | gttttagtactctggaaacagaatctactaaaacaagg caagacgaatgccgtgtttatctcgtcaactcgggcgc ctcagatacggtcgcctgtcaccggatgtgcttttcgg tctgatgagtccgtgaggacgaaacaggcgaaacttcg ggcgcctcagatacgggcccgaagtggcaccgagtcgg tgcttttttgttggcgagatttttt | 13 |

Sp, *Streptococcus pyogenes*;
Sth, *Streptococcus thermophilus*;
Sa, *Staphylococcus aureus*.

Similar to ribozyme sequences, other types of inactivation target sites can be introduced into the sgRNA sequence to inactive the sgRNA. For example, steric hinderance strategies such as the addition of nucleotide sequences that cause secondary RNA structures within the sgRNA RNA molecule that inhibit Cas9 binding can be placed anywhere within or outside of the sgRNA. Furthermore, sequences that recruit RNA binding proteins which block Cas9 binding, recruit RNases, or bind endogenous/exogenous ligands/chemicals can also be placed anywhere within or outside of the sgRNA. Moreover, extrinsic RNase recruitment sequences that target RNase activity to the sgRNA can be placed anywhere within or outside of the sgRNA. Specifically, tRNA molecules can be placed within the sgRNA so that RNase P/Z acts upon the sgRNA to degrade it and render it nonfunctional for Cas9.

Cell lines containing one or more activatable sgRNA can be created through lentiviral transduction, or targeted homology directed repair to a safe harbor locus in mouse (Rosa26) or human cells (AAVS1). Mouse models are made through zygote injection of respective reagents or injection of mouse embryonic stem cells into blastocysts.

Example 3: Activatable sgRNA Array

Figure 7:
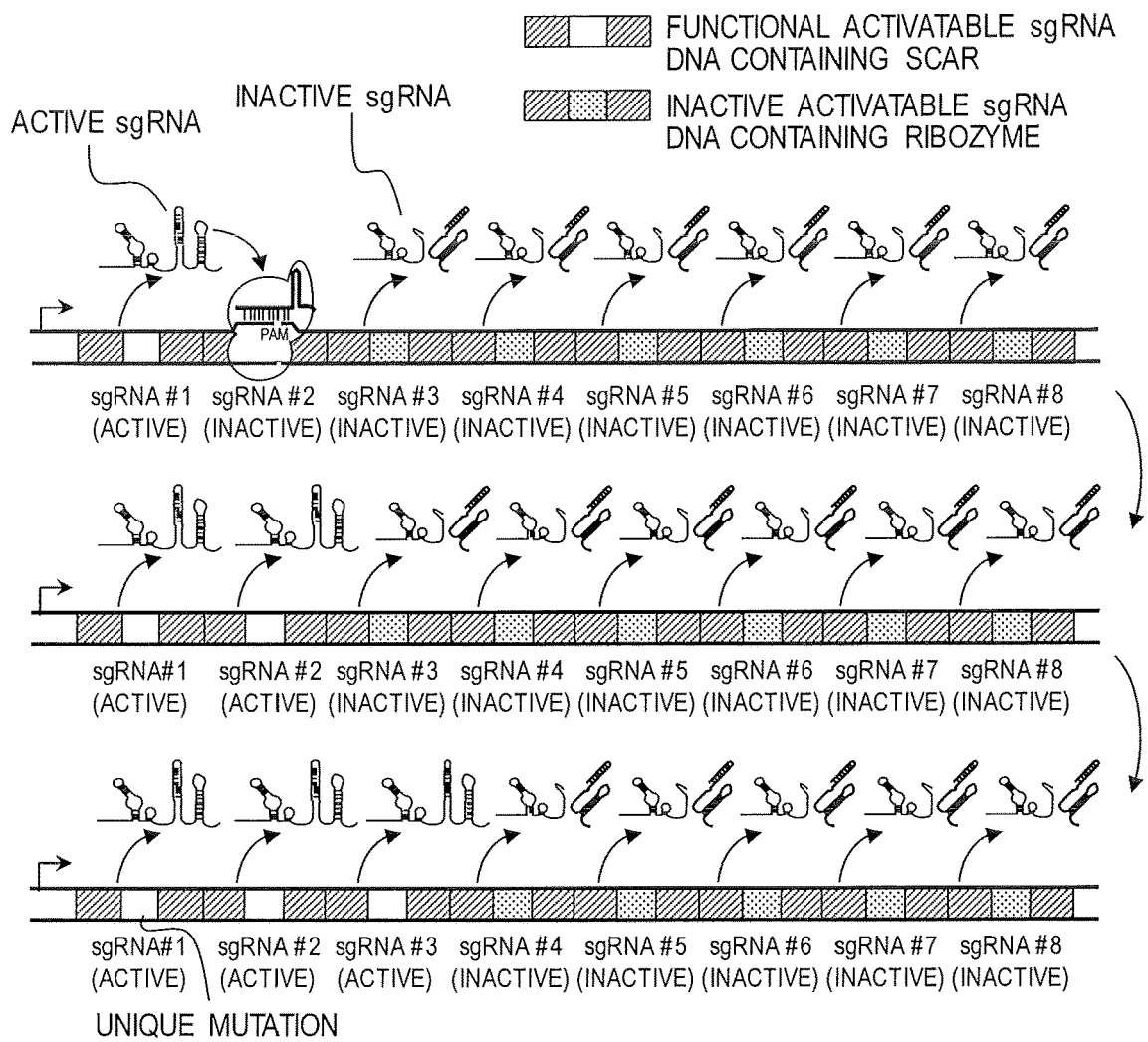
FIG. 7 is a schematic drawing depicting the sequential activation of sgRNA within an activatable sgRNA array. Each sgRNA is targeted to the sgRNA directly downstream of it rendering each sgRNA in the array dependent on the activatable sgRNA upstream of it being converted to the functional state via a genome edit. This order of events ultimately controls Cas9 activity in a sequential manner. The DNA of each activatable sgRNA can be directly analyzed by deep sequencing, or the RNA for each can be bound by oligo dT for conversion to cDNA to be analyzed via general RNA-sequencing or single cell RNA-sequencing. The process of activation of the sgRNAs within the array is a cellular barcoding process, and analysis of the mutagenic events in the array allows for lineage tree construction. These sgRNA can also have a secondary function to be targeted to the "barcode" locus depicted in FIG. 8, targeted to another activatable sgRNA as in, e.g., FIG. 9, or endogenous genes.
Figure 8:
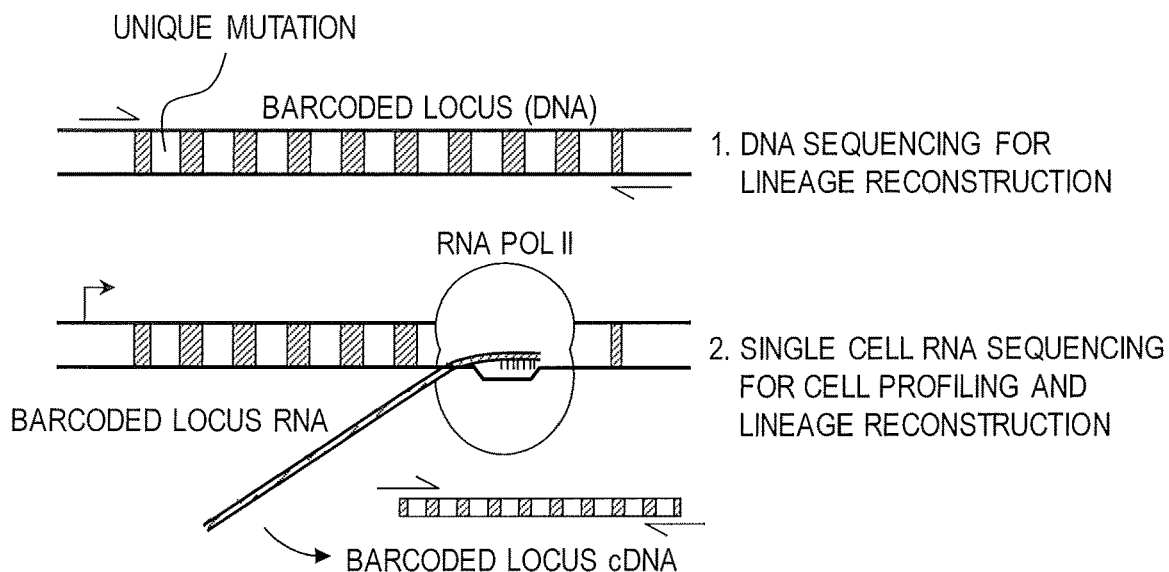
FIG. 8 provides a barcode locus schematic. The barcode locus can be amplified by PCR and analyzed via deep sequencing, or its RNA converted to cDNA for analysis via single cell RNA-sequencing.
Figure 9:
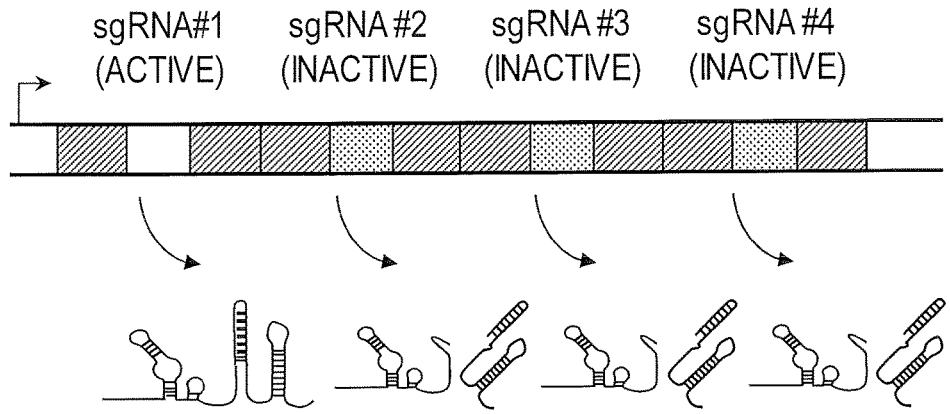
FIG. 9 depicts an array of activatable sgRNA, wherein each sgRNA targets the next for activation. sgRNA #1 has one function: to activate the next sgRNA in the array.
Figure 10:
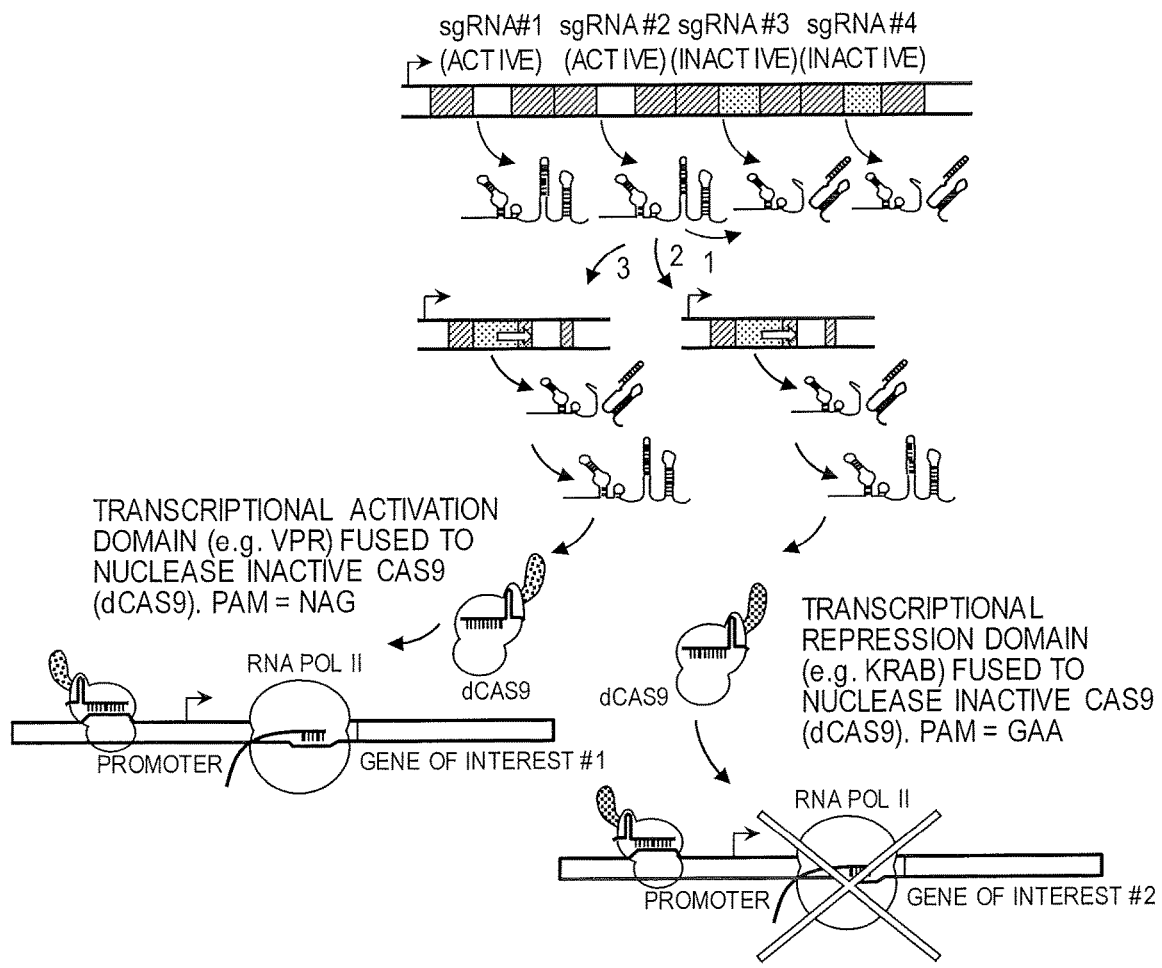
FIG. 10 depicts the array of activatable sgRNA in FIG. 9, wherein the sgRNA are programmed to execute multiple functions. Wherein sgRNA1 #1 activates sgRNA #2, sgRNA #2 has three functions and thus three targets. Function one is to target the next activatable sgRNA in the array (sgRNA #3) to continue sequential cellular barcoding, and function two and three targets the DNA of other activatable sgRNA located throughout the genome. After the activating genome edit for the second and third targets of sgRNA #2, functional activatable sgRNA are produced which bind to a dCas9 transcriptional activator or repressor that they are biochemically specific due to PAM sequence specificities. This biochemical difference in PAM recognition renders only the dCas9 molecules to be targeted to the site of interest, precluding nuclease active Cas9 from being targeted to the same sites. These sgRNAs bind dCas9 and are targeted to the promoter of an endogenous gene, wherein dCas9 recruits RNA polymerase to initiate transcription of the gene. Notably, sgRNA #2 simultaneously activates sgRNA #3, which may continue the cellular barcoding with the sole function of activating sgRNA #4.
Figure 23:
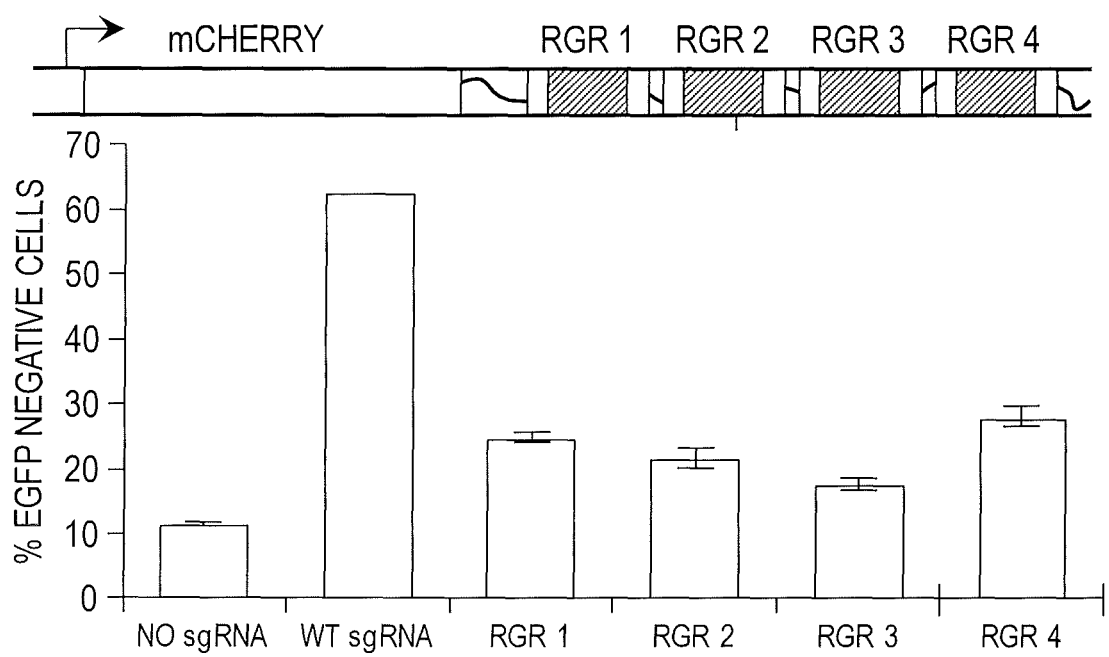
FIG. 23 shows that a series of sgRNA embedded in the 3'-UTR of a gene can be used to regulate Cas9 activity. The sgRNAs are embedded downstream of the open reading frame of a gene of interest to allow for transcription of the gene and sgRNA when the gene is expressed. The sgRNAs are placed downstream of the polyA tail and are flanked by two cis-acting ribozymes (termed RGR for ribozyme-guide-ribozyme) so that the sgRNAs are excised and yield a functional molecule for Cas9 binding. The transcript encoding the mRNA is rendered functional and can be translated due to loss of the RGR but maintenance of a proper polyA tail. Using this approach, either 1, 2, 3 or 4 RGRs were embedded in the 3'-UTR of mCherry. RGRs were targeted to an EGFP sequence within the HEK293 genome. Flow cytometry was used to measure loss of EGFP fluorescence as a readout for Cas9 activity as well as presence of mCherry, which was the coding sequence upstream of the RGRs. High levels of mCherry in EGFP negative cells confirmed translation of mRNA for which the RGRs were properly excised.

A series of activatable sgRNA are generated to contain one or more sgRNA that function to target and activate each other (FIG. 7, FIG. 9); target a "barcode" locus for genetic lineage recording; and/or target a distinct sgRNA for activation that serves to bind an RNA-guided nuclease with transcriptional purposes or targeted nuclease activity (FIG. 8, FIG. 10). A series of activatable sgRNA may be constructed to be a polycistronic array that is flanked by tRNAs and separated RNase P/Z activity or flanked by ribozymes that cleave upon transcription. The series of activatable sgRNA can also be distinct genes that are controlled by single promoters, such as U6, CMV, tetracycline response element or a cell cycle-regulated promoter. Furthermore, the sgRNA can be located within an endogenous gene and flanked by two cis-acting ribozymes so that their expression is controlled by cellular activities (FIG. 23). Activatable sgRNA expression can be under control of any RNA Pol II or RNA pol III promoter within a heterologous gene or endogenous gene.

General Barcoding of Cells with Activatable sgRNA. Barcoding uses an activatable sgRNA array in a manner that gives each activatable sgRNA at least two target sites. Target site 1 is the subsequent and inactivate sgRNA in the activatable sgRNA array, target 2 (and beyond) is the same exact target sequence but at a distinct site in the genome (FIG. 10). The distinct site may harbor target sites for many activatable sgRNA, and serves as the barcode region. The barcode is significantly smaller than the array of activatable sgRNA, allowing for next generation sequencing. The barcode may also be designed so that mutation outcomes can be influenced through strand selection described herein. Furthermore, the barcode can be located within the 3'-untranslated region of an endogenous gene or a heterologous transcribed gene, and this barcode can be incorporated into single cell RNA sequencing for simultaneous lineage tracing and transcriptional profiling (FIG. 8).

Figure 11:
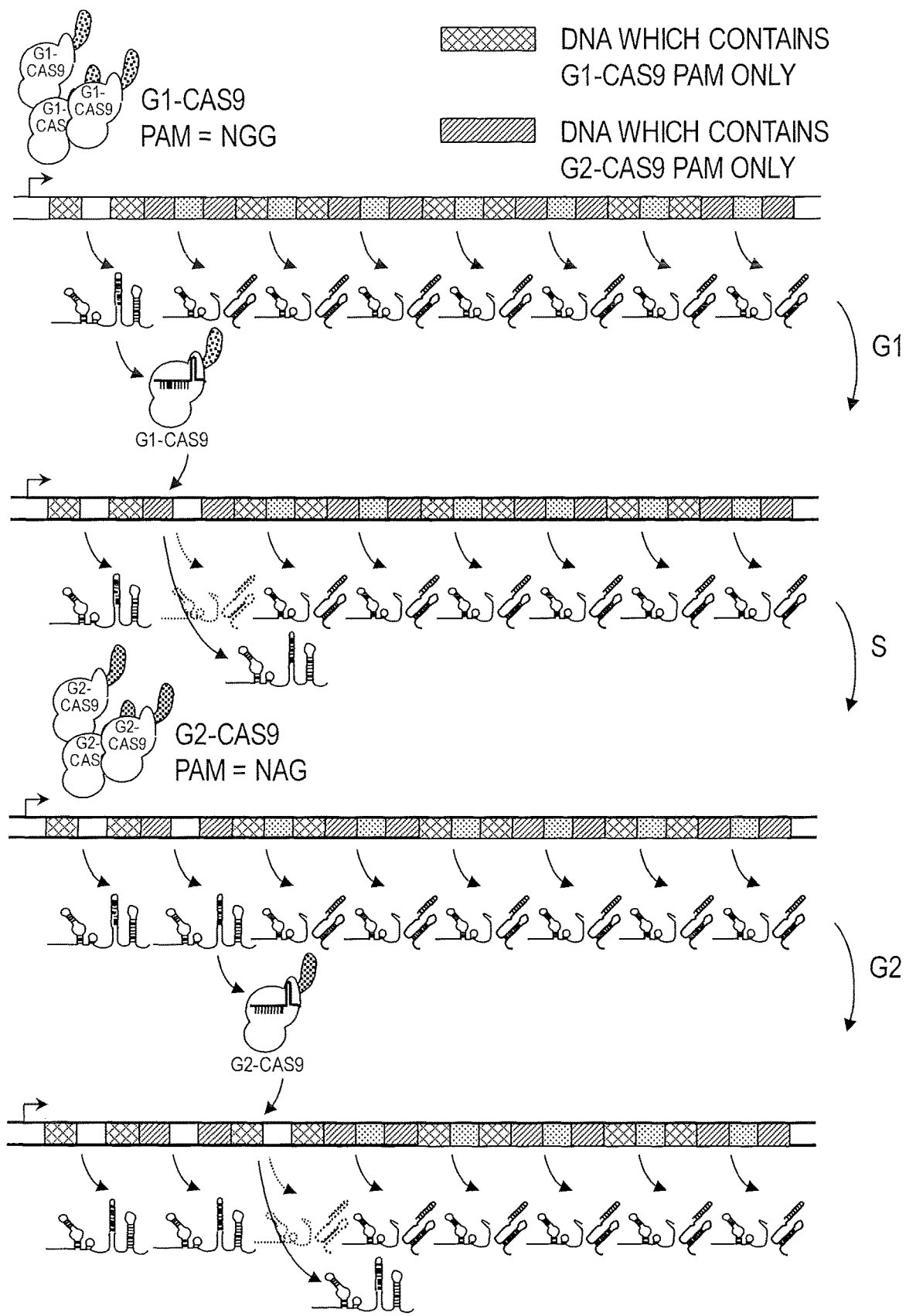
FIG. 11 depicts the use of cell cycle-controlled Cas9 nucleases to regulate the activation of activatable sgRNA array. As shown in the top section, G1-Cas9 (PAM: NGG) is present and binds to functional sgRNA. Upon binding, the Cas9:sgRNA is targeted to the next sgRNA in the array. This removes its inactivation sequence and results in expression of the functional activatable sgRNA along with a unique mutation in the sgRNA DNA array. The newly functional activatable sgRNA cannot be used by G1-Cas9, but only by G2-Cas9 due to PAM specificity requirements. As the cell progresses into G2, the G2-Cas9 (PAM: NAG) binds to functional sgRNA. G2-Cas9:sgRNA is targeted to the next sgRNA in the array, removes its inactivation sequence, and introduces a unique mutation. The newly functional sgRNA is biochemically specific for G1-Cas9 due to PAM specificity differences and is targeted to the nascent sgRNA in the array. These PAM specificity differences render the array dependent on cell cycle progression due to cell cycle regulation of the Cas9 variants and result in activation of two sgRNA per cell cycle. Furthermore, these activation processes result in two barcoding events per cell cycle.

Cell Cycle-Controlled Barcoding of Cells. Activatable sgRNA constructs from one or more species can function in a multi-regulatory cassette driven by Cas9 (or any RNA-guided nuclease), wherein the nuclease activities are regulated by the cell cycle (e.g., destabilized Cas9 controlled by cell cycle promoter element). For example, two arrays of activatable sgRNAs from two different species (e.g., *S. pyogenes* and *S. thermophilus*) can be encoded in the genome of cells that also harbor two distinct cell cycle-regulated nucleases. These nucleases can exist in opposite phases of the cell cycle so that their nuclease activities do not overlap. Each nuclease can only use an sgRNA from its species that has been activated, and each activated sgRNA will be targeted to an sgRNA of the other species. Using a similar strategy, two Cas9 nucleases regulated by the cell cycle can activate activatable sgRNA, in a single array (FIG. 11). Again, these nucleases can function in opposite phases of the cell cycle so that their nuclease activities do not overlap.

Figure 12:
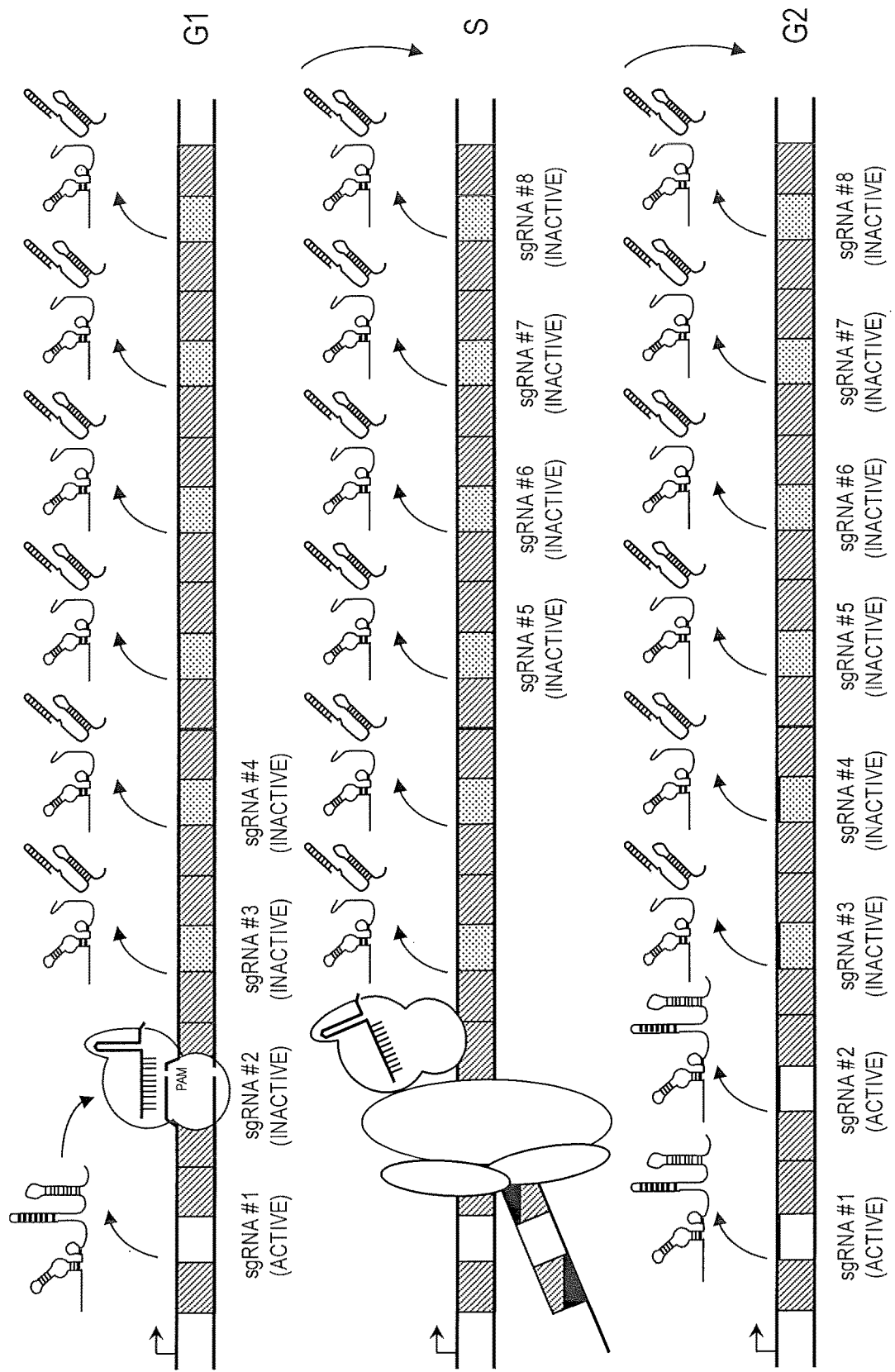
FIG. 12 is a schematic depicting utilization of strand selection to influence the number of activatable sgRNA that are activated per cell cycle. sgRNA which bind to the non-template strand will be evicted by DNA replication activities, rendering the kinetics of process dependent on the cell cycle and leading to one activating genome edit per cell cycle. Therefore, if there are ten activatable sgRNA in an array, all targeted to the non-template strand, 10 cell cycle completions are required for exhaustion of the array. sgRNA that bind to template strand will have different kinetics, depending the transcription levels of the gene, typically allowing faster activation and barcoding of the array.

Alternatively, each activatable sgRNA within an array can be targeted to the non-template strand of another inactive sgRNA in the array (FIG. 12). This targeting strategy results in Cas9 binding to the DSB until DNA replication occurs to then allow repair of the break. Because repair only begins to happen during DNA replication, the number of sgRNAs that are activated per cell cycle is substantially lowered and will most likely be one. Conversely, targeting to the template strand will allow successive, non-cell cycle influenced activation of the sgRNA array.

Figure 13:
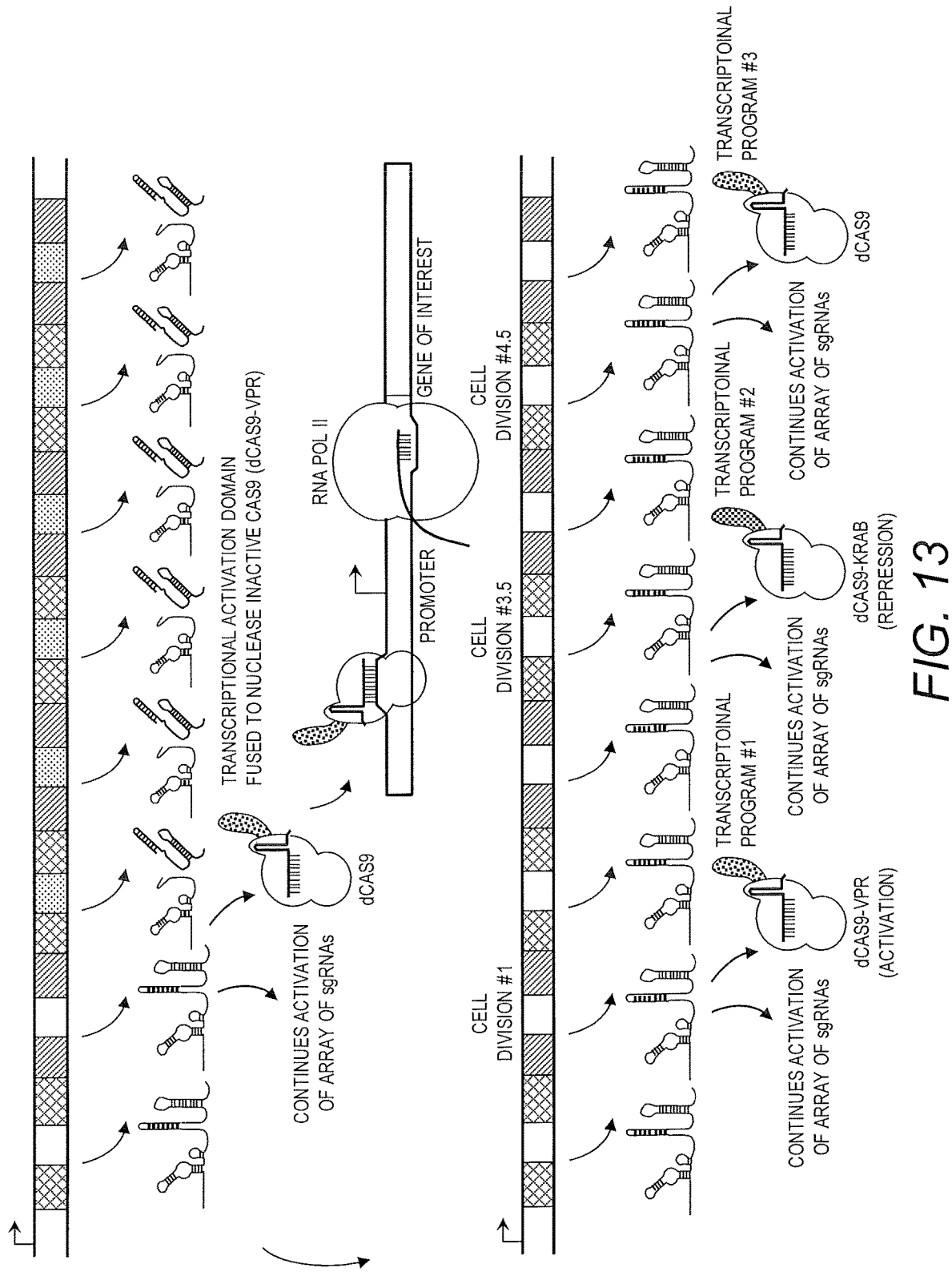
FIG. 13 provides a schematic showing the programming of an array of activatable sgRNA for controlled transcriptional, regulation after specific cell division numbers through combining processes shown in FIG. 11 or FIG. 12 with processes shown in FIG. 10. In accordance with the strategy shown in FIG. 10, activatable sgRNA control of transcription is employed. To introduce cell cycle regulation, the process further includes a cell cycle controlled activatable sgRNA array as depicted in FIG. 11.

Transcriptional Programming with Activatable sgRNA. Similar to dual functionality for the purpose of acting on the array while simultaneously barcoding, activatable sgRNA can serve to bind to and/or activate another sgRNA that functions to regulate transcriptional activity with a dCas9 activator/repressor (FIG. 13). This dual function serves to regulate transcriptional programs temporally, and incorporates RNA-guided nucleases from other species (e.g. dCas12a) in order to tightly distinguish transcriptional regulation from genome editing regulation.

Example 4: Strand Bias of Cas9 Endonucleases

Materials and Methods

Recombinant Cas9 Purification. Cas9 (pMJ806) was expressed and purified by a combination of affinity, ion exchange and size exclusion chromatographic steps by conventional methods (Anders, et al. (2015) Meth. Enzymol. 558:515-537).

sgRNA Synthesis for In Vitro Cas9-RNP. All sgRNAs were cloned into pSPgRNA (Addgene) following a protocol optimized for pX330 base plasmids (Cong, et al. (2013) *Science* 339:819-823). Templates for in vitro transcription were generated via PCR-mediated fusion of the T7 RNAP promoter to the 5' end of the sgRNA sequence using the appropriate pSPgRNA as the reaction template DNA. PCR reactions were performed using PHUSION® high GC buffer (NEB) and standard PCR conditions (98° C. for 30 seconds, 30 cycles of 98° C. for 5 seconds, 64° C. for 10 seconds and 72° C. for 15 seconds, and one cycle of 72° C. for 5 minutes). PCR products were then column-purified (Qiagen) and eluted in TE (10 mM Tris-HCl pH 8.0, 1 mM EDTA). DNA concentrations were determined using a Nanodropm 2000 (ThermoFisher Scientific), and then were diluted to 200 nM when used as templates for in vitro transcription reactions. The transcription reactions contained 5.0 µg/ml purified recombinant T7 RNAP and 1x transcription buffer (40 mM Tris-HCl pH 8.0, 2 mM spermidine, 10 mM $MgCl_2$, 5 mM DTT, 2.5 mM rNTPs). Following incubation at 37° C. for 1 hour, reactions were treated with RNase-free DNase I (ThermoFisher Scientific) and column-purified using the RNA Clean & Concentrator™ Kit (Zymo Research) following the manufacturer's protocol. The purified RNA products were eluted from the column in 15 µl of water.

DNA templates for In Vitro Cas9 Nuclease Reactions.

Linear target DNAs for hybrid digestion and transcription assays included mouse Lef1, mCherry, and GFP target DNAs, which were generated by PCR amplification using 50 ng genomic DNA from mESC Rosa26::TetON-Otx2-mCherry cells in a reaction using PHUSION® high GC buffer (NEB) and standard PCR conditions (98° C. for 30 seconds, 30 cycles of 98° C. for 5 seconds, 64° C. for 10 seconds and 72° C. for 15 seconds, and one cycle of 72° C. for 5 minutes). φNM1 genomic DNA was amplified with the same parameters, except using PHUSION®HF buffer. All PCR products were column-purified (Qiagen), eluted in TE, and concentrations were determined with a Nanodrop™ 2000 (ThermoFisher Scientific). Different segments of the mouse Lef1 gene were used in experiments testing the effects of T7 RNAP on titration of Cas9, titration of template DNA, kinetics of DSB generation, distance between the TSS and Cas9 cleavage site, template strand collisions and non-template strand collisions.

For reactions that required circular dsDNA templates (experiments testing accessibility of endonuclease or ligase enzymes), plasmid target DNAs were prepared using TOPO® TA cloning. PCR products of the previously described Lef1::PGK-neo and Ctnnb1::EGFP DNA sequences (Shy, et al. (2016) *Nucl. Acids. Res.* 44:7997-8010) were cloned into the pCR4-TOPO® Vector (ThermoFisher Scientific).

In Vitro Cas9 DSB Formation Assays. The basic Cas9 DSB formation assay was prepared in 1X Cas9 digestion buffer (40 mM Tris, pH 8.0, 10 mM $MgCl_2$, 5 mM DTT) with a final concentration of 100 nM Cas9. Prior to addition of DNA templates, sgRNA was added in molar excess, and incubated at room temperature for 10 minutes to ensure formation of the Cas9-RNP. Target DNA was added to a final concentration of 200 nM and a final reaction volume of 50 µl. Reactions were incubated at 37° C. for 25 minutes, then either heat-inactivated at 75° C. for 10 minutes or treated with Proteinase K at 37° C. for 15 minutes. DNA fragments from a portion of each reaction (approximately 15 µl) were separated by electrophoresis on a 1.5% agarose gel, and visualized with ethidium bromide staining. Percent cleavage values were determined by measuring densitometry of individual DNA bands in ImageJ, then dividing the total cleaved DNA by total DNA.

For reactions involving T7 RNAP transcription, basic Cas9 digestion conditions were applied, except 1X transcription buffer was used, unless otherwise stated. Upon addition of the target DNA, T7 RNAP was added to a final concentration of 5.0 µg/ml. Reactions were placed at 37° C. for 25 minutes, unless otherwise stated, and then heat-inactivated at 75° C. for 10 minutes. DNase-free RNase A (NEB) was added to all reactions and incubated at 37° C. for 30 minutes before separating DNA fragments on a 1.5% agarose gel.

T7 and T5 exonuclease assays were performed in 1X Cas9 digestion buffer, unless otherwise stated. T7 exonuclease assays was performed with the Lef1::PGK-Neo plasmid and digested using sgLef1. T5 exonuclease assays were performed with Ctnnb1::EGFP plasmid and digested using sgG2. T5 exonuclease assays containing T7 RNAP were performed in 1X transcription buffer. All reactions contained 100 nM Cas9:RNP, 200 nM target DNA, and 10 U of the appropriate exonuclease. Reactions were subject to Proteinase K treatment before loading onto a 1% agarose gel.

T4 DNA ligase and Cas9 digestion assays were performed in T4 DNA Ligase buffer containing ATP. Cas9-containing reactions were performed with 200 nM Cas9:RNP (sgLef1) and 100 nM Lef1:PGK-Neo plasmid. Cas9-containing reactions were allowed to incubate for 30 minutes at 37° C., then the temperature was lowered to 16° C. and 40 U of T4 DNA ligase was added. Reactions were carried out for 30 minutes and subsequently transformed into competent DH5a in 3 serial dilutions. Ampicillin-resistant colony forming units were determined following an overnight incubation at 37° C.

Cas9 hybrid digestion and transcription reactions were performed using sgm2 and by titrating an mCherry target DNA. Cleavage frequencies were measure using ImageJ. Rate (v) was calculated and plotted against substrate concentration to generate Michaelis-Menten constants.

Ku70/80 Competition Assay. Recombinant human Ku70/80 was purified by conventional methods (Hanakahi (2007) *Protein Expr. Purif.* 52:139-145). A biotinylated primer (5'-GCCTCACACGGAATCT-3'; SEQ ID NO:23) and a FITC-conjugated primer (5'-GAGAGCCCTCTCC-CAATCTTC-3'; SEQ ID NO:24) (Integrated DNA Technologies) were used to amplify a 650 bp Left target DNA, PCR products were column-purified (Qiagen), and eluted in TE. MyOne™ Dynabeads® (ThermoFisher) were prepared as described by the manufacturer to immobilize 750 ng of target DNA to about 4 µl of beads. Cas9 and sgRNA were pre-incubated in 1X Cas9 digestion buffer (40 mM Tris, pH 8.0, 10 mM $MgCl_2$, 5 mM DTT) for 30 minutes at room temperature, added to the immobilized DNA in a 5:1 molar ratio, and incubated for 25 minutes at 37° C. Control reactions without Cas9, but containing DNase, PmeI, and/or Ku70/80 were prepared simultaneously and incubated for 25 minutes at 37° C. Reactions containing Cas9 were then subjected to Proteinase K treatment or addition of excess Ku70/80, and incubated for 15 minutes at 37° C. Bead-bound DNA fragments were then collected by placing reaction tubes on a magnet, and 10 µl of the soluble fraction was transferred to a 384-well plate in technical triplicates. FITC fluorescence levels were measured using a Tecan Infinite® Pro200. Calculations were made after subtracting the background fluorescence levels of reactions lacking FITC-labeled DNA. Three independently set up reactions were performed for each reaction condition.

Cell Culture. Mouse embryonic stem (ES) cells harboring the Rex1:EGFPd2 insertion (Kalkan & Smith (2014) *Philos. Trans. R. Soc. Lond. B Biol. Sci.* 369(1657)), or a Rosa26::TetOn-Otx2-mCherry insertion (Yang, et al. (2014) *Cell Rep.* 7:1968-1981) were maintained in 10-cm dishes previously coated with 0.1% gelatin (Millipore) in KnockOut™ DMEM (GIBCO) media supplemented with 15% Knock-Out™ Serum Replacement (GIBCO), 2 mM L-Glutamine (GIBCO), 1000 U/ml Pen Strep (GIBCO), 1 mM HEPES (Thermo Scientific), 1X MEM Nonessential Amino Acids (GIBCO), 55 µM 2-mercaptoethanol (GIBCO), 100 U/ml LIF (Millipore), and 3 µM CHIR99021 (Sigma). Cell cultures were routinely split 1:10 with 0.25% trypsin-EDTA (GIBCO) every 2-3 days.

Transfection and Selection Conditions. Within 2 hours of transfections, $0.25 \times 10^5$ ES cells were freshly plated in each well of 24-well dishes. For each well, 2.5 µl of Lipofectamine 2000 and relevant DNAs were incubated in 125 µl OPTI-MEM™ (GIBCO) before adding to wells. For the Cas9 mutagenesis of 40 distinct genes in ES cells, transfections included 150 ng pPGKpuro (Addgene), 150 ng pX330 (lacking sgRNA insert), and 150 ng of the relevant pSPgRNA plasmid. To assess background mutation rate due to possible deep sequencing or amplification errors, a transfection containing pSPgRNA with empty sgRNA site was assessed alongside the other sgRNA-containing transfections. Two days after transfection, cells were split into 2 µg/ml puromycin and selection was applied for 48 hours before isolating genomic DNA by overnight lysis with Bradley Lysis buffer (10 mM Tris-HCl, 10 mM EDTA, 0.5% SDS, 10 mM NaCl) containing 1 mg/ml Proteinase K, followed by EtOH/NaCl precipitation, 2 EtOH washes, and elution in 50 µl of TE, For mCherry targeting, transfections contained the same DNA, except pSPgRNA targeted the mCherry genomic insertion, genomic DNA was isolated 48 hours after transfection in 50 µl of QuickExtract™ solution (Epicentre) for T7 Endonuclease 1 assays. Table 4 provides a listing of the sgRNA sequences, approximate distances from the predicted transcription start site (TSS) of the tetracycline response element (TRE) and computationally predicted on-target scores of sgRNA (Doench, et al. (2015) *Nat. Biotech.* 34(2):184-191).

TABLE 4

| sgRNA Name | Sequence | SEQ ID NO: | Strand | Distance from TSS | Score |
|---|---|---|---|---|---|
| sgm1 | GGAGCCGTACATGAACTGAG | 25 | Template | 365 | 74 |
| sgm2 | GGCACCAACTTCCCCTCCGA | 26 | Template | 567 | 58 |
| sgm3 | GTAATGCAGAAGAAGACCAT | 27 | Non-Template | 594 | 68 |
| sgm4 | GCCGAGGGCCGCCACTCCAC | 28 | Template | 840 | 67 |
| sgm5 | CCATGCCGCCGGTGGAGTGG | 29 | Template | 837 | 56 |
| sgm6 | CTACAACGTCAACATCAAGT | 30 | Template | 767 | 71 |
| sgm7 | CAACTTGATGTTGACGTTGT | 31 | Non-Template | 755 | 44 |
| sgm8 | TGAAGGGCGAGATCAAGCAG | 32 | Template | 661 | 68 |
| sgm9 | TCTGCTTGATCTCGCCCTTC | 33 | Non-Template | 648 | 19 |
| sgm10 | GACCCAGGACTCCTCCCTGC | 34 | Template | 512 | 51 |
| sgm11 | GAACTCGCCGTCCTGCAGGG | 35 | Non-Template | 512 | 66 |
| sgm12 | CTTGAAGCTGTCCTTCCCCG | 36 | Template | 437 | 63 |
| sgm13 | CCACTTGAAGCCCTCGGGGA | 37 | Non-Template | 437 | 53 |
| sgm14 | GAAGGGCAGGGGGCCACCCT | 38 | Non-Template | 326 | 40 |
| sgm15 | AAGCTGAAGGTGACCAAGGG | 39 | Template | 324 | 59 |
| sgm16 | GGGCGAGGGCCGCCCCTACG | 40 | Template | 287 | 51 |
| sgm17 | TCTGGGTGCCCTCGTAGGGG | 41 | Non-Template | 285 | 54 |
| sgm18 | CTCGAACTCGTGGCCGTTCA | 42 | Non-Template | 242 | 45 |
| sgm19 | CATGCGCTTCAAGGTGCACA | 43 | Template | 224 | 52 |
| sgm20 | GGATAACATGGCCATCATCA | 44 | Template | 197 | 60 |

T7 Endonuclease 1 (T7E1) Assays. Genomic DNA was used as a template in a PCR reaction using PHUSION® polymerase (NEB) and standard PCR conditions (98° C. for 30 seconds, 30 cycles of 98° C. for 5 seconds, 55° C. for 10 seconds and 72° C. for 25 seconds, and one cycle of 72° C. for 5 minutes). Column-purified (Qiagen) PCR products were prepared as 200 ng DNA in 20 µl of 1x NEBuffer 2 (NEB), denatured at 95° C. for 10 minutes, then brought down to room temperature by decreasing the temperature 1° C. per second. One half microliter of T7E1 (NEB) was added to each reaction, and allowed to incubate at 37° C. for 25 minutes. DNA fragments were separated by electrophoresis through a 1.5% agarose gel. Gel images were analyzed and indel frequencies were quantified using ImageJ. Statistical analyses were performed by generating p values for each sgRNA with a two-sample t-test to compare plus and minus doxycycline, then all p values were adjusted via Bonferroni correction in RStudio version 1.0.136.

Bioinformatic Analysis of RNA Seq vs Indel Frequencies. The source of large scale indel mutagenesis and RNA-seq data were from previously published reports (Chari, et al. (2015) Nat. Methods 12:823-826; Chavez, et al. (2016) Nat. Methods 13:563-567). Blat and bedtools command line tools (Quinlan, & Hall (2010) Bioinformatics 26:841-842) were used to classify each of the sgRNA used by Chari et al, ((2015) Nat. Methods 12:823-826) as targeting either the template or non-template gene strand. All data were merged and visualized using RStudio version 1.0.136 (package: ggplot2), allowing for the determination of the effect of FPKM and strand orientation on indel frequency. Statistical analyses and significance were determined with Multiple Comparisons of Means with Tukey contrasts (package: multcomp).

Flow Cytometry. Single-cell suspensions were prepared by trypsinization and re-suspension in 2% FBS/PBS/2 mM EDTA. Cells were analyzed on a LSRFortessa™ flow cytometer. Data analysis was performed using FlowJo v9.3.2. Live cells were gated by forward scatter and side scatter area. Singlets were gated by side scatter area and side scatter width. At least $5 \times 10^5$ singlet, live cells were counted for each sample. mCherry fluorescence events were quantified by gating the appropriate channel using fluorescence negative cells as control.

Targeted Deep-Sequencing Preparation and Analysis. Genomic DNA was harvested four days after transfection and approximately 100 ng of DNA was used in PCR to amplify respective target sites while attaching adapter sequences for subsequent barcoding steps. PCR products were analyzed via agarose gel and then distinct amplicons were pooled for each replicate respectively in equal amounts based on ImageJ quantification. Pooled PCR products were purified with AMPure beads (Agilent), and 5 ng of the purified pools was barcoded with Fluidigm Access Array™ barcodes using AccuPrime™ II (ThermoFisher Scientific) PCR mix (95° C. for 5 minutes, 8 cycles of 95° C. for 30 seconds, 60° C. for 30 seconds and 72° C. for 30 seconds, and one cycle of 72° C. for 7 minutes). Barcoded PCR products were analyzed on a 2200 TapeStation (Agilent) before and after 2 rounds of 0.6x solid phase reversible immobilization bead purification to exclude primer dimers. A final pool of amplicons was created and loaded onto an Illumina MiniSeq generating 150 bp paired-end reads.

Determination of indel frequencies made use of CRISP-Resso command line tools that demultiplexed by amplicon, where appropriate, and then determined indel frequency by alignment to reference amplicon files (Pinello, et al. (2016) Nat. Biotechnol. 34:695-697). Outputs were assembled and analyzed using custom command-line, python, and R scripts.

Generation of Spacers Targeting ONM1. Plasmids harboring Cas9, tracrRNA and single-spacer arrays targeting ONM1 were constructed via BsaI cloning onto pDB114 as described previously (Heler, et al. (2015) Nature 519:199-202). Specifically, spacers RC1 (plasmid pRH320), RC2 (pRH322), RC3 (pRH324) and RC4 (pRH326) were constructed.

φNM1 Infection Assays. Phage φNM1h1 was isolated as an escaper of CRISPR type III targeting of φNM1 with spacer 4B (Goldberg, et al. (2014) Nature 514:633-637). Plate reader growth curves of bacteria infected with phage were conducted as described previously ((Goldberg, et al. (2014) Nature 514:633-637) with minor modifications. Overnight cultures were diluted 1:100 into 2 ml of fresh BHI broth supplemented with appropriate antibiotics and 5 mM $CaCl_2$) and grown to an $OD_{600}$ of about 0.2. Immune cells carrying targeting spacers were diluted with cells lacking CRISPR-Cas in a 1:10,000 ratio and infected with either φNM1h1 or φNM1g6 at MOI 1. To produce plate reader growth curves, 200 µl of infected cultures, normalized for OD$_{600}$, were transferred to a 96-well plate in triplicate. OD$_{600}$ measurements were collected every 10 minutes for 24 hours.

Genomic Strand Selection Influences Mutation Frequencies

Biochemical and biophysical characterization of Cas9 has identified unique properties of the nuclease. The enzyme-product complex of Cas9 bound to the DNA is notably stable, with a reported 5.5-hour lifetime in vitro (Richardson, et al. (2016) Nat. Biotechnol. 34:339-344). Given that a diploid mammalian genome typically possesses only two (before DNA replication) to four (after DNA replication) on-target substrates for Cas9, it was reasoned that the Cas9 off-rate could be the rate limiting step in genome editing and that Cas9 binding prevents DSB repair. Using purified proteins, Cas9-generated DSBs were not amenable substrates for bacteriophage repair enzymes, T4 DNA ligase and T7 exonuclease, unless Cas9 was removed by heat denaturation. By measuring the release of a 3'-fluorescent tag from dsDNA molecules attached to beads via a 5'-biotin, the Cas9-generated DSB did not release DNA ends from the beads. When purified mammalian DNA end-binding proteins (complexed human Ku70/80) were added to the' immobilized DNA, Ku70/80 bound the available DNA ends and was precipitated with beads. In contrast, addition of Ku70/80 did not increase soluble fluorescence of DNA cut by Cas9, indicating that Ku70/80 could not displace Cas9 from the DSB. Thus, persistent Cas9 binding to DNA made the DSB inaccessible to other DNA end binding proteins.

In light of this analysis, it was posited that an increase in the off-rate of Cas9 after cleavage could increase genome editing efficiency. To demonstrate this, a method was needed for experimentally manipulating the off-rate of Cas9 in vivo. Therefore, several in vitro conditions were tested to find a way of removing Cas9 from the DSB. Protection of the DSB was not eliminated by salt concentration between 4 nM to 250 mM NaCl or by temperature between 4 to 59° C. By comparison, colliding T7 RNAP into Cas9 made the DSB accessible to exonuclease activity.

Figure 14:
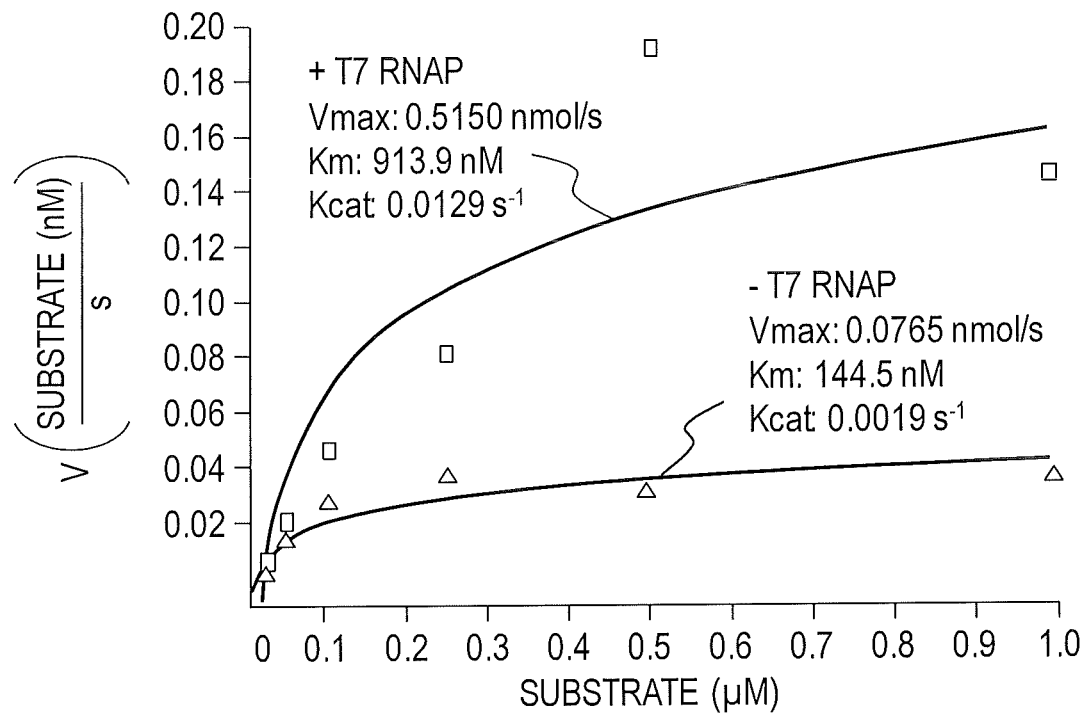
FIG. 14 shows the kinetics of Cas9 in the presence or absence of T7RNAP when Cas9 is targeted to the template (transcribed) strand. Mean kinetic values were calculated from duplicate experiments.
Figure 15:
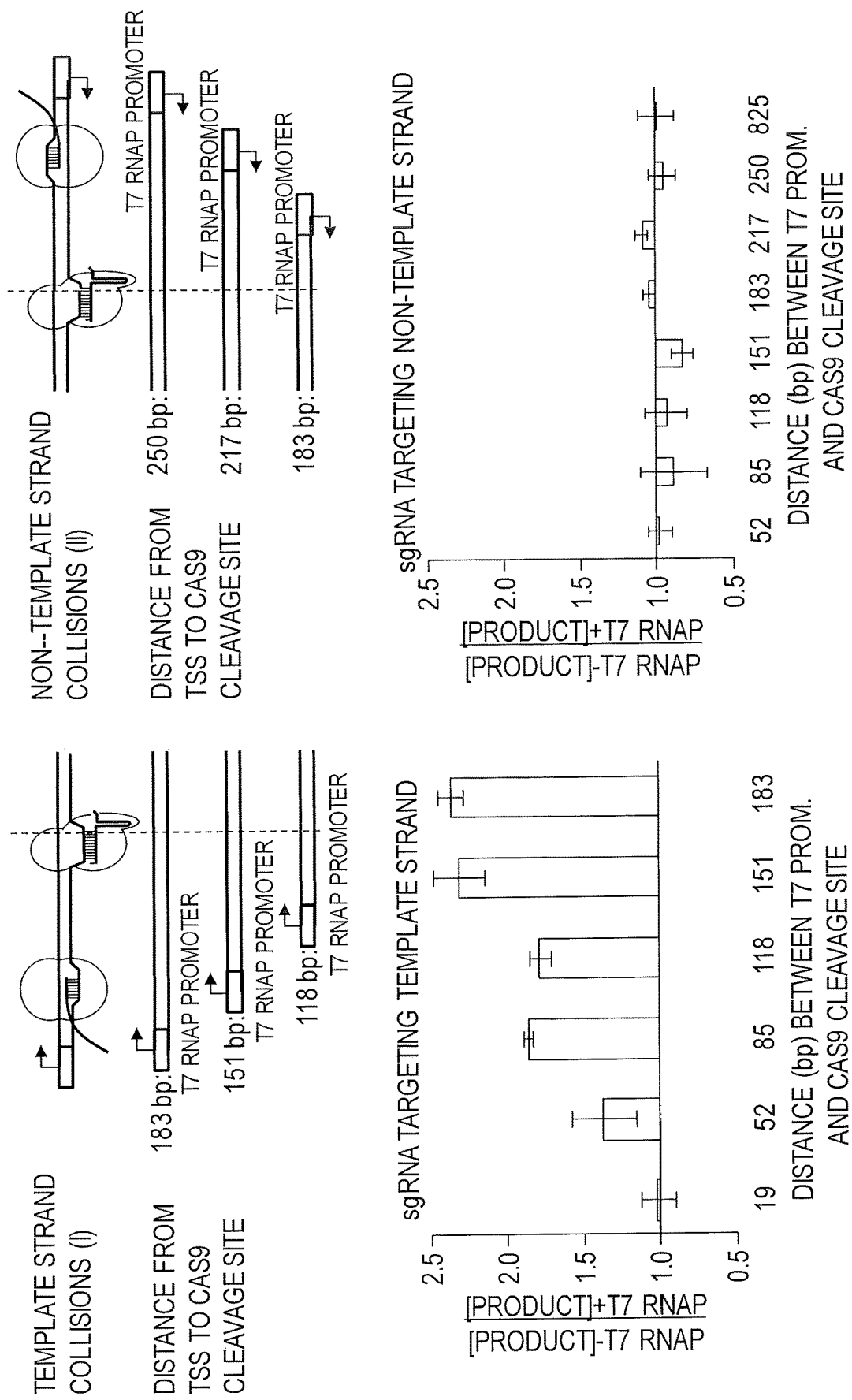
FIG. 15 shows the T7 RNAP-mediated eviction of Cas9 from DSBs is template strand and distance-dependent. Shown are the results of Cas9 digestion reactions of target DNAs harboring T7 RNAP promoters in the template-strand orientation or non-template orientation. Values represent mean±S.D. of fold change in cut DNA caused by addition of T7 RNAP, n=3.

The accessibility to the DNA end suggests that as the polymerase translocates through the sgRNA target site, the collision with Cas9 dislodges the nuclease from the DSB. Interestingly, displacing Cas9 by T7 RNAP did not eliminate nuclease activity of the dislodged Cas9 RNP molecules. Displacing Cas9 from its DSB also did not appear to stimulate an exchange or loss of the sgRNA from the Cas9 RNP. Indeed, retained nuclease activity of dislodged Cas9 RNP enabled cutting of additional DNA molecules in vitro (FIG. 14). The multi-turnover effect caused by T7 RNAP was relatively insensitive to rNTP concentration (0.125 to 2.5 µM), but its effectiveness was diminished at high substrate concentrations and when the distance between the T7 promoter and the DSB was less than 150 bp (FIG. 15).

Cas9 recognizes a short motif known as the PAM or protospacer adjacent motif in order to distinguish self from non-self. Previous biochemical analyses demonstrated an asymmetry in the freedom of DNA strands associated with Cas9 (Richardson, et al. (2016) Nat. Biotechnol. 34:339-344); the dsDNA from PAM-proximal side of Cas9 remains stably bound to Cas9, whereas the non-targeted DNA strand is released from PAM-distal side. To determine if the ability of T7 RNAP to stimulate multi-turnover nuclease activity depended on which surface of Cas9 it struck, the T7 promoter was moved to the opposite end of the linear DNA substrate. Reactions using these substrates indicated that Cas9 was refractory to T7 RNAP translocating from the PAM-proximal direction (FIG. 15). The asymmetric effect of T7 RNAP was consistent between different sgRNA (FIG. 16) and did not correlate with GC content of the sgRNA target site or GC content adjacent to the PAM. Indeed, the percent GC content of the sgRNA sequences tested lacked a strong correlation with multi-turnover Cas9 efficiency levels (Table 5; Pearson correlation: 0.36)). Accordingly, the orientation that enables multi-turnover activity is referred to herein as the "template" orientation, because Cas9 was displaced only when the sgRNA anneals to the DNA strand used as the template by RNAP.

TABLE 5

| sgRNA/spacer | Sequence + PAM | SEQ ID NO: | % GC | Fold-change* |
|---|---|---|---|---|
| RC2 | GTTCAATCTGATTTCTTTTATGG | 45 | 25 | 1.51 |
| RC1 | TAGATTGTCTAAAGTTGAGATGG | 46 | 30 | 1.51 |
| RC3 | GTTTCTAAAGGTTATCTCTTAGG | 47 | 30 | 1.46 |
| RC4 | TCGATTTCGCTATCAAATTCTGG | 48 | 35 | 1.28 |
| sgm1 | GTAATGCAGAAGAAGACCATGGG | 49 | 40 | 2.07 |
| sgm2 | TGTCCCCTCAGTTCATGTACGG | 50 | 47 | 1.50 |
| sgL1 | GCCTCAACACGAACAGAGAAAGG | 51 | 50 | 2.36 |
| sgm3 | GGAGCCGTACATGAACTGAGGG | 52 | 53 | 2.01 |
| sgG2 | TCGTGACCACCCTGACCTACGG | 53 | 58 | 1.44 |
| sgG1 | GTGAACCGCATCGAGCTGAAGGG | 54 | 59 | 1.31 |
| sgG3 | CTGAAGCACTGCACGCCGTAGG | 55 | 63 | 2.25 |

*when processive.

Figure 17:
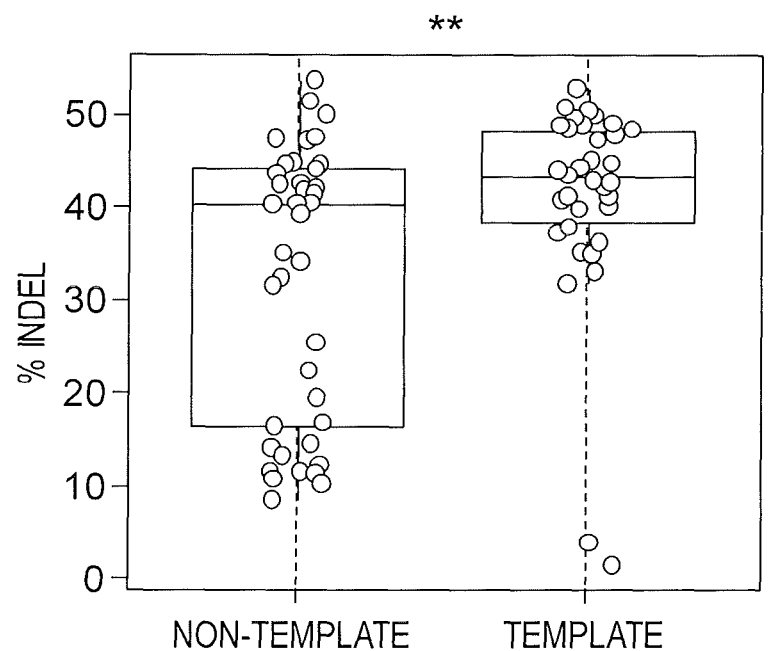
FIG. 17 shows that genome editing is enhanced by transcription through sgRNA annealing to the template strand. The graph shows indel frequencies caused by 17 template and 23 non-template sgRNA targeting distinct genes, wherein each point represents a mutation frequency of independent transfections, n=2 for each sgRNA.

In cells, individual sgRNA display variable efficiency for genome editing. Some variability has been attributed to the formation and the function of the Cas9 RNP itself (Wang, et al. (2014) Science 343:80-84). Some chromatin characteristics, such as the presence of nucleosomes or low levels of target gene transcription, correlate with low activity sgRNA (Chari, et al. (2014) Nat Methods 12:823-826; Hinz, et al. (2015) Biochemistry 54:7063-7066; Horlbeck, et al, (2016) Elife 5, pii:e12677). It was posited that a template strand bias also affects efficiency of Cas9-mediated genome editing, because the off-rate of Cas9 could be a rate limiting step in genome editing. If so, then sgRNA annealing to the template strand of transcribed genes would be more efficient than sgRNA annealing to the non-template strand. This was demonstrated in three distinct ways. First, previously reported indel mutation rates by 975 sgRNA in HEK293 cells (Chari, et al. (2014) Nat Methods 12:823-826) were analyzed by assigning template/non-template strand status to sgRNA and binning the sgRNA based on the relative mRNA level of the target gene. Genes in the top two quartiles of mRNA levels were more frequently mutated when targeted by template strand sgRNA. Second, 40 genes expressed in mouse ES cells were individually targeted (17 template, 23 non-template sgRNA) and the indel frequency of each target was measured by targeted deep sequencing. The percent indel frequency was significantly higher for template strand sgRNA compared to non-template strand sgRNA (FIG. 17). Third, the variability between genes was eliminated by targeting a single doxycycline-inducible transgene, mCherry, with ten template and seven non-template sgRNA (Table 6).

TABLE 6

| SgRNA Name | Strand | % Indel −Dox | % Indel +Dox |
|---|---|---|---|
| sgm1 | Template | 14.5 | 39.1 |
| sgm2 | Template | 16.7 | 52.3 |
| sgm3 | Non-Template | 19.7 | 26.7 |
| sgm4 | Template | 11.0 | 23.1 |
| sgm5 | Template | 7.2 | 19.9 |
| sgm6 | Template | 6.7 | 13.2 |
| sgm7 | Non-Template | 4.3 | 5.5 |
| sgm8 | Template | 6.5 | 17.5 |
| sgm9 | Non-Template | 3.6 | 2.5 |
| sgm10 | Template | 11.5 | 19.6 |
| sgm11 | Non-Template | 21.0 | 25.2 |
| sgm12 | Template | 19.2 | 39.5 |
| sgm13 | Non-Template | 27.0 | 17.6 |
| sgm14 | Non-Template | 12.6 | 15.5 |
| sgm15 | Template | 20.3 | 58.6 |
| sgm16 | Template | 11.0 | 20.1 |
| sgm17 | Non-Template | 6.7 | 4.9 |
| sgm18 | Non-Template | 8.3 | 6.9 |
| sgm19 | Template | 15.5 | 14.7 |
| sgm20 | Template | 18.0 | 46.8 |

Figure 16:
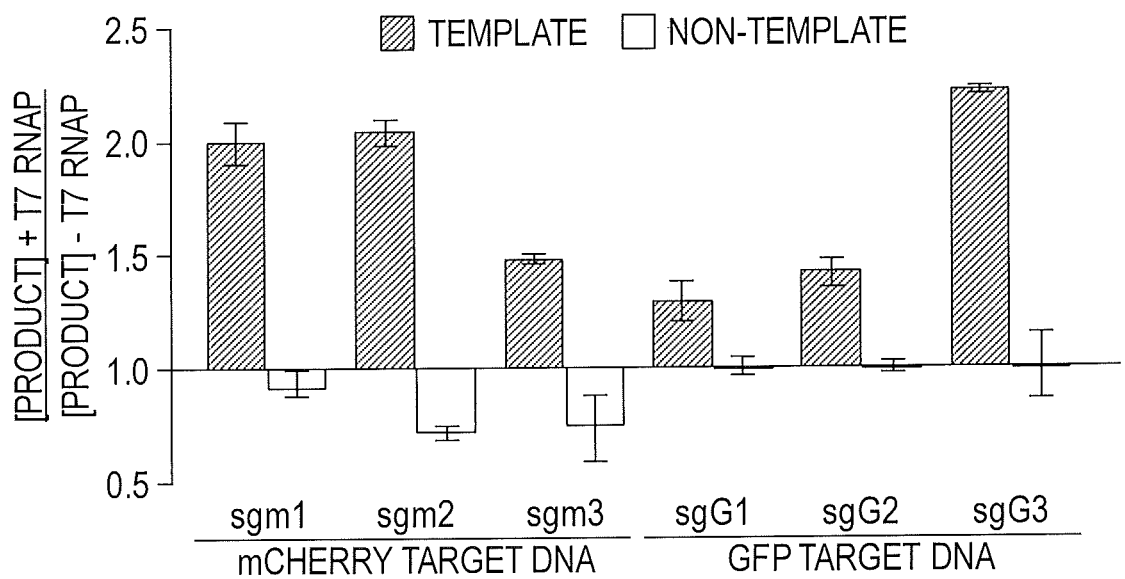
FIG. 16 shows that in vitro template strand bias is consistent across multiple sgRNA, i.e., sgRNA targeting mCherry and GFP (n=3). The schematic depicts mCherry target DNA converted into transcription templates that mediate template or non-template collisions for sgRNA.
Figure 18:
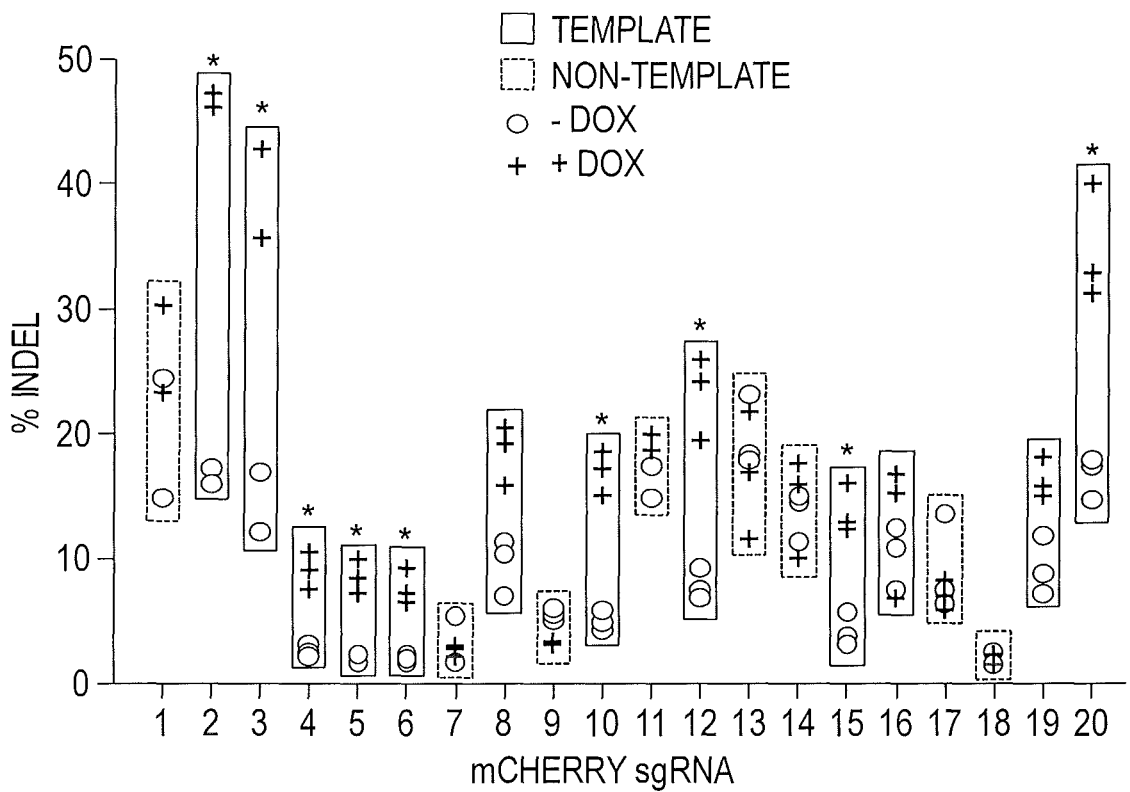
FIG. 18 shows that active transcription through template strand targeted sgRNA enhances mutagenesis frequencies. Mutagenesis frequencies by 17 sgRNA targeting a doxycycline-inducible mCherry were measured via T7E1 assays. Values represent mean±S.D., n=3. p<0.01, *p<0.001.

Measuring indel formation with T7 endonuclease 1 assays showed that stimulating transcription significantly increased indel formation only for template strand sgRNA (FIG. 18). The same strand bias was observed for the three mCherry sgRNA used to test in vitro effects of T7 RNAP (FIG. 16). Together, these data demonstrate genome editing efficiency can be stimulated by RNA Pol II transcription through a target site when it collides with the PAM-distal surface of Cas9.

Cas9 functioning as a multi-turnover nuclease could significantly enhance bacteriophage immunity in bacteria, which may need to survive an infection when many phage genomes are present. Interestingly, the nucleotide composition of bacteriophage genomes differ in the plus and minus strands (Jin, et al. (2014) BMC Genomics 15:793; Kwan, et al. (2005) Proc. Natl. Acad. Sci. USA 102:5174-5179; Lobry (1996) Mol. Biol. Evol. 13:660-665; Uchiyama, et al. (2008) Appl. Environ. Microbiol. 74:4149-4163), which is illustrated by a skew toward adenine and guanine in the plus strand of Streptococcus phages that infect S. pyogenes and S. thermophiles (34% adenine: 27% threonine, and 22% guanine: 17% cytosine) (Table 7). Consequently, the PAM sites for SpCas9 (NGG) and StCas9 (NNAGAAW) preferentially target the template strand at about a 2:1 ratio, which is similar to the high frequency of crRNA that target the template strand of bacteriophage in bacteriophage insensitive mutant strains (Achigar, et al. (2017) Sci. Rep. 7:43438; Levin, et al. (2013) PLoS Genet. 9:e1003312).

TABLE 7

| Phage | PAM | # Template | # Non-Template | % Template |
|---|---|---|---|---|
| Phage: 2972: 34704 bp | NNAGAAW | 179 | 52 | 77.5% |
| | NGG | 1450 | 777 | 65.1% |
| Phage 128: 34593 bp | NNAGAAW | 108 | 45 | 70.6% |
| | NGG | 1381 | 833 | 62.4% |
| Phage 73: 36377 bp | NNAGAAW | 183 | 63 | 74.4% |
| | NGG | 1467 | 793 | 64.9% |
| Phage 53: 34239 bp | NNAGAAW | 166 | 69 | 70.6% |
| | NGG | 1381 | 804 | 63.1% |
| Phage 858: 35543 bp | NNAGAAW | 169 | 64 | 72.5% |
| | NGG | 1476 | 758 | 66.1% |
| Phage 5093: 37184 bp | NNAGAAW | 219 | 96 | 69.5% |
| | NGG | 1329 | 714 | 65.1% |

TABLE 7-continued

| Phage | PAM | # Template | # Non-Template | % Template |
|---|---|---|---|---|
| Phage 7029: 35466 bp | NNAGAAW | 176 | 93 | 65.4% |
| | NGG | 1371 | 794 | 63.3% |
| Prophage 20167: 48800 bp | NNAGAAW | 302 | 117 | 72.1% |
| | NGG | 1999 | 1115 | 64.2% |
| Phage Sfi11: 39807 bp | NNAGAAW | 209 | 84 | 71.3% |
| | NGG | 1544 | 802 | 65.8% |
| Phage Sfi19: 37307 bp | NNAGAAW | 190 | 95 | 66.7% |
| | NGG | 1516 | 822 | 64.8% |
| Phage Sfi21: 40793 bp | NNAGAAW | 222 | 108 | 67.3% |
| | NGG | 1520 | 896 | 62.9% |
| Prophage TP-778L: 41757 bp | NNAGAAW | 200 | 81 | 71.2% |
| | NGG | 1600 | 920 | 63.5% |
| Prophage TP-J134: 45606 bp | NNAGAAW | 226 | 91 | 71.3% |
| | NGG | 1711 | 967 | 63.9% |
| Phage NM4: 40365 bp | NNAGAAW | 286 | 80 | 78.1% |
| | NGG | 1406 | 624 | 69.3% |
| Phage NM1: 43219 bp | NNAGAAW | 303 | 105 | 74.3% |
| | NGG | 1387 | 688 | 66.8% |
| Phage A25: 33900 bp | NNAGAAW | 173 | 52 | 76.9% |
| | NGG | 1472 | 779 | 70.9% |
| Phage T12: 37976 bp | NNAGAAW | 164 | 67 | 72.9% |
| | NGG | 1431 | 798 | 63.6% |

The data suggest that the strand biased PAM sequences of StCas9 and SpCas9 evolved to target the plus strand of bacteriophage genomes, because it provides a selective advantage for bacteria against bacteriophage. Compared to an evolutionarily challenging barrier of changing a genome-wide GC skew in bacteriophage, changing the PAM sequence used by Cas9 is relatively simpler and requires only a small number of mutations (Kleinstiver, et al. (2015) Nature 523:481-485). Targeting of the bacteriophage plus strand provides an advantage because it will more frequently result in multi-turnover nucleases upon transcription of lytic genes.

Figure 19:
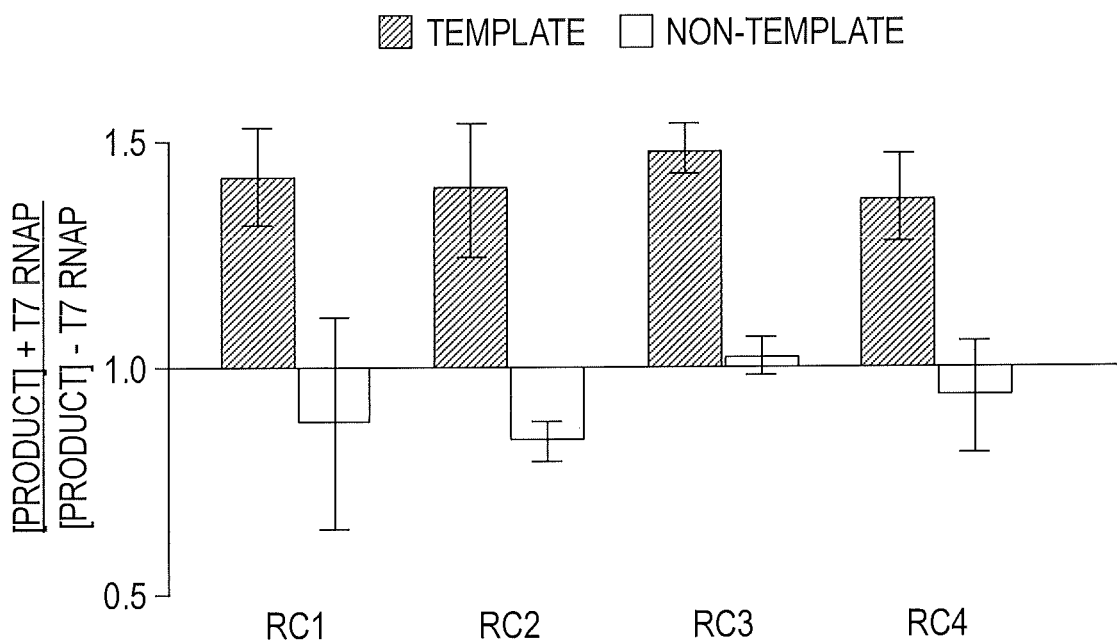
FIG. 19 shows that spacers RC1-4 mediate multi-turnover Cas9 activity when targeting the template strand as measured by in vitro Cas9 digestion reactions against φNM1 target DNAs harboring a T7 RNAP promoter on either end, respectively. Values represent mean±S.D. of fold change in cut DNA caused by addition of T7 RNAP, n=3.

To directly test a strand bias effect on bacterial immunity, two virulent versions of the φNM1 phage were used. One contained a mutation that inactivates the promoter required for transcription of lysogeny cassette (φNM1γ6; Goldberg, et al. (2014) Nature 514:633-637), and the other expresses the lysogeny cassette but harbors an inactivating deletion within the cI repressor gene (φNM1h1). Therefore, neither phage can establish lysogeny, but they differ in the transcription of the lysogeny cassette. Different bacterial strains were generated which harbored spacers targeting either template or non-template strand sequences within the repressor gene found in both φNM1γ6 and φNM1h1. Each strain was infected with each phage and their survival determined by measuring $OD_{600}$ over time. The interference efficiency of each spacer against the two phages was interpreted from plate-reader growth curves of infected bacterial cultures. The two spacers targeting the non-template strand (RC2 and RC4) showed similar interference against either phage. On the contrary, spacers targeting the template strand (RC1 or RC3) were notably more effective at cleaving φNM1h1's transcribed target. The same four target sites within φNM1 were tested for the ability of T7 RNAP translocation to turn Cas9 into a multi-turnover nuclease in vitro (FIG. 19), demonstrating the template strand bias effect on the phage genome. These results suggest that active transcription across Cas9 improves CRISPR immunity by converting Cas9 into a multi-turnover enzyme.

Figure 20:
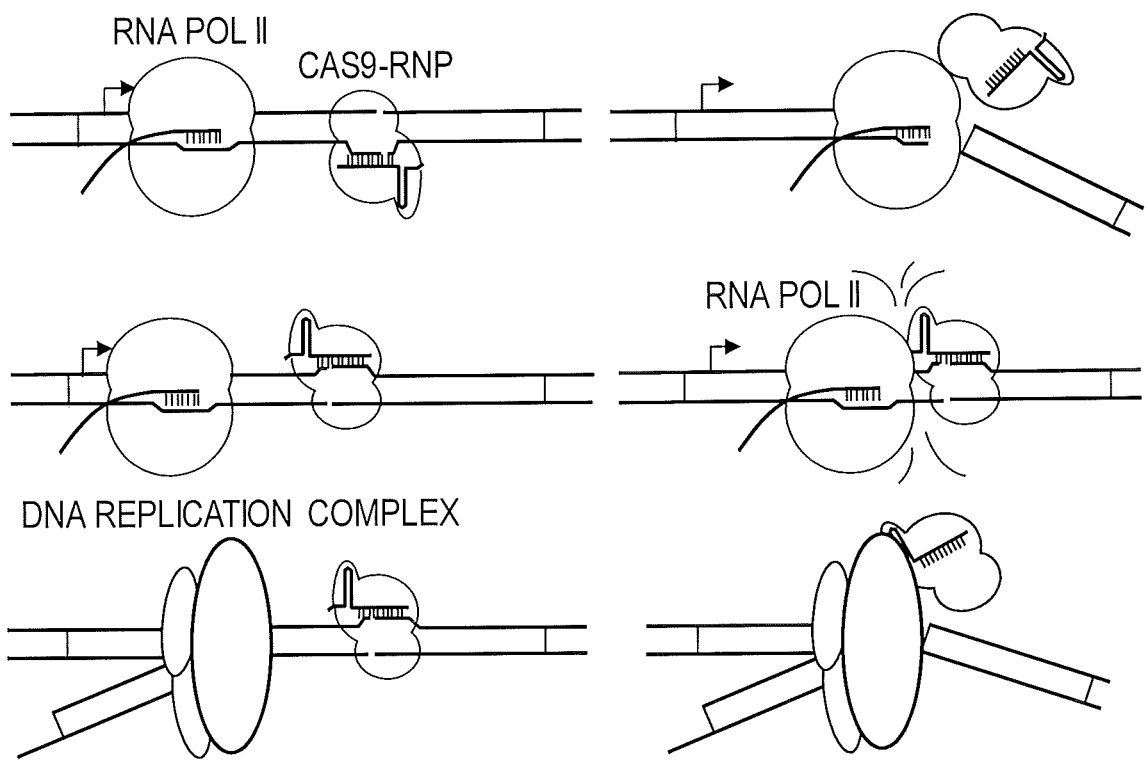
FIG. 20 shows that strand bias of the Cas9 endonuclease during genome editing results in different genome editing kinetics and differential mutation outcomes. The illustration depicts template versus non-template strand bias during genome editing. In particular, the top panel shows that when. Cas9 is targeted to the template strand, a translocating RNA polymerase is evicted through collision with the polymerase, thus resulting in cell-cycle independent Cas9-mediated DSB repair. By comparison, a non-template bound sgRNA is not evicted by RNA polymerase (middle panel). However, a non-template bound sgRNA is evicted from the double strand bread (DSB) during DNA replication by the various activities of the DNA replication complex which occurs during the HDR active phase of the cell cycle, potentially biasing the mutational outcome.

In summary, displacing Cas9 from its DSB stimulates genome editing efficiency and increases CRISPR immunity. The data indicate that the orientation-dependent displacement of Cas9 by RNAP provided a method for measuring the strand-bias effect on genomes. In addition to RNAP translocation through Cas9, other DNA metabolic processes, including replication and repair activities, likely generate sufficient force to dislodge Cas9 (FIG. 20). In contrast to the stereotypical translocation of RNAP along its template, the location and timing of those other activities within a genome are less predictable. Developing modified Cas9 enzymes or treatments that stimulate the removal of Cas9 from the DSB may increase the rate of the genome editing processes and reduce variability of sgRNA effectiveness. This should be especially useful at non-transcribed sites and in cells with low DNA metabolic activity.

Example 5: Additional Methods

Synthetically Directing Transcription Through the Cas9 Target Site. Transcription factor Cas9s: An RNA-guided nuclease (e.g., Cas9 or Cas12a) that is nuclease inactive (e.g., dCas9) is fused to a transcriptional activation domain or its sgRNA contains transcriptional activation domains (e.g., dCas9-VP64), and functions to recruit RNA polymerases to a specific region in the genome.

Directing RNA polymerase to Cas9 target sites: Transcription factor Cas9s is targeted upstream of the actual genome editing target site (the sequence that nuclease active Cas9 is directed). Both the transcription factor Cas9 and nuclease active Cas9 are present in the cell at the same time, and the transcription factor Cas9 directs RNA polymerase activity through a template bound nuclease active Cas9. Transcription factor Cas9s is a different species than nuclease active Cas9 to avoid the sharing of sgRNAs. For example, transcription factor Cas9 from *S. thermophilus* has a sgRNA that *S. pyogenes* cannot utilize. Therefore, *S. pyogenes* Cas9 can be the nuclease active one and the two can cooperate within this system.

Small Molecule Influenced Dissociation of Cas9 from the DSB. Small molecules that disrupt the Cas9-DSB complex may be identified via a high throughput screen including an assay where disruption of the complex mediates either release of DSB from Cas9 with dissociated Cas9 non-functional, or release of Cas9 from the DSB so that Cas9 is functional and a multi-turnover enzyme. Suitable assays include recombinant Cas9 from the desired species, purified sgRNA, and target DNA that is fluorescent. The fluorescence target DNA exists in the non-fluorescent form when it is in the Cas9-DSB state or free in the uncleaved state. The cleaved DNA that is dissociated from Cas9 will fluoresce as a readout for disruption of the Cas9-DSB complex. This assay is an example of the many fluorescent assays that could be used to detect the right small molecule.

Alternatively, small molecules that disrupt the Cas9-DSB complex with energetics that cause Cas9 dissociation from the DSB without completely inhibiting Cas9 association with target DNA may be designed. More particularly, small molecules are designed to specifically interact with the general Cas9-DSB complex so that they disruptively bind:
i) within the target DNA R loop (Intercalation between DNA strands);
ii) within the sgRNA:DNA hybrid (Intercalation between RNA and DNA strands);
iii) within the RuvC domain and non-target strand interaction (Intercalation between amino acid residues and DNA);
iv) within the HNH domain and target strand interaction (Intercalation between amino acid residues and DNA);
v) with the PAM sequence and the PAM interaction domain (Intercalation between amino acid residues and DNA);
vi) within the scaffold region of the sgRNA (the non-programmable region) to cause sgRNA or Cas9 unfolding;
vii) within or on the outer surface of the RuvC or HNH nuclease domains to disrupt sgRNA or Cas9 folding; or
viii) within or outside of any region of Cas9 or sgRNA that disrupts its folding and/or ability to bind the DSB.

Enzymatic Destruction of the sgRNA:DNA Hybrid. A Cas9 nuclease fused to an RNase H enzyme, domain or any RNA:DNA binding enzyme that has RNA:DNA degradation activities acts to dissociate the Cas9-DSB complex by destroying the sgRNA:DNA hybrid. Once Cas9 forms a complex with the DSB, the RNase recognizes this as a substrate and degrades it, resulting in release of Cas9 from the DSB. RNases are attached to the N- or C-terminus of Cas9 with a linker (glycine-serine type) that exists in a long or short format. Depending on the species of Cas9 that is used, the length may vary due to the amount of "reach" the enzyme needs to get to its substrate.

Enzymatic Destruction of the Surrounding DNA Sequence. A Cas9 nuclease is fused to one or more nucleases with specific or non-specific activities. The function of the additional nuclease is to cleave the immediately nearby genomic sequences so that the Cas9-DSB complex is completely removed and literally floats away. These additional nucleases can be fused to the N- or C-terminus of Cas9 using short or long linkers (glycine-serine) and are restriction enzymes that have small consensus sequences (less than 5 or 6 nucleotides).

Mutational Modification of the Cas9 Nuclease. The Cas9 nuclease is mutated by changing/deleting/inserting one or more amino acids residues such that the enzyme functions to release the DSB rather than staying bound, and the nuclease also may have newfound multi-turnover enzymatic activities. Such mutations can exist within or around the PAM interaction domain, the RuvC nuclease domain, and/or the HNH nuclease domain. These mutations can be generated through PCR or Gibson assembly, or a library of Cas9 mutants can be generated through error-prone PCR, then the mutants screened for multi-turnover nuclease activity and/or rapid dissociation from the DSB.

Example 6: Achieving Time-Regulated, Sequentially-Acting, Predetermined Cellular Behaviors Through Bioprocessor-Mediated Genetic Recording and Cellular Programming Genetic Recording of Cellular Processes. The dynamic events that occur over a cell's lifetime can be recorded into its genome using combinations of the modules, i.e., Cas fusion protein, activatable sgRNA, and strand bias, described herein. Cellular events of interest (natural or synthetic), which result in transcription can be linked to the modules to serve as inputs for either direct or indirect genetic recording of the event. For example, a gene containing an embedded normal sgRNA within its 3'-UTR will result in mutagenic activity by the sgRNA at a distinct genomic site once the gene is transcribed, ultimately creating a genetic record of the event. While simultaneously recording events of interest, a genetic recorder linked to cell cycle progression will record each cell division leading to a specific genomic barcode, hereafter termed "generational barcoding" (FIG. 11 and FIG. 12). This barcode allows for the reconstruction of generationally based lineage trees, and the recording data associated with other cellular events can be mapped within the context of the lineage tree to ascertain when and how long an event occurred. The process of a genetic recording event functions to passively barcode the cell population and results in the activity of a pre-programmed bioprocessor.

Bioprocessors and Bioprocessing. A bioprocessor is composed of one or more activatable sgRNA linked to one or several of the other modules described herein with the purpose of executing a series of sequential genetic events. The activatable sgRNA serve as the "program," and the regulation over Cas9 activity directed by these sgRNA serve as the central code. Cas9 activity is directly controlled by the activatable sgRNA existing in the "on" state or a normal sgRNA being present, and the sgRNA target site. The nature of the bioprocessor program provides sequential regulation of Cas9 activity, rendering a specific Cas9 activity to be dependent on completion of another Cas9 activity, such as conversion of an activatable sgRNA within the bioprocessor (FIG. 7). The dependency allows for the programming of the bioprocessor to be regulated by the generational barcoding system (FIG. 13), which results in a programmed Cas9 activity contingent on the cell completing a specific number of cell cycles.

The initiation of a bioprocessor's activity depends on a cellular event for which the bioprocessor is programmed to respond to. The general direct input to initiate bioprocessor activity requires transcription of a normal or on-state activatable sgRNA. These sgRNA can be embedded within endogenous or synthetic genes themselves, or can be controlled by their own promoter. The presence of the cellular event that causes transcription of the active sgRNA will result in a direct genetic recording event, wherein the cellular event causes activity of an sgRNA, or indirect genetic recording event, wherein the cellular event results in downstream control of sgRNA activity, such as a signaling cascade. This genetic recording event converts an activatable sgRNA from the "off" to the "on" state, allowing the next event programmed within the bioprocessor to begin.

The act of bioprocessing is sequential completion of the pre-programmed events by the required modules, and the central program of the bioprocessor are arrays of activatable sgRNA (FIG. 7 and FIG. 9). The output of each bioprocessor typically requires the other modules to influence the rate of activatable sgRNA conversion from the "off" to the "on" state. The rate is influenced by strand-biased Cas9 activity (FIG. 12) and cell cycle Cas9 (FIG. 11).

Outputs. The direct outputs of a bioprocessor are Cas9-mediated mutagenesis (genetic changes and barcoding), or transcriptional activation or repression (epigenetic regulation). These activities lead to changes in cellular behavior and can be multiplexed through design of the bioprocessor. Importantly, each output can be regulated by the number of cell cycle completions, such as expressing or mutating endogenous genes at specific or multiple points in the cell's lifetime. Outputs can be further regulated through bioprocessor dependencies on endogenous transcription. For example, 3'-UTR embedded sgRNA mediate the process of barcoding a cell or mutating/transcriptionally regulating a series of target genes when the gene of interest is expressed. The dependencies for a specific output can encompass few or many cellular activities and the only major requirement is validated Cas9 activity in the species of interest.

Example 7: Genetic Knock Outs to Induce Apoptosis After a Specific Number of Cell Cycle Completions Generational Barcoding. The cellular process being tracked is cell cycle progression. The generational barcoding bioprocessor uses a series of activatable sgRNA in combination with either the strand bias by targeting of the non-template strand (FIG. 12, FIG. 20) or cell cycle Cas9 (FIG. 11).

Strand Bias. Ten activatable sgRNA are placed in an array to count 10 cell divisions with each containing their own human U6 promoter for mammalian cells, or an SNR52 promoter for yeast. Each activatable sgRNA is targeted to the DNA of the activatable sgRNA directly adjacent and downstream of its own DNA. Each sgRNA binds to the non-template strand, allowing for one activatable sgRNA per cell cycle to be converted from the "off" to the "on" state. The first activatable sgRNA in the array will be activated through either transfection of the activating sgRNA, or it will be a normal sgRNA and transcription will be controlled through an inducible promoter. Activity by the first sgRNA will start begin the process of recording 10 cells divisions.

Cell Cycle Cas9. Twenty sgRNA are placed in an array, with odd numbered sgRNAs corresponding to the G1-phase specific Cas9 (PAM=NGG) and even numbers corresponding to G2-phase specific Cas9 (PAM=NAG). Each sgRNA in the array will be targeted to the nascent sgRNA's DNA as shown in FIG. 11, and two sgRNAs per cell cycle will be converted from the "off" to the "on" state following the mechanism described in FIG. 11.

Bioprocessing. Upon conversion from "off" state to "on," the final sgRNA (sgRNA KS1) in the array is targeted to the genomically integrated DNA of another sgRNA at another location. The sgRNA at the second location (sgRNA KS2) is converted to the "on" state and targets Cas9 activity to three distinct sgRNAs (sgRNA KS3, sgRNA KS4 and sgRNA KS5) located at three other locations in the genome. Cas9 bound to sgRNA KS2 converts sgRNA KS3, sgRNA KS4 and sgRNA KS5 to the "on" state.

Output. sgRNA KS3 is targeted to the template strand of the Bcl2 open reading frame (ORF), sgRNA KS4 is targeted to the template strand of the MDM2 ORF, and sgRNA KS5 is targeted to the template strand of the AKT ORF. Template strand targeting ensures fast genome editing kinetics to maximize the rate of genetic disruption to these proteins. Bcl2, MDM2, and AKT all promote cell survival via different mechanisms. Disruption of all the genes results in efficient activation of the intrinsic apoptotic pathway. In yeast, the homologs to these proteins are Bcl2 (Bcl2) and Sch9p (AKT), and MDM2 is replaced by an sgRNA targeting Tps1. Furthermore, the generational barcoding locus can be sequenced to reconstruct lineage trees from surviving cells.

Figure 22:
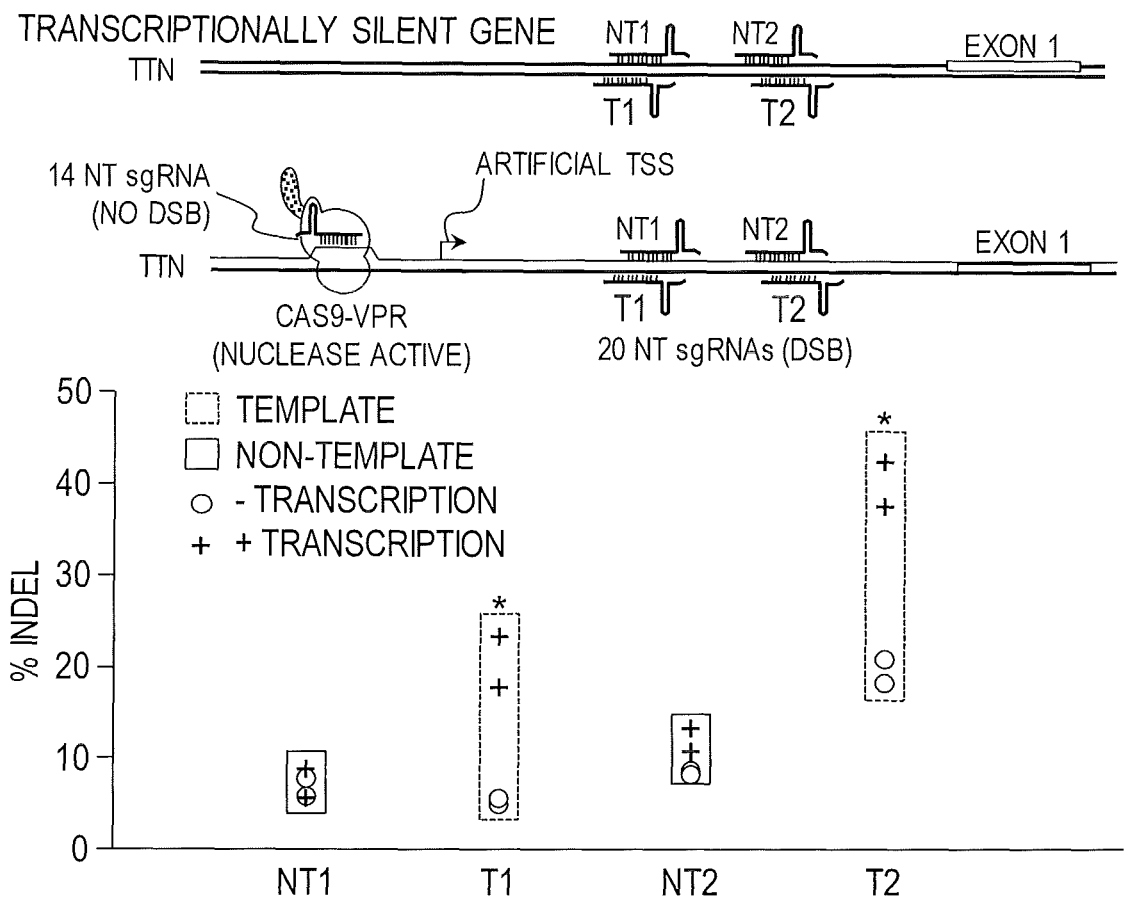
FIG. 22 shows the results of combining Cas9-VPR with 14 nt and 20nt sgRNAs on mutagenesis and transcriptional activation. Cas9-VPR is a nuclease active Cas9 fused to the transcriptional activation, VPR. Through truncating sgRNAs to 14nt, Cas9 nuclease activity is ablated but DNA binding is maintained, allowing for recruitment of RNA polymerase II without introduction of DSBs. Shown is a schematic depicting the targeting of a silent endogenous gene, TTN, for transcriptional activation and mutagenesis by Cas9-VPR. Strand bias was tested at TTN through synthetically activating transcription of the human TTN gene using Cas9-VPR construct. Nuclease active Cas9-VPR was targeted to activate transcription, but to not introduce DSBs using a 14-nt sgRNA. Simultaneously, a 20-nt sgRNA targeted to either the template or non-template strand was provided to drive transcription mediated by 14nt-Cas9-VPR through Cas9 cleavage sites. Genomic DNA was harvested 48 hours after transfection, and mutation frequencies are shown as determined via T7E1 assays. Transcription levels generated by the 14nt sgRNA targeted to TTN were assessed by quantitative real-time PCR analysis of RNA and an approximately 5-fold change in transcript levels was observed.

Example 8: Genetic Knock Outs and Transcriptional Activation to Induce Cellular Quiescence After a Specific Number of Cell Cycle Completions Genetic Recording of Cellular Processes. The process being tracking is cell cycle progression, and the generational barcoding system employed is largely similar to the one described Example 7, except only the strand bias is used in this example. In this system, the Cas9 nuclease utilized is a nuclease active Cas9 fused to the transcriptional activation domain "VPR" (Kiani, et al. (2015) Nature Meth. 12(11): 1051-4). Nuclease activity and recruitment of RNA polymerase II (RNAP) is modulated by changing the length of the sgRNA. A 20nt sgRNA allows Cas9 to cleave DNA and mediate mutagenesis, while a 14nt sgRNA ablates Cas9 activity, but the nuclease remains bound to DNA and can recruit RNAP to transcribe the target locus (see, e.g., FIG. 22).

Bioprocessing. The final sgRNA in the generational barcoding system (sgRNA QT2) targets another sgRNA's DNA (sgRNA QT2), and activated QT2 then targets three distinct sgRNA's DNA (sgRNA QT3, sgRNA QT4, and sgRNA QT5). In this example, sgRNA QT3 is a 20nt sgRNA targeted to E2F, sgRNA QT4 is 14nt sgRNA targeted to the promoter of P16$^{ink4a}$, and sgRNA QT5 is 14nt sgRNA targeted to the promoter of P21. The 14nt sgRNAs target the promoters within 200 bp of the transcription start site (TSS) to efficiently activate transcription.

Outputs. sgRNA QT3 is targeted to the template strand of E2F to induce a genetically disrupting mutation. Loss of E2F results in permanent cell cycle arrest in the G1 phase or entrance into the G0 phase. sgRNA QT4-mediated expression of P16$^{ink4a}$ and sgRNA QT5-mediated expression of P21 induces entrance into the G0 phase, rendering cell growth inhibition and efficient quiescence. For yeast homologs, E2F (E2F), transcriptional activation of P16$^{ink4a}$ and P21 are replaced with retinoblastoma protein, RB. Furthermore, the generational barcoding locus can be sequenced to reconstruct lineage trees.

Example 9: A Bioprocessor that Detects Cellular Stress and Inducing Apoptosis Genetic Recording of Cellular Processes. The cellular process being recorded in this system is the metabolic stress consequence, reactive oxygen species (ROS). In order to monitor this process, a normal sgRNA is embedded into the 3'-untranslated regions (3'-UTR) in 3 respective ROS-induced genes, NF-kappaB, ATF, and AP-1. The embedded sgRNA is flanked by two cis-cleaving ribozymes (RGR), resulting in the production of a functional sgRNA upon full transcription of the gene (see, e.g., FIG. 23). However, these genes are silent until accumulation of ROS occurs. The cells for which this processor is integrated express two Cas9 variants: wild-type Cas9 (WT-Cas9, PAM=NGG) and a dCas9-KRAB (PAM=NAG). dCas9-KRAB is a nuclease inactive Cas9 that recruits endogenous transcriptional repression machinery.

Bioprocessing. Upon transcription of any of the three genes, a functional sgRNA is produced. This sgRNA (sgRNA NF1) is targeted to the DNA of three distinct activatable sgRNAs (NF2, NF3 and NF4). sgRNAs NF1, sgRNA NF2, and sgRNA NF3 are all complementary to DNA which contains an NGG PAM sequence, rendering their ability to mediate mutagenesis specific to WT-Cas9. sgRNA NF4 binds DNA containing an NAG PAM, rendering its activity specific to dCas9-KRAB. Successful conversion of sgRNA NF2 to the "on" state targets Cas9 mutagenic activity to Bcl2, conversion of sgRNA NF3 targets activity to MDM2, and conversion of sgRNA NF4 represses transcription of TNFα through binding within 50 bp after the TSS. These activities can also be performed in the presence of the generational barcoding to ascertain timing of ROS accumulation with respect to cell, aging as long as the DNA of sgRNA NF2, sgRNA NF3 and sgRNA NF4 is sequenced.

Outputs. Mutagenesis of Bcl2 and MDM2 will result in induction of the intrinsic apoptotic pathway. Repression of the TNFα locus will preclude the secretion of TNFα to ultimately reduce inflammatory responses and necrosis of nearby cells. In yeast, the homologs to these proteins are Bcl2 (Bcl2), MDM2 is replaced by an sgRNA targeting Tps1, and TNFα has no replacement.

Example 10: Time-Encoded Induction of a Heterologous Gene of Interest That Confers Transcription of Cell Survival Genes and Repression of Inflammatory Genes Genetic Recording of Cellular Processes. The major process being recorded and serving as the main input for the bioprocessor is cell cycle progression. In this system, the generational barcoding process records 10 cell divisions by using strand bias. The barcoding and transcriptional activation events are mediated by Cas9-VPR (PAM=NGG), and the cells also express dCas9-KRAB (PAM=NAG).

Bioprocessing 1. Upon completion of 10 cell cycles, the final sgRNA in the generational barcoding array (sgRNA H1) is a 20nt sgRNA that is targeted to the DNA of a 14nt sgRNA (sgRNA H2). sgRNA H2 is targeted to the promoter of the transcriptionally silent heterologous gene of interest (GOI). The 14nt sgRNA H2 binds a sequence with an NGG PAM, resulting in Cas9-VPR targeting to the site and transcriptional activation of the heterologous gene product.

Output 1. Expression of the heterologous gene occurs, which encodes two normal sgRNA, RGRs in the 3'-UTR (RGR H3 and RGR H4).

Bioprocessing 2, The RGRs become functional sgRNAs upon transcription, converting to sgRNA H3 and sgRNA H4. sgRNA H3 targets Cas9-VPR to the Bcl2 promoter, and sgRNA H5 targets dCas9-KRAB near the TSS of Interferon alpha.

Output 2. Activity by sgRNA H4 results in transcription of Bcl2 which promotes cell survival by inhibiting apoptosis. sgRNA H5 represses Interferon alpha which reduces potential cellular stress responses and secretion of inflammatory cytokines to surrounding cells.

Example 11: Bioprocessor-Mediated Linkage of Two Independent Endogenous Pathways to Produce a Novel Cellular Behavior Genetic Recording of Cellular Processes. The processes being recorded are receptor-mediated signaling of one pathway, and transcriptional activity of a second pathway, with the second pathway depending on the first pathway. The recording is mediated by Cas9-VPR activity directed by 3'-UTR normal sgRNA in a gene regulated by the receptor signaling cascade (gene 1) and the conversion of a 3'-UTR embedded activatable sgRNA to the "on" state in gene 2.

Bioprocessing. Gene 2 is constantly transcribed and contains an inactive, activatable RGR in its 3'-UTR (sgRNA 2). The conversion of sgRNA 2 to the "on" state depends on the expression of sgRNA 1, which is a normal sgRNA embedded in the 3'-UTR of gene 1. Upon receptor-ligand binding, the signaling cascade of interest induces transcription of gene 1, resulting in the expression of sgRNA 1. sgRNA 1 converts sgRNA 2 to the "on" state. sgRNA 2 is targeted to the DNA of activatable sgRNA 3, converting it to the "on" state. sgRNA 3 is a 14nt sgRNA and is targeted to the promoter of the target gene of interest.

Outputs. The activity of sgRNA 3 causing the expression of some target gene is entirely dependent on these two pathways being expresses at the same time, thus allowing the linkage of two normally unassociated pathways. If performed in the context of generational barcoding, the DNA of the activatable sgRNA can be sequenced to ascertain kinetics and timing of the process.

Example 12: Induction of Genes at Specific Cell Cycle Completion Numbers to Manipulate Cell Fitness Genetic Recording of Cellular Processes. Cell cycle progression is recorded through Cas9-VPR-mediated generational barcoding utilizing strand bias for 10 cell cycles. Activatable sgRNAs converted to the "on" state after completion of 5 (sgRNA C1), 7 (sgRNA C2) and 10 (sgRNA C3) cell divisions have secondary targets to either mediate transcription or mutations at distinct endogenous genes.

Bioprocessing. Upon completion of 5 cell divisions, sgRNA C1 is activated and is targeted to the DNA of sgRNA F1. sgRNA F1 is a 14nt sgRNA and is targeted to the promoter of a heterologous gene of interest to promote transcription. Upon completion of 7 cell cycles, sgRNA C2 is converted to the "on" state and is targeted to the DNA of sgRNA F2. sgRNA F2 is 20nt sgRNA that is targeted to the DNA of three distinct, 14nt activatable sgRNAs (sgRNA E1, E2 and E3). This targeting converts these sgRNA to the "on" state, and they bind the promoters of Malic enzyme (sgRNA E1), catalase (sgRNA E2), and superoxide dismutase (sgRNA E3) to activate transcription. After the 10th and final recorded cell division, sgRNA C3 is activated and targets the DNA of sgRNA F3 (20nt). sgRNA F3 converts sgRNA E4, E5 and E6 to the "on" state through genome editing at the associated DNA. sgRNA E4 is targeted to the ORF of Bcl2, sgRNA E5 is targeted to the ORF of MDM2 and sgRNA E6 is targeted to the ORF of AKT>

Outputs. At the $5^{th}$ cell division, the heterologous gene of interest is expressed continuously throughout the remainder of cell survival. After the 7th cell cycle, NAPDH producing Malic enzyme is targeted to increase the level of expression simultaneously as catalase and superoxide dismutase. These targeting efforts endeavor to decrease the cellular stress caused by ROS accumulation as the heterologous gene product is being made. After 10 cell cycles, apoptosis is induced.

Figure 21:
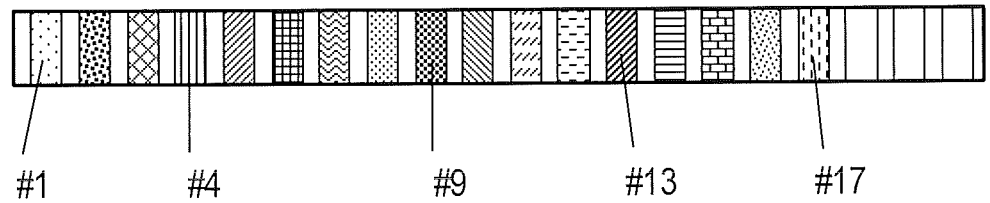
FIG. 21 depicts an approach for automating cellular behaviors through bioprocessor technologies which use an array or activatable sgRNA to track cellular histories over an extended period of time, a generational barcoding system. Cellular activities associated with the production of a monoclonal antibody (mAB) are linked to the generational barcoding system. Once various cellular histories have been tracked and specific events affecting production of mAB (e.g., events #1, #4, #9, etc), the data is used to modify the bioprocessor such that the cells are pre-programmed to circumvent the detected issues. This creates a high performing, mAB producing cell by embedding a program of instructions into the cell's genome. Furthermore, the core bioprocessor can be supplemented by activatable sgRNA that can be activated by cell surface receptor-ligand interactions to carry out a series of programs, each at a specific stage in during the lifetime of the cell culture thereby optimizing mAB production.
Figure 21:
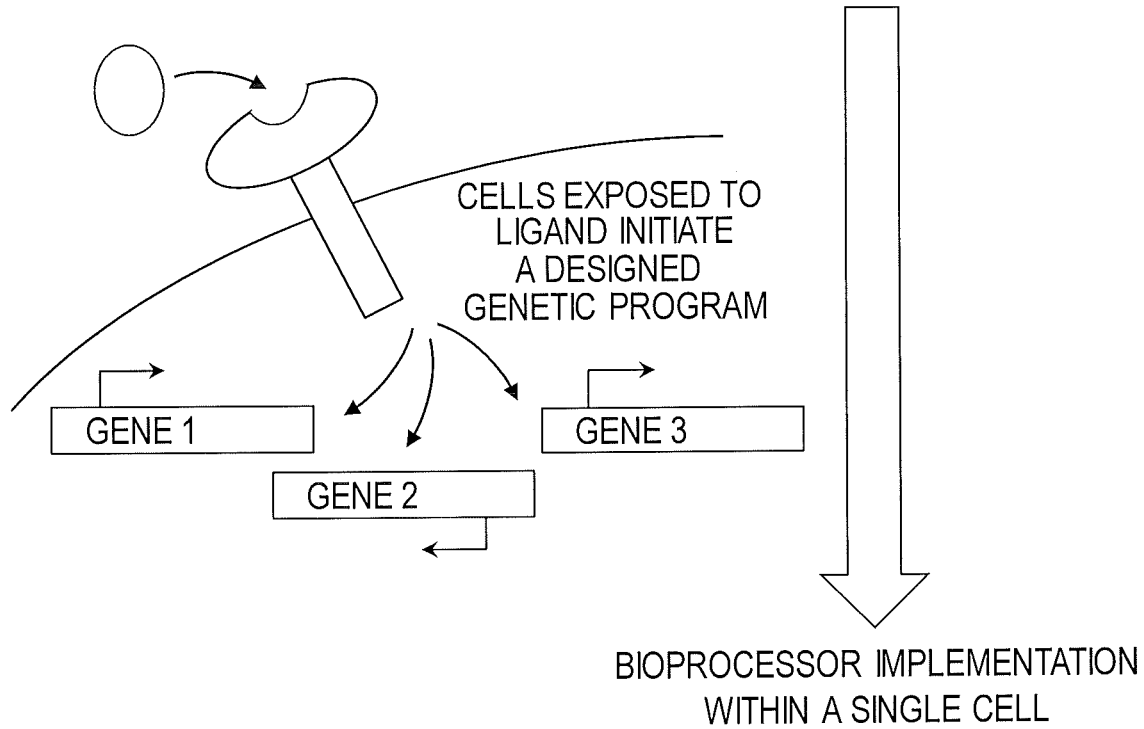
Figure 21:
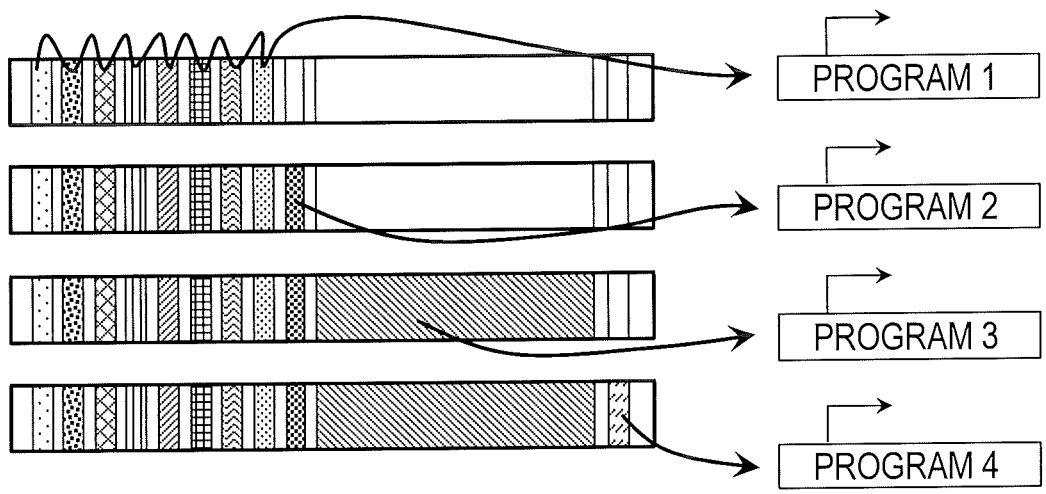

Example 13: Tracking Cellular Histories of Biotherapeutic Producing Cells for Automating Cellular Behaviors Through Bioprocessor Technologies It is known that viability and productivity of CHO cell cultures producing a monoclonal antibody (mAB) over 7 days decreases when highest mAB titers are achieved at approximately days 5-6. The system of the invention barcode cells before they divide and couples cell division with other cellular behaviors, such as mAB expression and toxicity levels. By way of illustration, whereas cell division numbers 1-9 do not exhibit any signs of toxicity and maintain high mAB expression, at cell division number 13 a medium amount of toxicity, reduced mAB expression and antibody aggregation is detected, and at cell division umber 17 a high level of toxicity, no product secretion and beginning of cell death are detected (FIG. 21). From this analysis it can be concluded that continuous product expression is toxic overtime due to metabolic stress; growth rates differ across the cell population as a result of the bioreactor; cells that silence the product gene gain a fitness advantage and grow faster; medium cell culture densities give the best yield but at the cost of cell health; and induction of product expression at cell division number 9 reduces toxicity and maximizes yield. Accordingly, using the data generated from genetic recordings, a high performing, mAB producing cell can be created by embedding a program of instructions into the cell's genome using activatable sgRNA. For example, at cell division 1, program 1 can be implemented, which promotes cell propagation. At cell division number 9, program 2 can be implemented, which promotes gene product induction. At cell division number 10, program 3 can be implemented, wherein cell cycle arrest is induced with a concomitant expression of cell survival gens and gene product expression. At cell division number 11, program 4 is implemented such that all of the product is secreted and cell death is induced. See FIG. 21.

---

What is claimed is:

1. A CRISPR/Cas system comprising a Cas endonuclease and a cognate single guide RNA (sgRNA), wherein the cognate sgRNA is an activatable sgRNA harboring an inactivation sequence in a non-essential region of the sgRNA, wherein said inactivation sequence comprises one or more RNA-guided endonuclease recognition sites, and the activatable sgRNA is encoded by a nucleic acid molecule of SEQ ID NO:14, SEQ ID NO:15, SEQ ID NO:16, SEQ ID NO:17, SEQ ID NO:18, SEQ ID NO:19, SEQ ID NO:20, SEQ ID NO:21 or SEQ ID NO:22.

2. The system of claim 1, wherein the activatable sgRNA targets a transcribed strand of a nucleic acid molecule.

3. The system of claim 1,
wherein the inactivation sequence is a cis-acting ribozyme encoded by a nucleic acid molecule of SEQ ID NO:4.

4. The system of claim 1, further comprising an array of activatable sgRNAs, where the cognate sgRNA targets at least one activatable sgRNA in the array of activatable sgRNAs.

5. An activatable single guide RNA (sgRNA) harboring an inactivation sequence in a non-essential region of the sgRNA, wherein said inactivation sequence comprises one or more RNA-guided endonuclease recognition sites, and wherein the activatable sgRNA is encoded by a nucleic acid molecule of SEQ ID NO:14, SEQ ID NO:15, SEQ ID NO:16, SEQ ID NO:17, SEQ ID NO:18, SEQ ID NO:19, SEQ ID NO:20, SEQ ID NO:21 or SEQ ID NO:22.

6. A nucleic acid comprising a coding sequence, a 5'-untranslated region and a 3'-untranslated region, wherein said nucleic acid has inserted in the 5'-untranslated region or 3'-untranslated region an activatable single guide RNA of claim 5.

7. A CRISPR/Cas system comprising a Cas endonuclease and a cognate single guide RNA (sgRNA), wherein the cognate sgRNA is an activatable sgRNA harboring an inactivation sequence in a non-essential region of the activatable sgRNA, wherein said inactivation sequence comprises one or more endonuclease recognition sites and the inactivation sequence is a cis-acting ribozyme encoded by a nucleic acid molecule of SEQ ID NO:2 or SEQ ID NO:3.

8. An activatable single guide RNA (sgRNA) harboring an inactivation sequence in a non-essential region of the sgRNA, wherein said inactivation sequence comprises one or more endonuclease recognition sites, and the inactivation sequence is a cis-acting ribozyme encoded by a nucleic acid molecule of SEQ ID NO:2 or SEQ ID NO:3.

* * * * *

SEQUENCE LISTING

<160> NUMBER OF SEQ ID NOS: 120

<210> SEQ ID NO 1
<211> LENGTH: 100
<212> TYPE: RNA
<213> ORGANISM: Streptococcus pyogenes

<400> SEQUENCE: 1
ggggccacua gggacaggau guuuuagagc uagaaauagc aaguuaaaau aaggcuaguc    60
cguuaucaac uugaaaaagu ggcaccgagu cggugcuuuu                         100

<210> SEQ ID NO 2
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 2
ggggtgcttc ggatgctgat gagtccgtga ggacgaaaca gggcaacctg tccatccggt    60
atccc                                                               65

<210> SEQ ID NO 3
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 3
ggtgcctaac actgccaatg ccggtcccaa gcccggataa aagtggaggg ggca         54

<210> SEQ ID NO 4
<211> LENGTH: 52
<212> TYPE: DNA
<213> ORGANISM: Artificial sequence
<220> FEATURE:
<223> OTHER INFORMATION: Synthetic oligonucleotide

<400> SEQUENCE: 4
cctgtcaccg gatgtgcttt ccggtctgat gagtccgtga ggacgaaaca gg           52

<210> SEQ ID NO 5
<211> LENGTH: 186
<212> TYPE: DNA
<213> ORGANISM: Artificial sequence
<220> FEATURE:
<223> OTHER INFORMATION: Synthetic polynucleotide

<400> SEQUENCE: 5
gttttagagc tagaaatagc aagttaaaat aaggctagtc cgttatcaac ttcgggcgcc   60
tcagatacgg tcgcctgtca ccggatgtgc tttccggtct gatgagtccg tgaggacgaa   120
acaggcgatt ttttaacttc gggcgcctca gatacgggcc cgaagtggca ccgagtcggt   180
gctttt                                                               186

<210> SEQ ID NO 6
<211> LENGTH: 182
<212> TYPE: DNA
<213> ORGANISM: Artificial sequence
<220> FEATURE:
<223> OTHER INFORMATION: Synthetic polynucleotide

<400> SEQUENCE: 6
gttttagagc tagaaatagc aagttaaaat aaggctagtc cgttatcaac ttcgggcgcc   60
tcagatacgg ggtgcctaac actgccaatg ccggtcccaa gcccggataa aagtggaggg   120
ggcatttttt aacttcgggc gcctcagata cgggcccgaa gtggcaccga gtcggtgctt   180
tt                                                                   182

<210> SEQ ID NO 7
<211> LENGTH: 192
<212> TYPE: DNA
<213> ORGANISM: Artificial sequence
<220> FEATURE:
<223> OTHER INFORMATION: Synthetic polynucleotide

<400> SEQUENCE: 7
gttttagagc tagaaatagc aagttaaaat aaggctagtc cgttatcaac ttcgggcgcc   60
tcagatacgg ggggtgcttc ggatgctgat gagtccgtga ggacgaaaca gggcaacctg   120
tccatccggt atccttttt taacttcggg cgcctcagat acgggcccga agtggcaccg   180
agtcggtgct tt                                                        192

```
<210> SEQ ID NO 8
<211> LENGTH: 194
<212> TYPE: DNA
<213> ORGANISM: Artificial sequence
<220> FEATURE:
<223> OTHER INFORMATION: Synthetic polynucleotide

<400> SEQUENCE: 8
gttttagagc tgggtcgggc gcctcagata cgggggtgc ttcggatgct gatgagtccg      60
tgaggacgaa acagggcaac ctgtccatcc ggtatcccaa cttcgggcgc ctcagatacg     120
ggcccgaccc agcgagttaa aataaggctt agtccgtact caacttgaaa aggtggcacc    180
gattcggtgt tttt                                                      194

<210> SEQ ID NO 9
<211> LENGTH: 194
<212> TYPE: DNA
<213> ORGANISM: Artificial sequence
<220> FEATURE:
<223> OTHER INFORMATION: Synthetic polynucleotide

<400> SEQUENCE: 9
gttttagagc tgggtaccca gcgagttaaa ataaggctta gtccgtactc aacttgaacg      60
ggcgcctcag atacgggggg tgcttcggat gctgatgagt ccgtgaggac gaaacagggc    120
aacctgtcca tccggtatcc caacttcggg cgcctcagat acgggcccga aggtggcacc    180
gattcggtgt tttt                                                      194

<210> SEQ ID NO 10
<211> LENGTH: 194
<212> TYPE: DNA
<213> ORGANISM: Artificial sequence
<220> FEATURE:
<223> OTHER INFORMATION: Synthetic polynucleotide

<400> SEQUENCE: 10
gtttttgtac tctggtcggg cgcctcagat acggggggtg cttcggatgc tgatgagtcc     60
gtgaggacga acagggcaa cctgtccatc cggtatccca acttcgggcg cctcagatac    120
gggcccgacc agaagctaca aagataaggc ttcatgccga aatcaacacc ctgtcatttt    180
atggcaggtg tttt                                                      194

<210> SEQ ID NO 11
<211> LENGTH: 194
<212> TYPE: DNA
<213> ORGANISM: Artificial sequence
<220> FEATURE:
<223> OTHER INFORMATION: Synthetic polynucleotide

<400> SEQUENCE: 11
gtttttgtac tctggtacca gaagctacaa agataaggct tcatgccgaa atcaacaccc     60
tgtcattcgg gcgcctcaga tacgggggt gcttcggatg ctgatgagtc cgtgaggacg    120
aaacagggca acctgtccat ccggtatccc aacttcgggc gcctcagata cgggcccgtt    180
atggcaggtg tttt                                                      194

<210> SEQ ID NO 12
<211> LENGTH: 215
<212> TYPE: DNA
<213> ORGANISM: Artificial sequence
<220> FEATURE:
<223> OTHER INFORMATION: Synthetic polynucleotide
```

<400> SEQUENCE: 12

```
gttttagtac tctggaaaca gaatctacta aaacaaggca acgggcgcct cagatacggt      60
cgcctgtcac cggatgtgct ttccggtctg atgagtccgt gaggacgaaa caggcgaaac     120
ttcgggcgcc tcagatacgg gcccgaagtg gcaccgagtc ggtgcttttg acgaatgccg     180
tgtttatctc gtcaacttgt tggcgagatt ttttt                                215
```

<210> SEQ ID NO 13
<211> LENGTH: 215
<212> TYPE: DNA
<213> ORGANISM: Artificial sequence
<220> FEATURE:
<223> OTHER INFORMATION: Synthetic polynucleotide

<400> SEQUENCE: 13

```
gttttagtac tctggaaaca gaatctacta aaacaaggca agacgaatgc cgtgtttatc      60
tcgtcaactc gggcgcctca gatacggtcg cctgtcaccg gatgtgcttt ccggtctgat     120
gagtccgtga ggacgaaaca ggcgaaactt cgggcgcctc agatacgggc cgaagtggc     180 accgagtcgg tgcttttgt tggcgagatt ttttt                                 215
```

<210> SEQ ID NO 14
<211> LENGTH: 81
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (53)..(57)
<223> OTHER INFORMATION: n is a, c, g, or t

<400> SEQUENCE: 14

```
gttttagagc tagaaatagc aagttaaaat aaggctagtc cgttatcaac ttnnnnnaag      60
tggcaccgag tcggtgcttt t                                                81
```

<210> SEQ ID NO 15
<211> LENGTH: 88
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (16)..(20)
<223> OTHER INFORMATION: n is a, c, g, or t

<400> SEQUENCE: 15

```
gttttagagc tgggtnnnnn acccagcgag ttaaaataag gcttagtccg tactcaactt      60
gaaaaggtgg caccgattcg gtgttttt                                         88
```

<210> SEQ ID NO 16
<211> LENGTH: 88
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (59)..(63)
<223> OTHER INFORMATION: n is a, c, g, or t

<400> SEQUENCE: 16

```
gttttagagc tgggtaccca gcgagttaaa ataaggctta gtccgtactc aacttgaann      60
```
nnnaaggtgg caccgattcg gtgttttt                                              88

<210> SEQ ID NO 17
<211> LENGTH: 88
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (17)..(21)
<223> OTHER INFORMATION: n is a, c, g, or t

<400> SEQUENCE: 17
gtttttgtac tctggtnnnn naccagaagc tacaaagata aggcttcatg ccgaaatcaa          60
caccctgtca ttttatggca ggtgtttt                                             88

<210> SEQ ID NO 18
<211> LENGTH: 88
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (68)..(72)
<223> OTHER INFORMATION: n is a, c, g, or t

<400> SEQUENCE: 18
gtttttgtac tctggtacca gaagctacaa agataaggct tcatgccgaa atcaacaccc          60
tgtcattnnn nnttatggca ggtgtttt                                             88

<210> SEQ ID NO 19
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (20)..(24)
<223> OTHER INFORMATION: n is a, c, g, or t

<400> SEQUENCE: 19
tagatgttgt catctttaan nnnn                                                 24

<210> SEQ ID NO 20
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (15)..(19)
<223> OTHER INFORMATION: n is a, c, g, or t

<400> SEQUENCE: 20
tagatgttgt catcnnnnnt ttaa                                                 24

<210> SEQ ID NO 21
<211> LENGTH: 92
<212> TYPE: DNA
<213> ORGANISM: Artificial sequence
<220> FEATURE:
<223> OTHER INFORMATION: Synthetic oligonucleotide
<220> FEATURE:

```
<221> NAME/KEY: misc_feature
<222> LOCATION: (42)..(46)
<223> OTHER INFORMATION: n is a, c, g, or t

<400> SEQUENCE: 21
gttttagtac tctggaaaca gaatctacta aaacaaggca annnnngacg aatgccgtgt      60
ttatctcgtc aacttgttgg cgagattttt tt                                    92

<210> SEQ ID NO 22
<211> LENGTH: 92
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (70)..(74)
<223> OTHER INFORMATION: n is a, c, g, or t

<400> SEQUENCE: 22
gttttagtac tctggaaaca gaatctacta aacaaggca agacgaatgc cgtgtttatc       60
tcgtcaactn nnnntgttgg cgagattttt tt                                    92

<210> SEQ ID NO 23
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 23
gcctcacacg gaatct                                                      16

<210> SEQ ID NO 24
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 24
gagagccctc tcccaatctt c                                                21

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ggagccgtac atgaactgag                                                  20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
ggcaccaact tcccctccga                                                  20

<210> SEQ ID NO 27
<211> LENGTH: 20
```

<212> TYPE: DNA
<213> ORGANISM: Artificial sequence
<220> FEATURE:
<223> OTHER INFORMATION: Synthetic oligonucleotide

<400> SEQUENCE: 27
gtaatgcaga agaagaccat                                               20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
gccgagggcc gccactccac                                               20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
ccatgccgcc ggtggagtgg                                               20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
ctacaacgtc aacatcaagt                                               20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
caacttgatg ttgacgttgt                                               20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
tgaagggcga gatcaagcag                                               20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
tctgcttgat ctcgcccttc 20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
gacccaggac tcctccctgc 20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
gaactcgccg tcctgcaggg 20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
cttgaagctg tccttccccg 20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
ccacttgaag ccctcgggga 20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
gaagggcagg gggccaccct 20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
aagctgaagg tgaccaaggg 20

<210> SEQ ID NO 40
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 40
gggcgagggc cgcccctacg                                                  20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
tctgggtgcc ctcgtagggg                                                  20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
ctcgaactcg tggccgttca                                                  20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
catgcgcttc aaggtgcaca                                                  20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
ggataacatg gccatcatca                                                  20

<210> SEQ ID NO 45
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 45
gttcaatctg atttcttta tgg                                               23

<210> SEQ ID NO 46
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 46
tagattgtct aaagttgaga tgg                                              23
```

<210> SEQ ID NO 47
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 47
gtttctaaag gttatctctt agg					23

<210> SEQ ID NO 48
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 48
tcgatttcgc tatcaaattc tgg					23

<210> SEQ ID NO 49
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 49
gtaatgcaga agaagaccat ggg					23

<210> SEQ ID NO 50
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 50
tgtcccctca gttcatgtac gg					22

<210> SEQ ID NO 51
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 51
gcctcaacac gaacagagaa agg					23

<210> SEQ ID NO 52
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 52
ggagccgtac atgaactgag gg					22

<210> SEQ ID NO 53
<211> LENGTH: 22
<212> TYPE: DNA
<213> ORGANISM: Artificial sequence
<220> FEATURE:
<223> OTHER INFORMATION: Synthetic oligonucleotide -continued

<210> SEQ ID NO 53
<400> SEQUENCE: 53
tcgtgaccac cctgacctac gg                                           22

<210> SEQ ID NO 54
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 54
gtgaaccgca tcgagctgaa ggg                                          23

<210> SEQ ID NO 55
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 55
ctgaagcact gcacgccgta gg                                           22

<210> SEQ ID NO 56
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes Thr or Ser.
<220> FEATURE:
<221> NAME/KEY: MISC_FEATURE
<222> LOCATION: (9)..(9)
<223> OTHER INFORMATION: Xaa denotes Arg or Gln.

<400> SEQUENCE: 56

Xaa Lys Lys Ser Lys Lys Asn Leu Xaa Arg Leu
1               5                   10

<210> SEQ ID NO 57
<211> LENGTH: 11
<212> TYPE: PRT
<213> ORGANISM: Artificial sequence
<220> FEATURE:
<223> OTHER INFORMATION: Synthetic peptide

<400> SEQUENCE: 57

Thr Lys Lys Ser Lys Lys Asn Leu Arg Arg Leu
1               5                   10

<210> SEQ ID NO 58
<211> LENGTH: 13
<212> TYPE: PRT
<213> ORGANISM: Artificial sequence
<220> FEATURE:
<223> OTHER INFORMATION: Synthetic peptide

<400> SEQUENCE: 58

Thr Ser Met Thr Asp Phe Tyr His Ser Lys Arg Arg Leu
1               5                   10

<210> SEQ ID NO 59
<211> LENGTH: 13

```
<212> TYPE: PRT
<213> ORGANISM: Artificial sequence
<220> FEATURE:
<223> OTHER INFORMATION: Synthetic peptide

<400> SEQUENCE: 59

Pro Leu Ile Ser Asp Phe Phe Ala Lys Arg Lys Arg Ser
1               5                   10

<210> SEQ ID NO 60
<211> LENGTH: 12
<212> TYPE: PRT
<213> ORGANISM: Artificial sequence
<220> FEATURE:
<223> OTHER INFORMATION: Synthetic peptide

<400> SEQUENCE: 60

Arg Arg Val Thr Asp Phe Phe Ala Arg Arg Arg Pro
1               5                   10

<210> SEQ ID NO 61
<211> LENGTH: 12
<212> TYPE: PRT
<213> ORGANISM: Artificial sequence
<220> FEATURE:
<223> OTHER INFORMATION: Synthetic peptide

<400> SEQUENCE: 61

Arg Lys Leu Thr Asp Phe Tyr Pro Val Arg Arg Ser
1               5                   10

<210> SEQ ID NO 62
<211> LENGTH: 10
<212> TYPE: PRT
<213> ORGANISM: Artificial sequence
<220> FEATURE:
<223> OTHER INFORMATION: Synthetic peptide

<400> SEQUENCE: 62

Glu Pro Glu Glu Pro Glu Ala Asp Gln His
1               5                   10

<210> SEQ ID NO 63
<211> LENGTH: 10
<212> TYPE: PRT
<213> ORGANISM: Artificial sequence
<220> FEATURE:
<223> OTHER INFORMATION: Synthetic peptide

<400> SEQUENCE: 63

Glu Cys Glu Glu Thr Glu Val Asp Gln His
1               5                   10

<210> SEQ ID NO 64
<211> LENGTH: 14
<212> TYPE: PRT
<213> ORGANISM: Artificial sequence
<220> FEATURE:
<223> OTHER INFORMATION: Synthetic peptide

<400> SEQUENCE: 64

Leu Ala Pro Tyr Ile Pro Met Asp Gly Glu Asp Phe Gln Leu
1               5                   10

<210> SEQ ID NO 65
<211> LENGTH: 14
<212> TYPE: PRT
```

<213> ORGANISM: Artificial sequence
<220> FEATURE:
<223> OTHER INFORMATION: Synthetic peptide

<400> SEQUENCE: 65

Leu Ala Pro Ala Ala Gly Asp Thr Ile Ile Ser Leu Asp Phe
1               5                   10

<210> SEQ ID NO 66
<211> LENGTH: 15
<212> TYPE: PRT
<213> ORGANISM: Artificial sequence
<220> FEATURE:
<223> OTHER INFORMATION: Synthetic peptide

<400> SEQUENCE: 66

Gly Gly Gly Gly Ser Gly Gly Gly Gly Ser Gly Gly Gly Gly Ser
1               5                   10                  15

<210> SEQ ID NO 67
<211> LENGTH: 4494
<212> TYPE: DNA
<213> ORGANISM: Artificial sequence
<220> FEATURE:
<223> OTHER INFORMATION: Synthetic polynucleotide

<400> SEQUENCE: 67

```
atggactata aggaccacga cggagactac aaggatcatg atattgatta caaagacgat      60
gacgataaga tggccccaaa gaagaagcgg aaggtcggta tccacggagt cccagcagcc     120
gacaagatac agcatcggcc tggacatcgg caccaactct gtgggctggg ccgtgatcac     180
cgacgagtac aaggtgccca gcaagaaatt caaggtgctg gcaacaccga ccggcacag      240 catcaagaag aactatcgga gccctgctgt tcgacagcgg cgaaacagcc gaggccaccc     300
ggctgaagag aaccgccaga gaagatacac cagacggaa gaaccggatc tgctatctgc     360
aagagatctt cagcaacgaa tgccaaggtg acgacagct tcttccacag actgaagag      420 tccttcctgg tggaagagga taagaagcac gagcggcacc ccatcttcgg caacatcgtg     480
gacgaggtgg cctaccacga gaagtcccac atctaccac ctgagaaaga actggtgga     540 cagcaccgac aaggccgacc tgcggctgat ctatctggcc ctggcccaca tgatcaagtt     600
ccggggccac ttcctgatcg agggcgacct gacccgacaa cagcgacgtg acaagctgt     660 tcatccagct ggtgcagacc tacaaccagc tgttcgagga aaaccccatc aacgccagcg     720
gcgtggacgc caaggccatc ctgtctgcca gactgagaag agagacggct ggaaaatctg     780
atcgcccagc tgcccggcga aaagaagaat ggcctgttcg aaacctgat tgccctgagc     840 ctgggcctga cccccaactt caagagcaac ttcgacctgg ccgggatgca aactgcagct     900
gagcaaggac acctacgacg acgacctgga caacctgctg gcccagatcg cgaccagta     960 cgccgacctg tttctggccg ccaagaacct gtccgacgcc atcctgctgg cgacatctga    1020
gagtgaacac cgagatcacc aaggcccccc tgagcgcctc tatgatcaag agatacgacg    1080
agcaccacca ggacctgacc ctgctgaaag ctctcgtgcg gcagcagctg cctgaaagta    1140
caagagattt tcttcgacca gagcaagaac ggctacgccg ctacattga cggcggagcc    1200 agccaggaag agttctacaa gttcatcaag cccatcctgg aaaagatgga cggcaccgag    1260
gactgctcgt aagctgaaca gagaggacct gctgcggaag cagcggacct tcgacaacgg    1320
cagcatcccc caccagatcc acctgggaga gctgcacgcc attctgcggc ggcaggaaga    1380 ttttttaccat tcctgaagac aaccgggaaa agatcgagaa gatcctgacc ttccgcatcc    1440
```

```
cctactacgt gggccctctg gccaggggaa acagcagatt cgcctggatg accagaaaga    1500
gcgaggaaac catacccct ggaattcgag gaagtggtgg acaagggcgc ttccgcccag     1560
agcttcatcg agcggatgac caacttcgat aagaacctgc caacgagaa ggtgctgccc     1620 aagcacagcc tgctgtacgg tacttcaccg ttataacgag ctgaccaaag tgaaatacgt    1680
gaccgaggga atgagaaagc ccgccttcct gagcggcgag cagaaaaagg ccatcgtgga    1740
cctgctgttc aagaccaacc ggaaatgacc gtgaagcact gaaagaggac tacttcaaga    1800
aaatcgagtg cttcgactcc gtggaaatct ccggcgtgga agatcggttc aacgcctccc    1860
tgggcacata ccacgatctg ctgaaaatta tcaaggacaa ggacttcctg gacaatgagg    1920
aaaacgagga cattctggaa gatatcgtgc tgaccctgac actgtttgga cagagagatg    1980
atcgaggaac ggctgaaaac ctatgcccac ctgttcgacg acaaagtgat gaagcagctg    2040
aagcggcgga gatacaccgg ctggggcagg ctgagccgga agctgatcaa cggaccggga    2100
caagcagtcc ggcaagacaa tcctggattt cctgaagtcc gacggcttcg ccaacagaaa    2160
cttcatgcag ctgatccacg acgacagcct gacctttaaa gaggacatcc agaaagcccg    2220
ggtccggcca gggcgatagc ctgcacgagc acattgccaa tctggccggc agccccgcca    2280
ttaagaaggg catcctgcag acagtgaagg tggtggacga gctcgtgaaa gtgatgggcc    2340
ggcacagccg agaacatcgt gatcgaaatg gccagagaga accagaccac ccagaaggga    2400
cagaagaaca gccgcgagag aatgaagcgg atcgagagg gcatcaaaga gctgggcagc    2460
cagatcctga agaaccccg tggaaaaacac ccagctgcag aacgagaagc tgtacctgta    2520
ctacctgcag aatgggcggg atatgtacgt ggaccaggaa ctggacatca accggctgtc    2580
cgactacgat gtggacctat cggcctcaga gctttctgaa ggcgactcc atcgacaaca    2640 aggtgctgac cagaagcgac aagaaccggg gcaagagcga caacgtgccc tccgaagagg    2700
tcgtgaagaa gatgaagaac tacgcggcg ctgctgaacg ccaagctgat tacccagaga    2760
aagttcgaca atctgaccaa ggccgagaga ggcggcctga gcgaactgga taaggccggc    2820
ttcatcaaga acagctggt ggaaacccgc agatcaaaag cacgtggcac agatcctgga    2880
ctcccggatg aacactaagt acgacgagaa tgacaagctg atccgggaag tgaaagtgat    2940
caccctgaag tccaagctgg tgtccgattt ccggaggatt ccgttttac aaagtgcgcg    3000 agatcaacaa ctaccaccac gcccacgacg cctacctgaa cgccgtcgtg ggaaccgccc    3060
tgatcaaaaa gtaccctaag ctggaaagcg agttcgtgta cgcgactaca ggtgtacgac    3120
gtgcggaaga tgatcgccaa gagcgagcag gaaatcggca aggctaccgc caagtacttc    3180
ttctacagca acatcatgaa cttttttcaag accgagatta ccctggcaac ggcgagaccg    3240
gaagcggcct ctgatcgaga caaacggcga accggggga atcgtgtggg ataagggccg    3300
ggattttgcc accgtgcgga aagtgctgag catgccccaa gtgaatatcg tgaaaagacc    3360
gagggcagac aggcggcttc agcaaagagt ctatcctgcc caagaggaac agcgataagc    3420
tgatcgccag aaagaaggac tgggacccta agaagtacgg cggcttcgac agccccacct    3480
ggcctattct ggctggtggt ggccaaagtg gaaaagggca gtccaagaa actgaagagt    3540 gtgaaagagc tgctggggat caccatcatg gaaagaagca gcttcgagaa gatcccatc    3600 gacttctgga agccaaggct acaaagaagt gaaaaaggac ctgatcatca agctgcctaa    3660
gtactccctg ttcgagctgg aaaacggccg gaagagaatg ctggcctctg ccggcgaact    3720
gcagaaggga acgaactggc cctgcctcca aatatgtgaa cttcctgtac ctggccagcc    3780
```

| | |
|---|---|
| actatgagaa gctgaagggc tcccccgagg ataatgagca gaaacagctg tttgtggaac | 3840 |
| agcacaagca ctacctgacg agatcatcga gcgatcagcg agttctccaa gagagtgatc | 3900 |
| ctggccgacg ctaatctgga caaagtgctg tccgcctaca acaagcaccg ggataagccc | 3960 |
| atcagagagc aggccgagaa tatatccacc tgtttacccg accaatctgg gagcccctgc | 4020 |
| cgccttcaag tactttgaca ccaccatcga ccggaagagg tacaccagca ccaaagaggt | 4080 |
| gctggacgcc accctgatcc accagagcac accggcctgt acgagaacgg atcgacctgt | 4140 |
| ctcagctggg aggcgacaaa aggccggcgg ccacgaaaaa ggccggccag caaaaaaga | 4200 |
| aaaaggggag tggcggttct ggaccttccc ctgctggcct gctctgcgcg ctcagcttct | 4260 |
| gccacatctg ggagtcgaaa acgcgctcga cctcccgccg ctccgggacg cgaccaggcc | 4320 |
| aggcctcccg ccagacggcg gctgcgactg tccgtggacg agtgagctca ccctccacac | 4380 |
| tgaagcccct gatatccccg cttgtccatc tcctgggcag aaaatcaaaa agagcacccc | 4440 |
| ggctgcaggg cagcctccac accttacttc tgcccaagat caggatacat ctaa | 4494 |

<210> SEQ ID NO 68
<211> LENGTH: 5357
<212> TYPE: DNA
<213> ORGANISM: Artificial sequence
<220> FEATURE:
<223> OTHER INFORMATION: Synthetic polynucleotide

<400> SEQUENCE: 68

| | |
|---|---|
| acccacgcgc cggactcggc ccggaactct gcgtctcagg ggcggggagg acgagtcagg | 60 |
| agggacagtg cgcgcgcgcg ggagaccggc ggatgacggg ttcttaactc cgggccctcc | 120 |
| cgtgcctctc cagtcaagcc cggccgccga tcattgcgat ctgccctgct gacattccac | 180 |
| ttgggcggcc catgccgctc ctcccggccc cgcacgctca gaatccttca ggcgctcgcg | 240 |
| ccaagattct cccctcagcg agcccgcccc gcagccgcgc gcgccagacg actctcccgc | 300 |
| gtcccgcccc gcgcaggccc cgcctaccac gtccgcaccc cgcccccggc gcgcaggccc | 360 |
| tgacatctag ccccacccct tgtgcatgcc acgcccgtaa agaacacgc ccccgggag | 420 |
| gccacgcccc caccagagct cctcgctggt ccgcgcggcg acggggcggg ccccgggcct | 480 |
| gcggcggccg ctgaggggct cgcagccctc ggggcggggc gcgagggcgg gacggggccg | 540 |
| gtgccgcgcg ctgggatttt taaatgtccc gctcgaagcc gggcgcagga gcagccggct | 600 |
| cgacagccag cggtgtaggg ggcaggcgcg gatcccgcca gcgccgcgcg ctcggccgcc | 660 |
| gcctcccgcc tcctgcttcc cgctcgccgt cggcctcctg cccgctcgag cgcgcctgcc | 720 |
| tgcggcggac acagctgggt acgggctgcc tggactcccg ggactcccgg gactcccacg | 780 |
| actcccaggc gtccggatgg actataagga ccacgacgga gactacaagg atcatgatat | 840 |
| tgattacaaa gacgatgacg aaaatggccc caaagaagaa gcggaaggtc ggtatccacg | 900 |
| gagtcccagc agccgacaag aagtacagca tcggcctgga catcggcacc aactctgtgg | 960 |
| gctgggccgt gatcaccgac gagtacaggt cccagcaaga aattcaaggt gctgggcaac | 1020 |
| accgaccggc acagcatcaa gaagaacctg atcggagccc tgctgttcga cagcggcgaa | 1080 |
| acagccgagg ccacccggct gaagagaacc gccgaagaga taccagac ggaagaaccg | 1140 |
| gatctgctat ctgcaagaga tcttcagcaa cgagatggcc aaggtggacg acagcttctt | 1200 |
| ccacagactg gaagagtcct tcctggtgga agaggtaaa agcagagcgg caccccatct | 1260 |
| tcggcaacat cgtggacgag gtggcctacc acgaagagta ccccaccatc taccacctga | 1320 |
| gaaagaaact ggtggacagc accgacaagg ccgacctgcg gctgactatc tgccctggcc | 1380 |

```
cacatgatca agttccgggg ccacttcctg atcgagggcg acctgaaccc cgacaacagc    1440
gacgtggaca agctgttcat ccagctggtg cagacctaca accagctgtt caggaaaacc    1500
catcaacgcc agcggcgtgg acgccaaggc catcctgtct gccagactga gcaagagcag    1560
acggctggaa aatctgatcg cccagctgcc cggcgagaag aagaatggcc tgttcggaac    1620
ctgatgccct gagcctgggc ctgaccccca acttcaagag caacttcgac ctggccgagg    1680
atgccaaact gcagctgagc aaggacacct acgacgacga cctggacaac ctgctggccc    1740
agacggcgac catacgccga cctgtttctg gccgccaaga acctgtccga cgccatcctg    1800
ctgagcgaca tcctgagagt gaacaccgag atcaccaagg ccccctgag cgcctctatg     1860 atcaagagaa cgacgagcac accaggacct gaccctgctg aaagctctcg tgcggcagca    1920
gctgcctgag aagtacaaag agatttttctt cgaccagaga aagaacggct acgccggcta    1980
cattgacggc ggagcagcca ggaagattct acaagttcat caagcccatc ctggaaaaga    2040
tggacggcac cgaggaactg ctcgtgaagc tgaacagaga ggacctgctg cggaagcagc    2100
ggaccttcga caacggcagc accccccacca gatcacctgg gagagctgca cgccattctg    2160
cggcggcagg aagatttttta cccattcctg aaggacaacc gggaaaagat cgagaagatc    2220 ctgacctttcc gcatccccta ctacgtggcc ctctggccag ggaaacagca gattcgcctg    2280
gatgaccaga aagagcgagg aaaccatcac cccctggaac ttcgaggaag tggtggacaa    2340
gggcgcttcc gcccagagct tcatcgagcg gataccaact tcgataaaac ctgcccaacg    2400
agaaggtgct gcccaagcac agcctgctgt acgagtactt caccgtgtat aacgagctga    2460
ccaaagtgaa atacgtgacc gagggaatga aaagcccgc ttcctgagcg gcgacagaaa     2520
aaggccatcg tggacctgct gttcaagacc aaccggaaag tgaccgtgaa gcagctgaaa    2580
gaggactact tcaagaaaat cgagtgcttc gactccgtgg aaatcccggc gtggaagatc    2640
gttcaacgcc tccctgggca catacccaga tctgctgaaa attatcaagg acaaggactt    2700
cctggacaat gaggaaaacg aggacattct ggaagatatc gtgctgaccc tacactgttt    2760
gaggacagga gatgatcgag gaacggctga aaacctatgc ccacctgttc gacgacaaag    2820
tgatgaagca gctgaagcgg cggagataca ccggctgggg caggctgagc cggaagcgat    2880
caacggcatc cgggaaagca gtccggcaag acaatcctgg atttcctgaa gtccgacggc    2940
ttcgccaaca gaaacttcat gcagctgatc cacgacgaca gcctgacctt taaagaggac    3000
atcagaaagc ccaggtgtcc ggcagggcga tagcctgcac gagcacattg ccaatctggc    3060
cggcagcccc gccattaaga agggcatcct gcagacagtg aaggtggtgg acgagctcgt    3120
gaaagtgatg ggccggcacaa gcccgagaaa tcgtgatcga aatggccaga gagaaccaga    3180
ccacccagaa gggacagaag aacagccgcg agagaatgaa gcggatcgaa gagggcatca    3240 agagctggg cagccgatcc tgaaagaaca ccccgtgaaa cacccagct gcagaacgag      3300 aagctgtacc tgtactacct gcagaatggg cgggatatgt acgtggacca ggaactggac    3360
atcaaccggc tgtccgacta catgtggacc atatcgtgcc tcaagctttc tgaaggacga    3420
ctccatcgac aacaaggtgc tgaccagaag cgacaagaac cggggcaaga gcgacaacgt    3480 gcctccgaa gaggtcgtga agaagataag aactactggc ggcagctgct aacgccaagc     3540 tgattacccca gagaaagttc gacaatctga ccaaggccga gagggcggc ctgagcgaac    3600 tggataaggc cggcttcatc aagagacagc tggggaaacc cggcagatca caaagcagtg    3660
gcacagatcc tggactcccg gatgaacact aagtacgacg agaatgacaa gctgatccgg    3720
```

```
gaagtgaaag tgatcaccct gaagtccaag ctggtgtcca tttccggaag gatttccagt      3780
tttacaaagt gcgcgagatc aacaactacc accacgccca cgacgcctac ctgaacgccg      3840
tcgtgggaac cgccctgatc aaaaagtacc ctaagctgga aagcgagttc gtgtacggcg      3900
actacaaggt gtcgacgtgc ggaagatgat cgccaagagc gagcaggaaa tcggcaaggc      3960
taccgccaag tacttcttct acagcaacat catgaacttt ttcaagaccg agattaccct      4020
ggccaacggc gagatccgga gcggcctctg atcgagacaa acggcgaaac cggggagatc      4080
gtgtgggata agggccggga ttttgccacc gtgcggaaag tgctgagcat gccccaagtg      4140
aatatcgtga aaaagaccga ggtgcaacag gcggcttcag caaagagtct atcctgccca      4200
agaggaacag cgataagctg atcgccagaa agaaggactg ggaccctaag aagtacggcg      4260
gcttcgacag ccccaccgtg gcctattctg tgcggtggtg gccaaagtgg aaagggcaa      4320 gtccaagaaa ctgaagagtg tgaaagagct gctgggatc accatcatgg aaagaagcag      4380
cttcgagaag aatcccatcg actttctgga agccaagggc acaagaagt gaaaaaggac      4440 ctgatcatca agctgcctaa gtactccctg ttcgagctgg aaaacggccg gaagagaatg      4500
ctggcctctg ccggcgaact gcagaaggga acgaactgg ccctgcctcc aaatatgtga      4560
acttcctgta cctggccagc cactatgaga agctgaaggg ctcccccgag ataatgagc      4620 agaaacagct gtttgtggaa cagcacaagc actacctgga cgagatcatc gagcgatcag      4680
cgagttctcc aagagagtga tcctggccga cgctaatctg acaaagtgc tgtccgccta      4740 caacaagcac cgggataagc ccatcagaga gcaggccgag aatatcatcc acctgtttac      4800
ctgaccaatc tgggagcccc tgccgccttc aagtactttg acaccaccat cgaccggaag      4860
aggtacacca gcaccaaaga ggtgctggac gccaccctga tccaccagag catcaccggc      4920
ctgtacgaac acgatcgac ctgtctcagc tgggaggcga caaaaggccg gcggccacga      4980
aaaaggccgg ccaggcaaaa aagaaaaagg ggagtggcgg ttctggaatg aatcccagta      5040
tgaagcagaa acaagagaaa tcaaagagaa tataaagaat agttctgtcc aagaagaac      5100 tctgaagatg attcagcctt ctgcatctgg atctcttgtt ggaagagaaa atgagctgtc      5160
cgcaggcttg tccaaaagga aaatcggaat gaccacttaa catctacaac ttccagccct      5220
ggggttattg tcccagaatc tagtgaaaat aaaaatcttg gaggagtcac ccaggagtca      5280
tttgatctta tgattaaaga aaatccatct ctcagtattg gaaggaagtg gcagaaaaac      5340
ggagaaaggc gctgtaa                                                   5357

<210> SEQ ID NO 69
<211> LENGTH: 5479
<212> TYPE: DNA
<213> ORGANISM: Artificial sequence
<220> FEATURE:
<223> OTHER INFORMATION: Synthetic polynucleotide

<400> SEQUENCE: 69
taaggagttt gacatagaaa gatagagagt tgcaatagag atctttgtta aataagattt        60
tacaaaacta tattttggga gtaatcttaa acttagagca aaattaagca taaggcacat       120
tttcttttca ctggggcagt cgctattggg gagcttggta tgttaatcta tttgcttata       180
ataaccattt acagctgggc ggtggtggca cacgccttta atcccagcac ttgggaggca       240
gaggcaggtg gatttgagtt cgaggccagc ctggtataca gagtgagttt caggacagcc       300
aggcctatac agaaaaccc tgtctcgaaa aacaaaaag caaaacaaa acaaaaaaca       360 tttactatgt gtatgtgtgt aaacttcatg ctatcaacct caaaatccat cccagatagc       420
```

```
tgttggaaca gtcatattaa agaccgtctc tgcaacaaag ctttcgggaa ctcttaagat    480
agtattggca cttctataga agaggtgaaa acaataaata ggacaacagc aaaactgata    540
tgcgtactcc ccacagtcat tttcctaaag tccaacggag tcgcctgggc tagcttggac    600
agcacacaag tgagcactgc acgccatgcc tcctaggcag gtggcagcaa tgcgacttgt    660
gcgcaggcat agagcctgac ctcgcgaggg gtgggcggtg ctgccagcgg cagcctcgct    720
ctggccccgc ccccgcccca ccccgccga acttgggtcg cggatcgccc aggaaacgca    780
ttctacggga acccgcggcg ccaatgggaa gagagcgagt gccacgaact ggccaatgag    840
gagcgagcgc cccggggttt aaacctaagc ccggcagact cctccggcgg ctgcggagga    900
acggctgtta gtgtttagct gtggatagcc agaggttagg gtgtcttctc gaatcgggga    960
acctctgatt ttggaggagc catggactat aaggaccacg acggagactc aaggatatga    1020
tattgattac aaagacgatg acgataagat ggccccaaag aagaagcgga aggtcggtat    1080
ccacggagtc ccagcagccg acaagaagta cagcatcggc ctggacatcg gcaccactct    1140
gtggctgggc cgtgatcacc gacgagtaca aggtgcccag caagaaattc aaggtgctgg    1200
gcaacaccga ccggcacagc atcaagaaga acctgatcgg agccctgctg ttcgacagcg    1260
ggaaacagcc aggccacccg gctgaagaga accgccagaa gaagatacac cagacggaag    1320
aaccggatct gctatctgca agagatcttc agcaacgaga tggccaaggt ggacgacagc    1380
ttcttcccag actggaaagt ccttcctggt ggaagaggat aagaagcacg agcggcaccc    1440
catcttcggc aacatcgtgg acgaggtggc ctaccacgag aagtacccca ccatctacca    1500
cctgagaaag aaatggtgga cagcccgaca aggccgacct gcggctgatc tatctggccc    1560
tggcccacat gatcaagttc cggggccact cctgatcga gggcgacctg aaccccgaca    1620
acagcgacgt ggacaagctg ttcatccagc tggtgcagac ctacaaccag ctgttcgagg    1680
aaaaccatca cgccagcgg cgtggacgcc aaggccatcc tgtctgccag actgagcaag    1740
agcagacggc tggaaaatct gatcgcccag ctgcccggcg agaagaagaa tggcctgttc    1800
ggaaacctga tccctgagcc tgggcctgac ccccaacttc aagagcaact tcgacctggc    1860
cgaggatgcc aaactgcagc tgagcaagga cacctacgac gacgacctgg acaacctgct    1920
ggcccagatc ggcgacagac gccgacctgt ttctggccgc caagaacctg tccgacgcca    1980
tcctgctgag cgacatcctg agagtgaaca ccgagatcac caaggccccc ctgagcgcct    2040
ctatgatcaa gagatacgac gacacaccag gacctgaccc tgctgaaagc tctcgtgcgg    2100
cagcagctgc ctgagaagta caaagagatt ttcttcgacc agagcaagaa cggctacgcc    2160
ggctacattg acggcggagc cagccaggag agtctacaag ttcatcaagc ccatcctgga    2220
aaagatggac ggcaccgagg aactgctcgt gaagctgaac agagaggacc tgctgcggaa    2280
gcagcggacc ttcgacaacg gcagcatccc ccacagatca cctgggagag ctgcacgcca    2340
ttctgcggcg gcaggaagat ttttacccat tcctgaagga caaccgggaa aagatcgaga    2400
agatcctgac cttccgcatc ccctactacg tgggccctct gccagggaaa cagcagattc    2460
gcctggatga ccagaaagag cgaggaaacc atcacccccct ggaacttcga ggaagtggtg    2520
gacaagggcg cttccgccca gagcttcatc gagcggatga ccaactcgat aagacctgcc    2580
caacgagaag gtgctgccca agcacagcct gctgtacgag tacttcaccg tgtataacga    2640
gctgaccaaa gtgaaatacg tgaccgaggg aatgagaaag cccgccttcc tggcggcgag    2700
agaaaaaggc catcgtggac ctgctgttca agaccaaccg gaaagtgacc gtgaagcagc    2760
```

```
tgaaagagga ctacttcaag aaaatcgagt gcttcgactc cgtggaaatc tccggcgtga    2820
agatcggtca acgcctccct gggcacatac cacgatctgc tgaaaattat caaggacaag    2880
gacttcctgg acaatgagga aaacgaggac attctggaag atatcgtgct gaccctgaca    2940
ctgttgagga cagaagatga tcgaggaacg gctgaaaacc tatgcccacc tgttcgacga    3000
caaagtgatg aagcagctga agcggcggag atacaccggc tggggcaggc tgagccggaa    3060
gctgatcaac gcatccggga cagcagtccg gcaagacaat cctggatttc ctgaagtccg    3120
acggcttcgc caacagaaac ttcatgcagc tgatccacga cgacagcctg acctttaaag    3180
aggacatcca gaaagccagg tgtccggcag ggcgatagcc tgcacgagca cattgccaat    3240
ctggccggca gccccgccat taagaagggc atcctgcaga cagtgaaggt ggtggacgag    3300
ctcgtgaaag tgatgggccg gccaagcccg agaactcgtg atcgaaatgg ccagagagaa    3360
ccagaccacc cagaagggac agaagaacag ccgcgagaga atgaagcgga tcgaagaggg    3420
catcaaagag ctgggcagcc agatcctgaa gaacacccccg tgaaaacacc cagctgcaga    3480
acgagaagct gtacctgtac tacctgcaga atgggcggga tatgtacgtg gaccaggaac    3540
tggacatcaa ccggctgtcc gactacgatg tggacatatc gtgcctcagg ctttctgaag    3600
gacgactcca tcgacaacaa ggtgctgacc agaagcgaca gaaccggggg caagagcgac    3660
aacgtgccct ccgaagaggt cgtgaagaag atgaagaact ctggcggcag ctgctgacgc    3720
caagctgatt acccagagaa agttcgacaa tctgaccaag gccagagag gcggcctgag    3780 cgaactggat aaggccggct tcatcaagag acagctggtg aaaccggca gatcacaaag    3840 cactggcaca gatcctggac tcccggatga acactaagta cgacgagaat gacaagctga    3900
tccgggaagt gaaagtgatc accctgaagt ccaagctggt gtccgatttc gaaggattt    3960 ccagttttac aagtgcgcga gatcaacaac taccaccacg cccacgacgc ctacctgaac    4020
gccgtcgtgg aaccgccct gatcaaaaag taccctaagc tggaaagcga gttcgtgtcg    4080
gcgactacaa ggtgtacacg tgcggaagat gatcgccaag agcgagcagg aaatcggcaa    4140
ggctaccgcc aagtacttct tctacagcaa catcatgaac ttttcaaga ccgagattac    4200 cctgccaacg gcgagatccg gaagggcctc tgatcgagac aaacggcgaa accggggaga    4260
tcgtgtggga taagggccgg gattttgcca ccgtgcggaa agtgctgagc atgccccaag    4320
tgaatatcgt aaaagaccg aggtgcagac agcggcttca gcaaagagtc tatcctgccc    4380
aagaggaaca gcgataagct gatcgccaga aagaaggact gggaccctaa gaagtacggc    4440
ggcttcgaca gccccacgtg gcctattctg tgctggtgtg gccaaagtgg aaaagggcaa    4500
gtccaagaaa ctgaagagtg tgaaagagct gctggggatc accatcatgg aaagaagcag    4560
cttcgagaag aatcccatcg acttctggaa gccaagggct acaaaaagtg aaaaaggacc    4620
tgatcatcaa gctgcctaag tactccctgt tcgagctgga aaacggccgg aagagaatgc    4680
tggcctctgc cggcgaactg cagaagggaa cgaactggcc ctgccctcca aaatgtgaac    4740
ttcctgtacc tggccagcca ctatgagaag ctgaagggc ccccgagga taatgagcag    4800 aaacagctgt ttgtggaaca gcacaagcac tacctggacg agatcatcga gcagatcagc    4860
gagttctcca agagagtgat cctggccgac gctaatctgg acaaagtgct gtccgccaca    4920
acaagcaccg ggataagccc atcagagagc aggccgagaa tatcatccac ctgtttaccc    4980
tgaccaatct gggagcccct gccgccttca agtactttga caccaccatc gaccggaaga    5040
ggtaaccagc accaaagagg tgctggacgc caccctgatc caccagagca tcaccggcct    5100
gtacgagaca cggatcgacc tgtctcagct gggaggcgac aaaaggccgg cggccacgaa    5160
```

-continued

| | |
|---|---|
| aaaggccggc cggcaaaaaa gaaaaagggg agtggcggtt ctggaccttc ccctgctagg | 5220 |
| cctgctctgc gcgctccagc ttctgccaca tctgggagtc gaaaacgcgc tcgacctccc | 5280 |
| gccgctccgg gacgcgacag gccaggcctc ccgccagacg gcggctgcga ctgtccgtgg | 5340 |
| acgaggtgag ctcaccctcc acacctgaag cccctgatat ccccgcttgt ccatctcctg | 5400 |
| ggcagaaaat caaaagagc acccccgctgc agggcagcct ccacacctta cttctgccca | 5460 |
| agatcaggat accatctaa | 5479 |

<210> SEQ ID NO 70
<211> LENGTH: 5343
<212> TYPE: DNA
<213> ORGANISM: Artificial sequence
<220> FEATURE:
<223> OTHER INFORMATION: Synthetic polynucleotide

<400> SEQUENCE: 70

| | |
|---|---|
| acccacgcgc cggactcggc ccggaactct gcgtctcagg ggcggggagg acgagtcagg | 60 |
| agggacagtg cgcgcgcgcg ggagaccggc ggatgacggg ttcttaactc cgggccctcc | 120 |
| cgtgcctctc cagtcaagcc cggccgccga tcattgcgat ctgccctgct gacattccac | 180 |
| ttgggcggcc catgccgctc ctcccggccc cgcacgctca gaatccttca ggcgctcgcg | 240 |
| ccaagattct cccctcagcg agccgcccc gcagccgcgc gcgccagacg actctcccgc | 300 |
| gtcccgcccc gcgcaggccc cgcctaccac gtccgcaccc cgccccggc gcgcaggccc | 360 |
| tgacatctag ccccacccct tgtgcatgcc acgcccgtaa aagaacacgc ccccggggag | 420 |
| gccacgcccc caccagagct cctcgctggt ccgcgcggcg acgggcgggg cccgggcct | 480 |
| gcggcggccg ctgaggggct cgcagcctgg ggcggggcgc gagggcggga cggggccggt | 540 |
| gccgcgcgct gggattttta atgtcccgc tcgaagccgg gcgcaggagc agccggctcg | 600 |
| acagccagcg cggtgtaggg ggcaggcgcg gtccccccagc gccgcgcgct cggccgccgc | 660 |
| ctcccgcctc ctgcttcccg ctcgccgtcg gcctcctgcc cgctcgagcg cgcctgcctg | 720 |
| cggcggacac agcttcgggt acgggctgcc tggactccgg gatcccggga ctcccacgac | 780 |
| tcccaggcgt ccgatggac tataaggacc acgacgaga ctacaaggat catgatattg | 840 |
| attacaaaga cgatgacgat aagatggccc caaagaagaa gcgaaggtcg tatccacgga | 900 |
| gtcccagcag ccgacaagaa gtacagcatc ggcctgaca tcggcaccaa ctctgtgggc | 960 |
| tgggccgtga tcaccgacga gtacaaggtg cccagcaaga aattcaaggg ctgggcacac | 1020 |
| cgaccggcac agcatcaaga agaacctgat cggagccctg ctgttcgaca gcggcgaaac | 1080 |
| agccgaggcc acccggctga agagaaccgc cagaagaaga tacaccagac ggaagaccgg | 1140 |
| atcgctatct gcaagagatc ttcagcaacg agatggccaa ggtggacgac agcttcttcc | 1200 |
| acagactgga agagtccttc ctggtggaag aggataagaa gcacgagcgg caccccatct | 1260 |
| tggcaacatc tggacgaggt ggcctaccac gagaagtacc ccaccatcta ccacctgaga | 1320 |
| aagaaactgg tggacagcac cgacaaggcc gacctgcggc tgatctatct ggccctggcc | 1380 |
| cacatgacaa gttccggcc acttcctgat cgagggcgac ctgaaccccg acaacagcga | 1440 |
| cgtggacaag ctgttcatcc agctggtgca gacctacaac cagctgttcg aggaaaaccc | 1500 |
| catcaacgcc agcgcgtgga cgccaggcca tcctgtctgc cagactgagc aagagcagac | 1560 |
| ggctggaaaa tctgatcgcc cagctgcccg gcgagaagaa gaatggcctg ttcggaaacc | 1620 |
| tgattgccct gagcctgggc tgaccccaa ctcaagagca acttcgacct ggccgaggat | 1680 |

```
gccaaactgc agctgagcaa ggacacctac gacgacgacc tggacaacct gctggcccag    1740
atcggcgacc agtacgccga cctgttctgg ccgccaagac ctgtccgacg ccatcctgct    1800
gagcgacatc ctgagagtga acaccgagat caccaaggcc cccctgagcg cctctatgat    1860
caagagatac gacgagcacc accaggacct gccctgctga agcttcgtg cggcagcagc     1920
tgcctgagaa gtacaaagag attttcttcg accagagcaa gaacggctac gccggctaca    1980
ttgacggcgg agccagccag gaagagttct acaagttatc aagcccatcc tgaaaagatg    2040
gacggcaccg aggaactgct cgtgaagctg aacagagagg acctgctgcg gaagcagcgg    2100
accttcgaca acggcagcat cccccaccag atccacctgg aggctgcac gccattctgg     2160
gcggcaggaa gatttttacc cattcctgaa ggacaaccgg gaaaagatcg agaagatcct    2220
gaccttccgc atcccctact acgtgggccc tctggccagg ggaaacagcg attcgcctgg    2280
atgaccgaaa gagcgaggaa accatcaccc cctggaactt cgaggaagtg gtggacaagg    2340
gcgcttccgc ccagagcttc atcgagcgga tgaccaactt cgataagaac ctgccaacga    2400
gaaggtgctg cccagcacag cctgctgtac gagtacttca ccgtgtataa cgagctgacc    2460
aaagtgaaat acgtgaccga gggaatgaga agcccgcct tcctgagcgg cgagcagaaa     2520
aggccatcgt ggacctgctg ttcaagacca accggaaagt gaccgtgaag cagctgaaag    2580
aggactactt caagaaaatc gagtgcttcg actccgtgga aatctccggc gtggaagatc    2640
ggttcaacgc ctccctgggc acataacgat ctgctgaaaa ttatcaagga caaggacttc    2700
ctggacaatg aggaaaacga ggacattctg gaagatatcg tgctgaccct gacactgttt    2760
gaggacagag agatgatcga ggaacggctg aacctatgcc cacctgttcg acgacaaagt    2820
gatgaagcag ctgaagcggc ggagatacac cggctggggc aggctgagcc ggaagctgat    2880
caacggcatc cgggacaagc agtccggcaa gacaatctga tttcctgaag tccgacggct    2940
tcgccaacag aaacttcatg cagctgatcc acgacgacag cctgaccttt aaagaggaca    3000
tccagaaagc ccaggtgtcc ggccagggcg atagcctgca cgacacttgc caatctggcc    3060
ggcagccccg ccattaagaa gggcatcctg cagacagtga aggtggtgga cgagctcgtg    3120
aaagtgatgg ccggcacaa gcccgagaac atcgtgatcg aaatggccaa gagaccagac    3180
cacccagaag ggacagaaga acagccgcga gagaatgaag cggatcgaag agggcatcaa    3240
agagctgggc agccagatcc tgaaagaaca ccccgtggaa acacccagc tgcagacgag     3300
agctgtacct gtactacctg cagaatgggc gggatatgta cgtggaccag gaactggaca    3360
tcaaccggct gtccgactac gatgtggacc atatcgtgcc tcagagcttt ctgaaggacg    3420
atccatcaca acaaggtgct gaccagaagc gacaagaacc ggggcaagag cgacaacgtg    3480
ccctccgaag aggtcgtgaa gaagatgaag aactactggc ggcagctgct gaacgccaag    3540
ctgattacca gagaagttcg acaatctgac caaggccgag agaggcggcc tgagcgaact    3600
ggataaggcc ggcttcatca agagacagct ggtggaaacc cggcagatca caaagcacgt    3660
ggcacagatc ctgactcccg tgaacactaa gtacgacga gaatgacaag ctgatccggg     3720
aagtgaaagt gatcacctg aagtccaagc tggtgtccga tttccggaag gatttccagt     3780
tttacaaagt gcgcgagata caactacac cacgcccacg acgcctacct gaacgccgtc     3840
gtgggaaccg ccctgatcaa aaagtaccct aagctggaaa gcgagttcgt gtacggcgac    3900
tacaaggtgt acgacgtgcg gaagagatcg ccaaggcgag caggaaatcg caaggctac    3960
cgccaagtac ttcttctaca gcaacatcat gaactttttc aagaccgaga ttaccctggc    4020
caacggcgag atccggaagc ggcctctgat cagacaaacg gcaaaccggg gagatcgtgt    4080
```

```
gggataaggg ccgggatttt gccaccgtgc ggaaagtgct gagcatgccc caagtgaata    4140
tcgtgaaaaa gaccgaggtg cagacaggcg gcttcagaaa gagtctatct gcccaagagg    4200
aacagcgata agctgatcgc cagaaagaag gactgggacc ctaagaagta cggcggcttc    4260
gacagcccca ccgtggccta ttctgtgctg gtggtggcca agggaaaag ggcaagccaa    4320 gaaactgaag agtgtgaaag agctgctggg gatcaccatc atggaaagaa gcagcttcga    4380
gaagaatccc atcgactttc tggaagccaa gggctacaaa gaagtgaaaa ggaccctgatc   4440 atcagctgcc taagtactcc ctgttcgagc tggaaaacgg ccggaagaga atgctggcct    4500
ctgccggcga actgcagaag ggaaacgaac tggccctgcc ctccaaatat gtgaattcct    4560
gtacctggcc gccactatga aagctgaag ggctcccccg aggataatga gcagaaacag     4620
ctgtttgtgg aacagcacaa gcactacctg gacgagatca tcgagcagat cagcgagttc    4680
tcaagagagt gatcctgccg acgctaatct ggacaaagtg ctgtccgcct acaacaagca    4740
ccgggataag cccatcagag agcaggccga gaatatcatc acctgtttta ccctgaccaa    4800
tctgggaccc ctgccgcctt caagactttg acaccaccat cgaccggaag aggtacacca    4860
gcaccaaaga ggtgctggac gccaccctga tccaccagag catcaccggc ctgtacgaga    4920
cacggatcga ccttctcagc tgggaggcga caaaggccgg cggccacgaa aaaggccggc    4980
caggcaaaaa agaaaaggg gagtggcggt tctggaatga atcccagtat gaagcagaaa    5040
caagaagaaa tcaaagagat ataaagaata gttctgtcca gaagaactc tgaagatgat     5100 tcagccttct gcatctggat ctcttgttgg aagagaaaat gagctgtccg caggcttgtc    5160
caaaaggaaa catcggaatg accactaaca tctacaactt ccagcctggg gttattgtcc    5220
cagaatctag tgaaaataaa aatcttggag gagtcaccca ggagtcattt gatcttatga    5280
ttaaagaaaa tccatcctct cagtattgga agaagtggca gaaaacgga gaaggcgctg      5340 taa                                                                  5343
```

<210> SEQ ID NO 71
<211> LENGTH: 1520
<212> TYPE: PRT
<213> ORGANISM: Artificial sequence
<220> FEATURE:
<223> OTHER INFORMATION: Synthetic polypeptide

<400> SEQUENCE: 71

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
            20                  25                  30

Gly Ile His Gly Val Pro Ala Ala Asp Lys Lys Tyr Ser Ile Gly Leu
        35                  40                  45

Asp Ile Gly Thr Asn Ser Val Gly Trp Ala Val Ile Thr Asp Glu Tyr
    50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Tyr Thr
            100                 105                 110

Arg Arg Lys Asn Arg Ile Cys Tyr Leu Gln Glu Ile Phe Ser Asn Glu
        115                 120                 125
```

```
Met Ala Lys Val Asp Asp Ser Phe Phe His Arg Leu Glu Glu Ser Phe
130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
                180                 185                 190

Ile Tyr Leu Ala Leu Ala His Met Ile Lys Phe Arg Gly His Phe Leu
            195                 200                 205

Ile Glu Gly Asp Leu Asn Pro Asp Asn Ser Asp Val Asp Lys Leu Phe
210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
                260                 265                 270

Lys Asn Gly Leu Phe Gly Asn Leu Ile Ala Leu Ser Leu Gly Leu Thr
            275                 280                 285

Pro Asn Phe Lys Ser Asn Phe Asp Leu Ala Glu Asp Ala Lys Leu Gln
290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
                340                 345                 350

Lys Ala Pro Leu Ser Ala Ser Met Ile Lys Arg Tyr Asp Glu His His
            355                 360                 365

Gln Asp Leu Thr Leu Leu Lys Ala Leu Val Arg Gln Gln Leu Pro Glu
370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
                420                 425                 430

Asn Arg Glu Asp Leu Leu Arg Lys Gln Arg Thr Phe Asp Asn Gly Ser
            435                 440                 445

Ile Pro His Gln Ile His Leu Gly Glu Leu His Ala Ile Leu Arg Arg
450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
                500                 505                 510

Thr Pro Trp Asn Phe Glu Glu Val Val Asp Lys Gly Ala Ser Ala Gln
            515                 520                 525

Ser Phe Ile Glu Arg Met Thr Asn Phe Asp Lys Asn Leu Pro Asn Glu
530                 535                 540

Lys Val Leu Pro Lys His Ser Leu Leu Tyr Glu Tyr Phe Thr Val Tyr
```

```
            545                 550                 555                 560
Asn Glu Leu Thr Lys Val Lys Tyr Val Thr Glu Gly Met Arg Lys Pro
                    565                 570                 575

Ala Phe Leu Ser Gly Glu Gln Lys Lys Ala Ile Val Asp Leu Leu Phe
                    580                 585                 590

Lys Thr Asn Arg Lys Val Thr Val Lys Gln Leu Lys Glu Asp Tyr Phe
                    595                 600                 605

Lys Lys Ile Glu Cys Phe Asp Ser Val Glu Ile Ser Gly Val Glu Asp
                    610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                    645                 650                 655

Asp Ile Val Leu Thr Leu Thr Leu Phe Glu Asp Arg Glu Met Ile Glu
                    660                 665                 670

Glu Arg Leu Lys Thr Tyr Ala His Leu Phe Asp Asp Lys Val Met Lys
                    675                 680                 685

Gln Leu Lys Arg Arg Arg Tyr Thr Gly Trp Gly Arg Leu Ser Arg Lys
                    690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                    725                 730                 735

His Asp Asp Ser Leu Thr Phe Lys Glu Asp Ile Gln Lys Ala Gln Val
                    740                 745                 750

Ser Gly Gln Gly Asp Ser Leu His Glu His Ile Ala Asn Leu Ala Gly
                    755                 760                 765

Ser Pro Ala Ile Lys Lys Gly Ile Leu Gln Thr Val Lys Val Val Asp
                    770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                    805                 810                 815

Arg Glu Arg Met Lys Arg Ile Glu Glu Gly Ile Lys Glu Leu Gly Ser
                    820                 825                 830

Gln Ile Leu Lys Glu His Pro Val Glu Asn Thr Gln Leu Gln Asn Glu
                    835                 840                 845

Lys Leu Tyr Leu Tyr Tyr Leu Gln Asn Gly Arg Asp Met Tyr Val Asp
                    850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
                    885                 890                 895

Thr Arg Ser Asp Lys Asn Arg Gly Lys Ser Asp Asn Val Pro Ser Glu
                    900                 905                 910

Glu Val Val Lys Lys Met Lys Asn Tyr Trp Arg Gln Leu Leu Asn Ala
                    915                 920                 925

Lys Leu Ile Thr Gln Arg Lys Phe Asp Asn Leu Thr Lys Ala Glu Arg
                    930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
                    965                 970                 975
```

```
Arg Met Asn Thr Lys Tyr Asp Glu Asn Asp Lys Leu Ile Arg Glu Val
            980                 985                 990

Lys Val Ile Thr Leu Lys Ser Lys  Leu Val Ser Asp Phe  Arg Lys Asp
            995                 1000                1005

Phe Gln  Phe Tyr Lys Val Arg  Glu Ile Asn Asn Tyr  His His Ala
         1010                1015                1020

His Asp  Ala Tyr Leu Asn Ala  Val Val Gly Thr Ala  Leu Ile Lys
         1025                1030                1035

Lys Tyr  Pro Lys Leu Glu Ser  Glu Phe Val Tyr Gly  Asp Tyr Lys
         1040                1045                1050

Val Tyr  Asp Val Arg Lys Met  Ile Ala Lys Ser Glu  Gln Glu Ile
         1055                1060                1065

Gly Lys  Ala Thr Ala Lys Tyr  Phe Phe Tyr Ser Asn  Ile Met Asn
         1070                1075                1080

Phe Phe  Lys Thr Glu Ile Thr  Leu Ala Asn Gly Glu  Ile Arg Lys
         1085                1090                1095

Arg Pro  Leu Ile Glu Thr Asn  Gly Glu Thr Gly Glu  Ile Val Trp
         1100                1105                1110

Asp Lys  Gly Arg Asp Phe Ala  Thr Val Arg Lys Val  Leu Ser Met
         1115                1120                1125

Pro Gln  Val Asn Ile Val Lys  Lys Thr Glu Val Gln  Thr Gly Gly
         1130                1135                1140

Phe Ser  Lys Glu Ser Ile Leu  Pro Lys Arg Asn Ser  Asp Lys Leu
         1145                1150                1155

Ile Ala  Arg Lys Lys Asp Trp  Asp Pro Lys Lys Tyr  Gly Gly Phe
         1160                1165                1170

Asp Ser  Pro Thr Val Ala Tyr  Ser Val Leu Val Val  Ala Lys Val
         1175                1180                1185

Glu Lys  Gly Lys Ser Lys Lys  Leu Lys Ser Val Lys  Glu Leu Leu
         1190                1195                1200

Gly Ile  Thr Ile Met Glu Arg  Ser Ser Phe Glu Lys  Asn Pro Ile
         1205                1210                1215

Asp Phe  Leu Glu Ala Lys Gly  Tyr Lys Glu Val Lys  Lys Asp Leu
         1220                1225                1230

Ile Ile  Lys Leu Pro Lys Tyr  Ser Leu Phe Glu Leu  Glu Asn Gly
         1235                1240                1245

Arg Lys  Arg Met Leu Ala Ser  Ala Gly Glu Leu Gln  Lys Gly Asn
         1250                1255                1260

Glu Leu  Ala Leu Pro Ser Lys  Tyr Val Asn Phe Leu  Tyr Leu Ala
         1265                1270                1275

Ser His  Tyr Glu Lys Leu Lys  Gly Ser Pro Glu Asp  Asn Glu Gln
         1280                1285                1290

Lys Gln  Leu Phe Val Glu Gln  His Lys His Tyr Leu  Asp Glu Ile
         1295                1300                1305

Ile Glu  Gln Ile Ser Glu Phe  Ser Lys Arg Val Ile  Leu Ala Asp
         1310                1315                1320

Ala Asn  Leu Asp Lys Val Leu  Ser Ala Tyr Asn Lys  His Arg Asp
         1325                1330                1335

Lys Pro  Ile Arg Glu Gln Ala  Glu Asn Ile Ile His  Leu Phe Thr
         1340                1345                1350

Leu Thr  Asn Leu Gly Ala Pro  Ala Ala Phe Lys Tyr  Phe Asp Thr
         1355                1360                1365
```

-continued

```
Thr Ile Asp Arg Lys Arg Tyr Thr Ser Thr Lys Glu Val Leu Asp
    1370                1375                1380

Ala Thr Leu Ile His Gln Ser Ile Thr Gly Leu Tyr Glu Thr Arg
1385                1390                1395

Ile Asp Leu Ser Gln Leu Gly Gly Asp Lys Arg Pro Ala Ala Thr
1400                1405                1410

Lys Lys Ala Gly Gln Ala Lys Lys Lys Gly Ser Gly Gly Ser
1415                1420                1425

Gly Pro Ser Pro Ala Arg Pro Ala Leu Arg Ala Pro Ala Ser Ala
1430                1435                1440

Thr Ser Gly Ser Arg Lys Arg Ala Arg Pro Pro Ala Ala Pro Gly
    1445                1450                1455

Arg Asp Gln Ala Arg Pro Pro Ala Arg Arg Arg Leu Arg Leu Ser
1460                1465                1470

Val Asp Glu Val Ser Ser Pro Ser Thr Pro Glu Ala Pro Asp Ile
1475                1480                1485

Pro Ala Cys Pro Ser Pro Gly Gln Lys Ile Lys Lys Ser Thr Pro
1490                1495                1500

Ala Ala Gly Gln Pro Pro His Leu Thr Ser Ala Gln Asp Gln Asp
    1505                1510                1515

Thr Ile
    1520

<210> SEQ ID NO 72
<211> LENGTH: 1380
<212> TYPE: PRT
<213> ORGANISM: Artificial sequence
<220> FEATURE:
<223> OTHER INFORMATION: Synthetic polypeptide

<400> SEQUENCE: 72

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Ala Asp Lys Lys Tyr Ser Ile Gly Leu
        35                  40                  45

Asp Ile Gly Thr Asn Ser Val Gly Trp Ala Val Ile Thr Asp Glu Tyr
    50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
            100                 105                 110

Arg Arg Lys Asn Arg Ile Cys Tyr Leu Gln Glu Ile Phe Ser Asn Glu
        115                 120                 125

Met Ala Lys Val Asp Asp Ser Phe Phe His Arg Leu Glu Glu Ser Phe
    130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190
```

```
Ile Tyr Leu Ala Leu Ala His Met Ile Lys Phe Arg Gly His Phe Leu
        195                 200                 205
Ile Glu Gly Asp Leu Asn Pro Asp Asn Ser Asp Val Asp Lys Leu Phe
    210                 215                 220
Ile Gln Leu Val Gln Thr Tyr Asn Gln Leu Phe Glu Glu Asn Pro Ile
225                 230                 235                 240
Asn Ala Ser Gly Val Asp Ala Lys Ala Ile Leu Ser Ala Arg Leu Ser
                245                 250                 255
Lys Ser Arg Arg Leu Glu Asn Leu Ile Ala Gln Leu Pro Gly Glu Lys
            260                 265                 270
Lys Asn Gly Leu Phe Gly Asn Leu Ile Ala Leu Ser Leu Gly Leu Thr
        275                 280                 285
Pro Asn Phe Lys Ser Asn Phe Asp Leu Ala Glu Asp Ala Lys Leu Gln
    290                 295                 300
Leu Ser Lys Asp Thr Tyr Asp Asp Asp Leu Asp Asn Leu Leu Ala Gln
305                 310                 315                 320
Ile Gly Asp Gln Tyr Ala Asp Leu Phe Leu Ala Ala Lys Asn Leu Ser
                325                 330                 335
Asp Ala Ile Leu Leu Ser Asp Ile Leu Arg Val Asn Thr Glu Ile Thr
            340                 345                 350
Lys Ala Pro Leu Ser Ala Ser Met Ile Lys Arg Tyr Asp Glu His His
        355                 360                 365
Gln Asp Leu Thr Leu Leu Lys Ala Leu Val Arg Gln Gln Leu Pro Glu
    370                 375                 380
Lys Tyr Lys Glu Ile Phe Phe Asp Gln Ser Lys Asn Gly Tyr Ala Gly
385                 390                 395                 400
Tyr Ile Asp Gly Gly Ala Ser Gln Glu Glu Phe Tyr Lys Phe Ile Lys
                405                 410                 415
Pro Ile Leu Glu Lys Met Asp Gly Thr Glu Glu Leu Leu Val Lys Leu
            420                 425                 430
Asn Arg Glu Asp Leu Leu Arg Lys Gln Arg Thr Phe Asp Asn Gly Ser
        435                 440                 445
Ile Pro His Gln Ile His Leu Gly Glu Leu His Ala Ile Leu Arg Arg
    450                 455                 460
Gln Glu Asp Phe Tyr Pro Phe Leu Lys Asp Asn Arg Glu Lys Ile Glu
465                 470                 475                 480
Lys Ile Leu Thr Phe Arg Ile Pro Tyr Tyr Val Gly Pro Leu Ala Arg
                485                 490                 495
Gly Asn Ser Arg Phe Ala Trp Met Thr Arg Lys Ser Glu Glu Thr Ile
            500                 505                 510
Thr Pro Trp Asn Phe Glu Glu Val Val Asp Lys Gly Ala Ser Ala Gln
        515                 520                 525
Ser Phe Ile Glu Arg Met Thr Asn Phe Asp Lys Asn Leu Pro Asn Glu
    530                 535                 540
Lys Val Leu Pro Lys His Ser Leu Leu Tyr Glu Tyr Phe Thr Val Tyr
545                 550                 555                 560
Asn Glu Leu Thr Lys Val Lys Tyr Val Thr Glu Gly Met Arg Lys Pro
                565                 570                 575
Ala Phe Leu Ser Gly Glu Gln Lys Lys Ala Ile Val Asp Leu Leu Phe
            580                 585                 590
Lys Thr Asn Arg Lys Val Thr Val Lys Gln Leu Lys Glu Asp Tyr Phe
        595                 600                 605
Lys Lys Ile Glu Cys Phe Asp Ser Val Glu Ile Ser Gly Val Glu Asp
```

610                 615                 620
Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                    645                 650                 655

Asp Ile Val Leu Thr Leu Thr Leu Phe Glu Asp Arg Glu Met Ile Glu
                    660                 665                 670

Glu Arg Leu Lys Thr Tyr Ala His Leu Phe Asp Asp Lys Val Met Lys
                    675                 680                 685

Gln Leu Lys Arg Arg Arg Tyr Thr Gly Trp Gly Arg Leu Ser Arg Lys
                    690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                    725                 730                 735

His Asp Asp Ser Leu Thr Phe Lys Glu Asp Ile Gln Lys Ala Gln Val
                    740                 745                 750

Ser Gly Gln Gly Asp Ser Leu His Glu His Ile Ala Asn Leu Ala Gly
                    755                 760                 765

Ser Pro Ala Ile Lys Lys Gly Ile Leu Gln Thr Val Lys Val Val Asp
                    770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                    805                 810                 815

Arg Glu Arg Met Lys Arg Ile Glu Glu Gly Ile Lys Glu Leu Gly Ser
                    820                 825                 830

Gln Ile Leu Lys Glu His Pro Val Glu Asn Thr Gln Leu Gln Asn Glu
                    835                 840                 845

Lys Leu Tyr Leu Tyr Tyr Leu Gln Asn Gly Arg Asp Met Tyr Val Asp
850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
                    885                 890                 895

Thr Arg Ser Asp Lys Asn Arg Gly Lys Ser Asp Asn Val Pro Ser Glu
                    900                 905                 910

Glu Val Val Lys Lys Met Lys Asn Tyr Trp Arg Gln Leu Leu Asn Ala
                    915                 920                 925

Lys Leu Ile Thr Gln Arg Lys Phe Asp Asn Leu Thr Lys Ala Glu Arg
930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
                    965                 970                 975

Arg Met Asn Thr Lys Tyr Asp Glu Asn Asp Lys Leu Ile Arg Glu Val
                    980                 985                 990

Lys Val Ile Thr Leu Lys Ser Lys Leu Val Ser Asp Phe Arg Lys Asp
                    995                 1000                1005

Phe Gln Phe Tyr Lys Val Arg Glu Ile Asn Asn Tyr His His Ala
    1010                1015                1020

His Asp Ala Tyr Leu Asn Ala Val Val Gly Thr Ala Leu Ile Lys
    1025                1030                1035

Lys Tyr Pro Lys Leu Glu Ser Glu Phe Val Tyr Gly Asp Tyr Lys
    1040                1045                1050

Val Tyr Asp Val Arg Lys Met Ile Ala Lys Ser Glu Gln Glu Ile
    1055                1060                1065

Gly Lys Ala Thr Ala Lys Tyr Phe Phe Tyr Ser Asn Ile Met Asn
    1070                1075                1080

Phe Phe Lys Thr Glu Ile Thr Leu Ala Asn Gly Glu Ile Arg Lys
    1085                1090                1095

Arg Pro Leu Ile Glu Thr Asn Gly Glu Thr Gly Glu Ile Val Trp
    1100                1105                1110

Asp Lys Gly Arg Asp Phe Ala Thr Val Arg Lys Val Leu Ser Met
    1115                1120                1125

Pro Gln Val Asn Ile Val Lys Lys Thr Glu Val Gln Thr Gly Gly
    1130                1135                1140

Phe Ser Lys Glu Ser Ile Leu Pro Lys Arg Asn Ser Asp Lys Leu
    1145                1150                1155

Ile Ala Arg Lys Lys Asp Trp Asp Pro Lys Lys Tyr Gly Gly Phe
    1160                1165                1170

Asp Ser Pro Thr Val Ala Tyr Ser Val Leu Val Val Ala Lys Val
    1175                1180                1185

Glu Lys Gly Lys Ser Lys Lys Leu Lys Ser Val Lys Glu Leu Leu
    1190                1195                1200

Gly Ile Thr Ile Met Glu Arg Ser Ser Phe Glu Lys Asn Pro Ile
    1205                1210                1215

Asp Phe Leu Glu Ala Lys Gly Tyr Lys Glu Val Lys Lys Asp Leu
    1220                1225                1230

Ile Ile Lys Leu Pro Lys Tyr Ser Leu Phe Glu Leu Glu Asn Gly
    1235                1240                1245

Arg Lys Arg Met Leu Ala Ser Ala Gly Glu Leu Gln Lys Gly Asn
    1250                1255                1260

Glu Leu Ala Leu Pro Ser Lys Tyr Val Asn Phe Leu Tyr Leu Ala
    1265                1270                1275

Ser His Tyr Glu Lys Leu Lys Gly Ser Pro Glu Asp Asn Glu Gln
    1280                1285                1290

Lys Gln Leu Phe Val Glu Gln His Lys His Tyr Leu Asp Glu Ile
    1295                1300                1305

Ile Glu Gln Ile Ser Glu Phe Ser Lys Arg Val Ile Leu Ala Asp
    1310                1315                1320

Ala Asn Leu Asp Lys Val Leu Ser Ala Tyr Asn Lys His Arg Asp
    1325                1330                1335

Lys Pro Ile Arg Glu Gln Ala Glu Asn Ile Ile His Leu Phe Thr
    1340                1345                1350

Leu Thr Asn Leu Gly Ala Pro Ala Ala Phe Lys Tyr Phe Asp Thr
    1355                1360                1365

Thr Ile Asp Arg Lys Arg Tyr Thr Ser Thr Lys Glu
    1370                1375                1380

<210> SEQ ID NO 73
<211> LENGTH: 1469
<212> TYPE: PRT
<213> ORGANISM: Artificial sequence
<220> FEATURE:
<223> OTHER INFORMATION: Synthetic polypeptide

<400> SEQUENCE: 73

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20              25              30

Gly Ile His Gly Val Pro Ala Ala Asp Lys Lys Tyr Ser Ile Gly Leu
        35              40              45

Asp Ile Gly Thr Asn Ser Val Gly Trp Ala Val Ile Thr Asp Glu Tyr
        50              55              60

Lys Val Pro Ser Lys Lys Phe Lys Val Leu Gly Asn Thr Asp Arg His
65              70              75              80

Ser Ile Lys Lys Asn Leu Ile Gly Ala Leu Leu Phe Asp Ser Gly Glu
            85              90              95

Thr Ala Glu Ala Thr Arg Leu Lys Arg Thr Ala Arg Arg Arg Tyr Thr
            100             105             110

Arg Arg Lys Asn Arg Ile Cys Tyr Leu Gln Glu Ile Phe Ser Asn Glu
            115             120             125

Met Ala Lys Val Asp Asp Ser Phe Phe His Arg Leu Glu Glu Ser Phe
130             135             140

Leu Val Glu Glu Asp Lys Lys His Glu Arg His Pro Ile Phe Gly Asn
145             150             155             160

Ile Val Asp Glu Val Ala Tyr His Glu Lys Tyr Pro Thr Ile Tyr His
            165             170             175

Leu Arg Lys Lys Leu Val Asp Ser Thr Asp Lys Ala Asp Leu Arg Leu
            180             185             190

Ile Tyr Leu Ala Leu Ala His Met Ile Lys Phe Arg Gly His Phe Leu
            195             200             205

Ile Glu Gly Asp Leu Asn Pro Asp Asn Ser Asp Val Asp Lys Leu Phe
            210             215             220

Ile Gln Leu Val Gln Thr Tyr Asn Gln Leu Phe Glu Glu Asn Pro Ile
225             230             235             240

Asn Ala Ser Gly Val Asp Ala Lys Ala Ile Leu Ser Ala Arg Leu Ser
            245             250             255

Lys Ser Arg Arg Leu Glu Asn Leu Ile Ala Gln Leu Pro Gly Glu Lys
            260             265             270

Lys Asn Gly Leu Phe Gly Asn Leu Ile Ala Leu Ser Leu Gly Leu Thr
            275             280             285

Pro Asn Phe Lys Ser Asn Phe Asp Leu Ala Glu Asp Ala Lys Leu Gln
            290             295             300

Leu Ser Lys Asp Thr Tyr Asp Asp Asp Leu Asp Asn Leu Leu Ala Gln
305             310             315             320

Ile Gly Asp Gln Tyr Ala Asp Leu Phe Leu Ala Ala Lys Asn Leu Ser
            325             330             335

Asp Ala Ile Leu Leu Ser Asp Ile Leu Arg Val Asn Thr Glu Ile Thr
            340             345             350

Lys Ala Pro Leu Ser Ala Ser Met Ile Lys Arg Tyr Asp Glu His His
            355             360             365

Gln Asp Leu Thr Leu Leu Lys Ala Leu Val Arg Gln Gln Leu Pro Glu
            370             375             380

Lys Tyr Lys Glu Ile Phe Phe Asp Gln Ser Lys Asn Gly Tyr Ala Gly
385             390             395             400

Tyr Ile Asp Gly Gly Ala Ser Gln Glu Glu Phe Tyr Lys Phe Ile Lys
            405             410             415
```

```
Pro Ile Leu Glu Lys Met Asp Gly Thr Glu Leu Leu Val Lys Leu
            420                 425                 430

Asn Arg Glu Asp Leu Leu Arg Lys Gln Arg Thr Phe Asp Asn Gly Ser
        435                 440                 445

Ile Pro His Gln Ile His Leu Gly Glu Leu His Ala Ile Leu Arg Arg
    450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
            500                 505                 510

Thr Pro Trp Asn Phe Glu Glu Val Val Asp Lys Gly Ala Ser Ala Gln
        515                 520                 525

Ser Phe Ile Glu Arg Met Thr Asn Phe Asp Lys Asn Leu Pro Asn Glu
    530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
            580                 585                 590

Lys Thr Asn Arg Lys Val Thr Val Lys Gln Leu Lys Glu Asp Tyr Phe
        595                 600                 605

Lys Lys Ile Glu Cys Phe Asp Ser Val Glu Ile Ser Gly Val Glu Asp
    610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
            660                 665                 670

Glu Arg Leu Lys Thr Tyr Ala His Leu Phe Asp Asp Lys Val Met Lys
        675                 680                 685

Gln Leu Lys Arg Arg Arg Tyr Thr Gly Trp Gly Arg Leu Ser Arg Lys
    690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
        755                 760                 765

Ser Pro Ala Ile Lys Lys Gly Ile Leu Gln Thr Val Lys Val Val Asp
    770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                805                 810                 815

Arg Glu Arg Met Lys Arg Ile Glu Glu Gly Ile Lys Glu Leu Gly Ser
            820                 825                 830

Gln Ile Leu Lys Glu His Pro Val Glu Asn Thr Gln Leu Gln Asn Glu
```

-continued

```
            835                 840                 845
Lys Leu Tyr Leu Tyr Tyr Leu Gln Asn Gly Arg Asp Met Tyr Val Asp
            850                 855                 860
Gln Glu Leu Asp Ile Asn Arg Leu Ser Asp Tyr Asp Val Asp His Ile
865                 870                 875                 880
Val Pro Gln Ser Phe Leu Lys Asp Asp Ser Ile Asp Asn Lys Val Leu
                    885                 890                 895
Thr Arg Ser Asp Lys Asn Arg Gly Lys Ser Asp Asn Val Pro Ser Glu
                900                 905                 910
Glu Val Val Lys Lys Met Lys Asn Tyr Trp Arg Gln Leu Leu Asn Ala
                915                 920                 925
Lys Leu Ile Thr Gln Arg Lys Phe Asp Asn Leu Thr Lys Ala Glu Arg
            930                 935                 940
Gly Gly Leu Ser Glu Leu Asp Lys Ala Gly Phe Ile Lys Arg Gln Leu
945                 950                 955                 960
Val Glu Thr Arg Gln Ile Thr Lys His Val Ala Gln Ile Leu Asp Ser
                    965                 970                 975
Arg Met Asn Thr Lys Tyr Asp Glu Asn Asp Lys Leu Ile Arg Glu Val
                980                 985                 990
Lys Val Ile Thr Leu Lys Ser Lys  Leu Val Ser Asp Phe Arg Lys Asp
                995                1000                1005
Phe Gln Phe Tyr Lys Val Arg  Glu Ile Asn Asn Tyr  His His Ala
       1010                1015                1020
His Asp Ala Tyr Leu Asn Ala  Val Val Gly Thr Ala  Leu Ile Lys
       1025                1030                1035
Lys Tyr Pro Lys Leu Glu Ser  Glu Phe Val Tyr Gly  Asp Tyr Lys
       1040                1045                1050
Val Tyr Asp Val Arg Lys Met  Ile Ala Lys Ser Glu  Gln Glu Ile
       1055                1060                1065
Gly Lys Ala Thr Ala Lys Tyr  Phe Phe Tyr Ser Asn  Ile Met Asn
       1070                1075                1080
Phe Phe Lys Thr Glu Ile Thr  Leu Ala Asn Gly Glu  Ile Arg Lys
       1085                1090                1095
Arg Pro Leu Ile Glu Thr Asn  Gly Glu Thr Gly Glu  Ile Val Trp
       1100                1105                1110
Asp Lys Gly Arg Asp Phe Ala  Thr Val Arg Lys Val  Leu Ser Met
       1115                1120                1125
Pro Gln Val Asn Ile Val Lys  Lys Thr Glu Val Gln  Thr Gly Gly
       1130                1135                1140
Phe Ser Lys Glu Ser Ile Leu  Pro Lys Arg Asn Ser  Asp Lys Leu
       1145                1150                1155
Ile Ala Arg Lys Lys Asp Trp  Asp Pro Lys Lys Tyr  Gly Gly Phe
       1160                1165                1170
Asp Ser Pro Thr Val Ala Tyr  Ser Val Leu Val Val  Ala Lys Val
       1175                1180                1185
Glu Lys Gly Lys Ser Lys Lys  Leu Lys Ser Val Lys  Glu Leu Leu
       1190                1195                1200
Gly Ile Thr Ile Met Glu Arg  Ser Ser Phe Glu Lys  Asn Pro Ile
       1205                1210                1215
Asp Phe Leu Glu Ala Lys Gly  Tyr Lys Glu Val Lys  Lys Asp Leu
       1220                1225                1230
Ile Ile Lys Leu Pro Lys Tyr  Ser Leu Phe Glu Leu  Glu Asn Gly
       1235                1240                1245
```

Arg Lys Arg Met Leu Ala Ser Ala Gly Glu Leu Gln Lys Gly Asn
    1250                1255                1260

Glu Leu Ala Leu Pro Ser Lys Tyr Val Asn Phe Leu Tyr Leu Ala
    1265                1270                1275

Ser His Tyr Glu Lys Leu Lys Gly Ser Pro Glu Asp Asn Glu Gln
    1280                1285                1290

Lys Gln Leu Phe Val Glu Gln His Lys His Tyr Leu Asp Glu Ile
    1295                1300                1305

Ile Glu Gln Ile Ser Glu Phe Ser Lys Arg Val Ile Leu Ala Asp
    1310                1315                1320

Ala Asn Leu Asp Lys Val Leu Ser Ala Tyr Asn Lys His Arg Asp
    1325                1330                1335

Lys Pro Ile Arg Glu Gln Ala Glu Asn Ile Ile His Leu Phe Thr
    1340                1345                1350

Leu Thr Asn Leu Gly Ala Pro Ala Ala Phe Lys Tyr Phe Asp Thr
    1355                1360                1365

Thr Ile Asp Arg Lys Arg Tyr Thr Ser Thr Lys Glu Val Leu Asp
    1370                1375                1380

Ala Thr Leu Ile His Gln Ser Ile Thr Gly Leu Tyr Glu Thr Arg
    1385                1390                1395

Ile Asp Leu Ser Gln Leu Gly Gly Asp Lys Arg Pro Ala Ala Thr
    1400                1405                1410

Lys Lys Ala Gly Gln Ala Lys Lys Lys Lys Gly Ser Gly Gly Ser
    1415                1420                1425

Gly Ser His Gly Phe Pro Pro Glu Val Glu Glu Gln Asp Asp Gly
    1430                1435                1440

Thr Leu Pro Met Ser Cys Ala Gln Glu Ser Gly Met Asp Arg His
    1445                1450                1455

Pro Ala Ala Cys Ala Ser Ala Arg Ile Asn Val
    1460                1465

<210> SEQ ID NO 74
<211> LENGTH: 1471
<212> TYPE: PRT
<213> ORGANISM: Artificial sequence
<220> FEATURE:
<223> OTHER INFORMATION: Synthetic polypeptide

<400> SEQUENCE: 74

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Ile His Gly Val Pro Ala Ala Asp Lys Lys Tyr Ser Ile Gly Leu
                35                  40                  45

Asp Ile Gly Thr Asn Ser Val Gly Trp Ala Val Ile Thr Asp Glu Tyr
        50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
                100                 105                 110

Arg Arg Lys Asn Arg Ile Cys Tyr Leu Gln Glu Ile Phe Ser Asn Glu
            115                 120                 125

```
Met Ala Lys Val Asp Asp Ser Phe Phe His Arg Leu Glu Glu Ser Phe
130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
            165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
            195                 200                 205

Ile Glu Gly Asp Leu Asn Pro Asp Asn Ser Asp Val Asp Lys Leu Phe
210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
            245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
            275                 280                 285

Pro Asn Phe Lys Ser Asn Phe Asp Leu Ala Glu Asp Ala Lys Leu Gln
290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
            325                 330                 335

Asp Ala Ile Leu Leu Ser Asp Ile Leu Arg Val Asn Thr Glu Ile Thr
            340                 345                 350

Lys Ala Pro Leu Ser Ala Ser Met Ile Lys Arg Tyr Asp Glu His His
            355                 360                 365

Gln Asp Leu Thr Leu Leu Lys Ala Leu Val Arg Gln Gln Leu Pro Glu
370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
            405                 410                 415

Pro Ile Leu Glu Lys Met Asp Gly Thr Glu Glu Leu Leu Val Lys Leu
            420                 425                 430

Asn Arg Glu Asp Leu Leu Arg Lys Gln Arg Thr Phe Asp Asn Gly Ser
            435                 440                 445

Ile Pro His Gln Ile His Leu Gly Glu Leu His Ala Ile Leu Arg Arg
450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
            485                 490                 495

Gly Asn Ser Arg Phe Ala Trp Met Thr Arg Lys Ser Glu Glu Thr Ile
            500                 505                 510

Thr Pro Trp Asn Phe Glu Glu Val Val Asp Lys Gly Ala Ser Ala Gln
            515                 520                 525

Ser Phe Ile Glu Arg Met Thr Asn Phe Asp Lys Asn Leu Pro Asn Glu
530                 535                 540
```

-continued

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
            565                 570                 575

Ala Phe Leu Ser Gly Glu Gln Lys Lys Ala Ile Val Asp Leu Leu Phe
            580                 585                 590

Lys Thr Asn Arg Lys Val Thr Val Lys Gln Leu Lys Glu Asp Tyr Phe
            595                 600                 605

Lys Lys Ile Glu Cys Phe Asp Ser Val Glu Ile Ser Gly Val Glu Asp
            610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
            645                 650                 655

Asp Ile Val Leu Thr Leu Thr Leu Phe Glu Asp Arg Glu Met Ile Glu
            660                 665                 670

Glu Arg Leu Lys Thr Tyr Ala His Leu Phe Asp Asp Lys Val Met Lys
            675                 680                 685

Gln Leu Lys Arg Arg Arg Tyr Thr Gly Trp Gly Arg Leu Ser Arg Lys
            690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
            725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
            755                 760                 765

Ser Pro Ala Ile Lys Lys Gly Ile Leu Gln Thr Val Lys Val Val Asp
            770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
            805                 810                 815

Arg Glu Arg Met Lys Arg Ile Glu Glu Gly Ile Lys Glu Leu Gly Ser
            820                 825                 830

Gln Ile Leu Lys Glu His Pro Val Glu Asn Thr Gln Leu Gln Asn Glu
            835                 840                 845

Lys Leu Tyr Leu Tyr Tyr Leu Gln Asn Gly Arg Asp Met Tyr Val Asp
850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
            885                 890                 895

Thr Arg Ser Asp Lys Asn Arg Gly Lys Ser Asp Asn Val Pro Ser Glu
            900                 905                 910

Glu Val Val Lys Lys Met Lys Asn Tyr Trp Arg Gln Leu Leu Asn Ala
            915                 920                 925

Lys Leu Ile Thr Gln Arg Lys Phe Asp Asn Leu Thr Lys Ala Glu Arg
            930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser

-continued

```
              965                 970                 975
Arg Met Asn Thr Lys Tyr Asp Glu Asn Asp Lys Leu Ile Arg Glu Val
              980                 985                 990
Lys Val Ile Thr Leu Lys Ser Lys Leu Val Ser Asp Phe Arg Lys Asp
          995                1000                1005
Phe Gln Phe Tyr Lys Val Arg Glu Ile Asn Asn Tyr His His Ala
    1010                1015                1020
His Asp Ala Tyr Leu Asn Ala Val Val Gly Thr Ala Leu Ile Lys
    1025                1030                1035
Lys Tyr Pro Lys Leu Glu Ser Glu Phe Val Tyr Gly Asp Tyr Lys
    1040                1045                1050
Val Tyr Asp Val Arg Lys Met Ile Ala Lys Ser Glu Gln Glu Ile
    1055                1060                1065
Gly Lys Ala Thr Ala Lys Tyr Phe Phe Tyr Ser Asn Ile Met Asn
    1070                1075                1080
Phe Phe Lys Thr Glu Ile Thr Leu Ala Asn Gly Glu Ile Arg Lys
    1085                1090                1095
Arg Pro Leu Ile Glu Thr Asn Gly Glu Thr Gly Glu Ile Val Trp
    1100                1105                1110
Asp Lys Gly Arg Asp Phe Ala Thr Val Arg Lys Val Leu Ser Met
    1115                1120                1125
Pro Gln Val Asn Ile Val Lys Lys Thr Glu Val Gln Thr Gly Gly
    1130                1135                1140
Phe Ser Lys Glu Ser Ile Leu Pro Lys Arg Asn Ser Asp Lys Leu
    1145                1150                1155
Ile Ala Arg Lys Lys Asp Trp Asp Pro Lys Lys Tyr Gly Gly Phe
    1160                1165                1170
Asp Ser Pro Thr Val Ala Tyr Ser Val Leu Val Val Ala Lys Val
    1175                1180                1185
Glu Lys Gly Lys Ser Lys Lys Leu Lys Ser Val Lys Glu Leu Leu
    1190                1195                1200
Gly Ile Thr Ile Met Glu Arg Ser Ser Phe Glu Lys Asn Pro Ile
    1205                1210                1215
Asp Phe Leu Glu Ala Lys Gly Tyr Lys Glu Val Lys Lys Asp Leu
    1220                1225                1230
Ile Ile Lys Leu Pro Lys Tyr Ser Leu Phe Glu Leu Glu Asn Gly
    1235                1240                1245
Arg Lys Arg Met Leu Ala Ser Ala Gly Glu Leu Gln Lys Gly Asn
    1250                1255                1260
Glu Leu Ala Leu Pro Ser Lys Tyr Val Asn Phe Leu Tyr Leu Ala
    1265                1270                1275
Ser His Tyr Glu Lys Leu Lys Gly Ser Pro Glu Asp Asn Glu Gln
    1280                1285                1290
Lys Gln Leu Phe Val Glu Gln His Lys His Tyr Leu Asp Glu Ile
    1295                1300                1305
Ile Glu Gln Ile Ser Glu Phe Ser Lys Arg Val Ile Leu Ala Asp
    1310                1315                1320
Ala Asn Leu Asp Lys Val Leu Ser Ala Tyr Asn Lys His Arg Asp
    1325                1330                1335
Lys Pro Ile Arg Glu Gln Ala Glu Asn Ile Ile His Leu Phe Thr
    1340                1345                1350
Leu Thr Asn Leu Gly Ala Pro Ala Ala Phe Lys Tyr Phe Asp Thr
    1355                1360                1365
```

Thr Ile Asp Arg Lys Arg Tyr Thr Ser Thr Lys Glu Val Leu Asp
    1370                1375                1380

Ala Thr Leu Ile His Gln Ser Ile Thr Gly Leu Tyr Glu Thr Arg
    1385                1390                1395

Ile Asp Leu Ser Gln Leu Gly Gly Asp Lys Arg Pro Ala Ala Thr
    1400                1405                1410

Lys Lys Ala Gly Gln Ala Lys Lys Lys Gly Ser Gly Gly Ser
    1415                1420                1425

Gly Lys Leu Ser His Gly Phe Pro Pro Glu Val Glu Glu Gln Asp
    1430                1435                1440

Asp Gly Thr Leu Pro Met Ser Cys Ala Gln Glu Ser Gly Met Asp
    1445                1450                1455

Arg His Pro Ala Ala Cys Ala Ser Ala Arg Ile Asn Val
    1460                1465                1470

<210> SEQ ID NO 75
<211> LENGTH: 1624
<212> TYPE: PRT
<213> ORGANISM: Artificial sequence
<220> FEATURE:
<223> OTHER INFORMATION: Synthetic polypeptide

<400> SEQUENCE: 75

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Ile His Gly Val Pro Ala Ala Asp Lys Lys Tyr Ser Ile Gly Leu
            35                  40                  45

Asp Ile Gly Thr Asn Ser Val Gly Trp Ala Val Ile Thr Asp Glu Tyr
        50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
            100                 105                 110

Arg Arg Lys Asn Arg Ile Cys Tyr Leu Gln Glu Ile Phe Ser Asn Glu
        115                 120                 125

Met Ala Lys Val Asp Asp Ser Phe Phe His Arg Leu Glu Glu Ser Phe
    130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
        195                 200                 205

Ile Glu Gly Asp Leu Asn Pro Asp Asn Ser Asp Val Asp Lys Leu Phe
    210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

```
Lys Ser Arg Arg Leu Glu Asn Leu Ile Ala Gln Leu Pro Gly Glu Lys
                260                 265                 270

Lys Asn Gly Leu Phe Gly Asn Leu Ile Ala Leu Ser Leu Gly Leu Thr
            275                 280                 285

Pro Asn Phe Lys Ser Asn Phe Asp Leu Ala Glu Asp Ala Lys Leu Gln
        290                 295                 300

Leu Ser Lys Asp Thr Tyr Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
            340                 345                 350

Lys Ala Pro Leu Ser Ala Ser Met Ile Lys Arg Tyr Asp Glu His His
        355                 360                 365

Gln Asp Leu Thr Leu Leu Lys Ala Leu Val Arg Gln Gln Leu Pro Glu
    370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
            420                 425                 430

Asn Arg Glu Asp Leu Leu Arg Lys Gln Arg Thr Phe Asp Asn Gly Ser
        435                 440                 445

Ile Pro His Gln Ile His Leu Gly Glu Leu His Ala Ile Leu Arg Arg
    450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
            500                 505                 510

Thr Pro Trp Asn Phe Glu Glu Val Val Asp Lys Gly Ala Ser Ala Gln
        515                 520                 525

Ser Phe Ile Glu Arg Met Thr Asn Phe Asp Lys Asn Leu Pro Asn Glu
    530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
            580                 585                 590

Lys Thr Asn Arg Lys Val Thr Val Lys Gln Leu Lys Glu Asp Tyr Phe
        595                 600                 605

Lys Lys Ile Glu Cys Phe Asp Ser Val Glu Ile Ser Gly Val Glu Asp
    610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
            660                 665                 670
```

Glu Arg Leu Lys Thr Tyr Ala His Leu Phe Asp Asp Lys Val Met Lys
    675                 680                 685

Gln Leu Lys Arg Arg Tyr Thr Gly Trp Gly Arg Leu Ser Arg Lys
690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
        755                 760                 765

Ser Pro Ala Ile Lys Lys Gly Ile Leu Gln Thr Val Lys Val Val Asp
    770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                805                 810                 815

Arg Glu Arg Met Lys Arg Ile Glu Glu Gly Ile Lys Glu Leu Gly Ser
            820                 825                 830

Gln Ile Leu Lys Glu His Pro Val Glu Asn Thr Gln Leu Gln Asn Glu
        835                 840                 845

Lys Leu Tyr Leu Tyr Tyr Leu Gln Asn Gly Arg Asp Met Tyr Val Asp
    850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
                885                 890                 895

Thr Arg Ser Asp Lys Asn Arg Gly Lys Ser Asp Asn Val Pro Ser Glu
            900                 905                 910

Glu Val Val Lys Lys Met Lys Asn Tyr Trp Arg Gln Leu Leu Asn Ala
        915                 920                 925

Lys Leu Ile Thr Gln Arg Lys Phe Asp Asn Leu Thr Lys Ala Glu Arg
    930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
                965                 970                 975

Arg Met Asn Thr Lys Tyr Asp Glu Asn Asp Lys Leu Ile Arg Glu Val
            980                 985                 990

Lys Val Ile Thr Leu Lys Ser Lys Leu Val Ser Asp Phe Arg Lys Asp
        995                 1000                1005

Phe Gln Phe Tyr Lys Val Arg Glu Ile Asn Asn Tyr His His Ala
    1010                1015                1020

His Asp Ala Tyr Leu Asn Ala Val Val Gly Thr Ala Leu Ile Lys
    1025                1030                1035

Lys Tyr Pro Lys Leu Glu Ser Glu Phe Val Tyr Gly Asp Tyr Lys
    1040                1045                1050

Val Tyr Asp Val Arg Lys Met Ile Ala Lys Ser Glu Gln Glu Ile
    1055                1060                1065

Gly Lys Ala Thr Ala Lys Tyr Phe Phe Tyr Ser Asn Ile Met Asn
    1070                1075                1080

Phe Phe Lys Thr Glu Ile Thr Leu Ala Asn Gly Glu Ile Arg Lys

-continued

```
            1085                1090                1095
Arg Pro Leu Ile Glu Thr Asn Gly Glu Thr Gly Glu Ile Val Trp
            1100                1105                1110
Asp Lys Gly Arg Asp Phe Ala Thr Val Arg Lys Val Leu Ser Met
            1115                1120                1125
Pro Gln Val Asn Ile Val Lys Lys Thr Glu Val Gln Thr Gly Gly
            1130                1135                1140
Phe Ser Lys Glu Ser Ile Leu Pro Lys Arg Asn Ser Asp Lys Leu
            1145                1150                1155
Ile Ala Arg Lys Lys Asp Trp Asp Pro Lys Lys Tyr Gly Gly Phe
            1160                1165                1170
Asp Ser Pro Thr Val Ala Tyr Ser Val Leu Val Val Ala Lys Val
            1175                1180                1185
Glu Lys Gly Lys Ser Lys Lys Leu Lys Ser Val Lys Glu Leu Leu
            1190                1195                1200
Gly Ile Thr Ile Met Glu Arg Ser Ser Phe Glu Lys Asn Pro Ile
            1205                1210                1215
Asp Phe Leu Glu Ala Lys Gly Tyr Lys Glu Val Lys Lys Asp Leu
            1220                1225                1230
Ile Ile Lys Leu Pro Lys Tyr Ser Leu Phe Glu Leu Glu Asn Gly
            1235                1240                1245
Arg Lys Arg Met Leu Ala Ser Ala Gly Glu Leu Gln Lys Gly Asn
            1250                1255                1260
Glu Leu Ala Leu Pro Ser Lys Tyr Val Asn Phe Leu Tyr Leu Ala
            1265                1270                1275
Ser His Tyr Glu Lys Leu Lys Gly Ser Pro Glu Asp Asn Glu Gln
            1280                1285                1290
Lys Gln Leu Phe Val Glu Gln His Lys His Tyr Leu Asp Glu Ile
            1295                1300                1305
Ile Glu Gln Ile Ser Glu Phe Ser Lys Arg Val Ile Leu Ala Asp
            1310                1315                1320
Ala Asn Leu Asp Lys Val Leu Ser Ala Tyr Asn Lys His Arg Asp
            1325                1330                1335
Lys Pro Ile Arg Glu Gln Ala Glu Asn Ile Ile His Leu Phe Thr
            1340                1345                1350
Leu Thr Asn Leu Gly Ala Pro Ala Ala Phe Lys Tyr Phe Asp Thr
            1355                1360                1365
Thr Ile Asp Arg Lys Arg Tyr Thr Ser Thr Lys Glu Val Leu Asp
            1370                1375                1380
Ala Thr Leu Ile His Gln Ser Ile Thr Gly Leu Tyr Glu Thr Arg
            1385                1390                1395
Ile Asp Leu Ser Gln Leu Gly Gly Asp Lys Arg Pro Ala Ala Thr
            1400                1405                1410
Lys Lys Ala Gly Gln Ala Lys Lys Lys Lys Leu Ser His Gly
            1415                1420                1425
Phe Pro Pro Glu Val Glu Glu Gln Asp Asp Gly Thr Leu Pro Met
            1430                1435                1440
Ser Cys Ala Gln Glu Ser Gly Met Asp Arg His Pro Ala Ala Cys
            1445                1450                1455
Ala Ser Ala Arg Ile Asn Val Val Leu Asp Ala Thr Leu Ile His
            1460                1465                1470
Gln Ser Ile Thr Gly Leu Tyr Glu Thr Arg Ile Asp Leu Ser Gln
            1475                1480                1485
```

```
Leu Gly Gly Asp Lys Arg Pro Ala Ala Thr Lys Lys Ala Gly Gln
    1490                1495                1500

Ala Lys Lys Lys Gly Ser Gly Gly Ser Gly Met Asn Pro Ser
    1505                1510                1515

Met Lys Gln Lys Gln Glu Glu Ile Lys Glu Asn Ile Lys Asn Ser
    1520                1525                1530

Ser Val Pro Arg Arg Thr Leu Lys Met Ile Gln Pro Ser Ala Ser
    1535                1540                1545

Gly Ser Leu Val Gly Arg Glu Asn Glu Leu Ser Ala Gly Leu Ser
    1550                1555                1560

Lys Arg Lys His Arg Asn Asp His Leu Thr Ser Thr Thr Ser Ser
    1565                1570                1575

Pro Gly Val Ile Val Pro Glu Ser Ser Glu Asn Lys Asn Leu Gly
    1580                1585                1590

Gly Val Thr Gln Glu Ser Phe Asp Leu Met Ile Lys Glu Asn Pro
    1595                1600                1605

Ser Ser Gln Tyr Trp Lys Glu Val Ala Glu Lys Arg Lys Ala
    1610                1615                1620

Leu
```

<210> SEQ ID NO 76
<211> LENGTH: 91
<212> TYPE: PRT
<213> ORGANISM: Artificial sequence
<220> FEATURE:
<223> OTHER INFORMATION: Synthetic polypeptide

<400> SEQUENCE: 76

```
Pro Ser Pro Ala Arg Pro Ala Leu Arg Ala Pro Ala Ser Ala Thr Ser
1               5                   10                  15

Gly Ser Arg Lys Arg Ala Arg Pro Pro Ala Ala Pro Gly Arg Asp Gln
                20                  25                  30

Ala Arg Pro Pro Ala Arg Arg Leu Arg Leu Ser Val Asp Glu Val
                35                  40                  45

Ser Ser Pro Ser Thr Pro Glu Ala Pro Asp Ile Pro Ala Cys Pro Ser
    50                  55                  60

Pro Gly Gln Lys Ile Lys Lys Ser Thr Pro Ala Ala Gly Gln Pro Pro
65                  70                  75                  80

His Leu Thr Ser Ala Gln Asp Gln Asp Thr Ile
                85                  90
```

<210> SEQ ID NO 77
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 77

```
Met Asn Pro Ser Met Lys Gln Lys Gln Glu Glu Ile Lys Glu Asn Ile
1               5                   10                  15

Lys Asn Ser Ser Val Pro Arg Arg Thr Leu Lys Met Ile Gln Pro Ser
                20                  25                  30

Ala Ser Gly Ser Leu Val Gly Arg Glu Asn Glu Leu Ser Ala Gly Leu
                35                  40                  45

Ser Lys Arg Lys His Arg Asn Asp His Leu Thr Ser Thr Thr Ser Ser
    50                  55                  60
```

```
Pro Gly Val Ile Val Pro Glu Ser Ser Glu Asn Lys Asn Leu Gly Gly
 65                  70                  75                  80

Val Thr Gln Glu Ser Phe Asp Leu Met Ile Lys Glu Asn Pro Ser Ser
                 85                  90                  95

Gln Tyr Trp Lys Glu Val Ala Glu Lys Arg Arg Lys Ala Leu
            100                 105                 110

<210> SEQ ID NO 78
<211> LENGTH: 40
<212> TYPE: PRT
<213> ORGANISM: Artificial sequence
<220> FEATURE:
<223> OTHER INFORMATION: Synthetic peptide

<400> SEQUENCE: 78

Ser His Gly Phe Pro Pro Glu Val Glu Glu Gln Asp Asp Gly Thr Leu
 1               5                  10                  15

Pro Met Ser Cys Ala Gln Glu Ser Gly Met Asp Arg His Pro Ala Ala
             20                  25                  30

Cys Ala Ser Ala Arg Ile Asn Val
             35                  40

<210> SEQ ID NO 79
<211> LENGTH: 42
<212> TYPE: PRT
<213> ORGANISM: Artificial sequence
<220> FEATURE:
<223> OTHER INFORMATION: Synthetic peptide

<400> SEQUENCE: 79

Lys Leu Ser His Gly Phe Pro Pro Glu Val Glu Glu Gln Asp Asp Gly
 1               5                  10                  15

Thr Leu Pro Met Ser Cys Ala Gln Glu Ser Gly Met Asp Arg His Pro
             20                  25                  30

Ala Ala Cys Ala Ser Ala Arg Ile Asn Val
             35                  40

<210> SEQ ID NO 80
<211> LENGTH: 9
<212> TYPE: PRT
<213> ORGANISM: Artificial Sequence
<220> FEATURE:
<223> OTHER INFORMATION: Synthetic peptide

<400> SEQUENCE: 80

Phe Thr Ile His Val Asp Glu Ala Glu
 1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic peptide

<400> SEQUENCE: 81

Gln Arg Arg Val Thr Asp Phe Phe
 1               5

<210> SEQ ID NO 82
<211> LENGTH: 8
<212> TYPE: PRT
<213> ORGANISM: Artificial Sequence
```

```
<220> FEATURE:
<223> OTHER INFORMATION: Synthetic peptide

<400> SEQUENCE: 82

Gln Thr Ser Met Thr Asp Phe Tyr
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: VARIANT
<222> LOCATION: (4)..(4)
<223> OTHER INFORMATION: Xaa denotes Val, Leu, Met or Ile
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: VARIANT
<222> LOCATION: (7)..(8)
<223> OTHER INFORMATION: Xaa denotes Phe or Tyr

<400> SEQUENCE: 83

Gln Xaa Xaa Xaa Xaa Xaa Xaa Xaa
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic peptide

<400> SEQUENCE: 84

Asp Gly Tyr Thr Pro Glu Pro
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic peptide

<400> SEQUENCE: 85

Asn Glu Tyr Thr Glu Gly Pro
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic peptide

<400> SEQUENCE: 86

Asp Glu Pro Gln Thr Val Pro Asp
1               5

<210> SEQ ID NO 87
<211> LENGTH: 8
```

```
<212> TYPE: PRT
<213> ORGANISM: Artificial Sequence
<220> FEATURE:
<223> OTHER INFORMATION: Synthetic peptide

<400> SEQUENCE: 87

Glu Glu Pro Gln Thr Val Pro Glu
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic peptide

<400> SEQUENCE: 88

Asp Glu Gln Phe Val Pro Asp
1               5

<210> SEQ ID NO 89
<211> LENGTH: 6
<212> TYPE: PRT
<213> ORGANISM: Artificial Sequence
<220> FEATURE:
<223> OTHER INFORMATION: Synthetic peptide

<400> SEQUENCE: 89

Asp Glu Glu Thr Gly Glu
1               5

<210> SEQ ID NO 90
<211> LENGTH: 6
<212> TYPE: PRT
<213> ORGANISM: Artificial Sequence
<220> FEATURE:
<223> OTHER INFORMATION: Synthetic peptide

<400> SEQUENCE: 90

Asn Val Glu Ser Gly Glu
1               5

<210> SEQ ID NO 91
<211> LENGTH: 6
<212> TYPE: PRT
<213> ORGANISM: Artificial Sequence
<220> FEATURE:
<223> OTHER INFORMATION: Synthetic peptide

<400> SEQUENCE: 91

Asn Gln Glu Thr Gly Glu
1               5

<210> SEQ ID NO 92
<211> LENGTH: 6
<212> TYPE: PRT
<213> ORGANISM: Artificial Sequence
<220> FEATURE:
<223> OTHER INFORMATION: Synthetic peptide

<400> SEQUENCE: 92

Asp Pro Glu Asn Gly Glu
1               5

<210> SEQ ID NO 93
<211> LENGTH: 6
<212> TYPE: PRT
```

```
<213> ORGANISM: Artificial Sequence
<220> FEATURE:
<223> OTHER INFORMATION: Synthetic peptide

<400> SEQUENCE: 93

Asp Gly Glu Thr Gly Glu
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic peptide

<400> SEQUENCE: 94

Phe Gln His Ile Trp Asp Phe Leu
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic peptide

<400> SEQUENCE: 95

Phe Glu His Leu Trp Ser Ser Leu
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic peptide

<400> SEQUENCE: 96

Phe Ser Asp Leu Trp Lys Leu Leu
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic peptide

<400> SEQUENCE: 97

Phe Glu Ala Gln Trp Ala Ala Leu
1               5

<210> SEQ ID NO 98
<211> LENGTH: 8
<212> TYPE: PRT
<213> ORGANISM: Artificial Sequence
<220> FEATURE:
<223> OTHER INFORMATION: Synthetic peptide

<400> SEQUENCE: 98

Phe Glu Ala Gln Trp Ala Ala Leu
1               5

<210> SEQ ID NO 99
<211> LENGTH: 7
<212> TYPE: PRT
<213> ORGANISM: Artificial Sequence
```

```
<220> FEATURE:
<223> OTHER INFORMATION: Synthetic peptide

<400> SEQUENCE: 99

Leu Leu Thr Pro Pro Gln Ser
1               5

<210> SEQ ID NO 100
<211> LENGTH: 6
<212> TYPE: PRT
<213> ORGANISM: Artificial Sequence
<220> FEATURE:
<223> OTHER INFORMATION: Synthetic peptide

<400> SEQUENCE: 100

Leu Thr Pro Pro Gln Ser
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic peptide

<400> SEQUENCE: 101

Pro Gly Glu Thr Pro Pro Leu Ser
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic peptide

<400> SEQUENCE: 102

Pro Gly Thr Pro Pro Ser Ser
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic peptide

<400> SEQUENCE: 103

Ser Val Glu Gln Thr Pro Lys Lys
1               5

<210> SEQ ID NO 104
<211> LENGTH: 6
<212> TYPE: PRT
<213> ORGANISM: Artificial Sequence
<220> FEATURE:
<223> OTHER INFORMATION: Synthetic peptide

<400> SEQUENCE: 104

Asp Ser Gly Leu Gly Ser
1               5

<210> SEQ ID NO 105
<211> LENGTH: 6
<212> TYPE: PRT
<213> ORGANISM: Artificial Sequence
<220> FEATURE:
```

```
<223> OTHER INFORMATION: Synthetic peptide

<400> SEQUENCE: 105

Asp Ser Gly Ile Glu Ser
1               5

<210> SEQ ID NO 106
<211> LENGTH: 6
<212> TYPE: PRT
<213> ORGANISM: Artificial Sequence
<220> FEATURE:
<223> OTHER INFORMATION: Synthetic peptide

<400> SEQUENCE: 106

Asp Ser Gly Ile His Ser
1               5

<210> SEQ ID NO 107
<211> LENGTH: 6
<212> TYPE: PRT
<213> ORGANISM: Artificial Sequence
<220> FEATURE:
<223> OTHER INFORMATION: Synthetic peptide

<400> SEQUENCE: 107

Asp Ser Gly Tyr Ser Ser
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic peptide

<400> SEQUENCE: 108

Ala Pro Thr Ala Val Val Leu Pro His
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic peptide

<400> SEQUENCE: 109

Lys Pro Thr Ala Tyr Val Arg Pro Met
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic peptide

<400> SEQUENCE: 110

Arg Pro Thr Ala Ala Val Thr Pro Ile
1               5

<210> SEQ ID NO 111
<211> LENGTH: 5
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: misc_feature
<222> LOCATION: (2)..(3)
<223> OTHER INFORMATION: Xaa can be any naturally occurring amino acid

<400> SEQUENCE: 111

Arg Xaa Xaa Leu Asp
1               5

<210> SEQ ID NO 112
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa denotes any amino acid residue

<400> SEQUENCE: 112

Arg Xaa Xaa Leu
1

<210> SEQ ID NO 113
<211> LENGTH: 6
<212> TYPE: PRT
<213> ORGANISM: Artificial Sequence
<220> FEATURE:
<223> OTHER INFORMATION: Synthetic peptide

<400> SEQUENCE: 113

Arg Pro Ala Leu Ser Asp
1               5

<210> SEQ ID NO 114
<211> LENGTH: 5
<212> TYPE: PRT
<213> ORGANISM: Artificial Sequence
<220> FEATURE:
<223> OTHER INFORMATION: Synthetic peptide

<400> SEQUENCE: 114

Arg Pro Ala Leu Ser
1               5

<210> SEQ ID NO 115
<211> LENGTH: 5
<212> TYPE: PRT
<213> ORGANISM: Artificial Sequence
<220> FEATURE:
<223> OTHER INFORMATION: Synthetic peptide

<400> SEQUENCE: 115

Arg Leu Ala Leu Asp
1               5

<210> SEQ ID NO 116
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa denotes any amino acid residue

<400> SEQUENCE: 116
```

```
-continued

Leu Xaa Xaa Lys
1

<210> SEQ ID NO 117
<211> LENGTH: 4
<212> TYPE: PRT
<213> ORGANISM: Artificial Sequence
<220> FEATURE:
<223> OTHER INFORMATION: Synthetic peptide

<400> SEQUENCE: 117

Leu Ala Ser Lys
1

<210> SEQ ID NO 118
<211> LENGTH: 5
<212> TYPE: PRT
<213> ORGANISM: Artificial Sequence
<220> FEATURE:
<223> OTHER INFORMATION: Synthetic peptide

<400> SEQUENCE: 118

Glu Glu Thr Ala Glu
1               5

<210> SEQ ID NO 119
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa denotes any amino acid residue

<400> SEQUENCE: 119

Cys Arg Tyr Xaa Pro Ser
1               5

<210> SEQ ID NO 120
<211> LENGTH: 6
<212> TYPE: PRT
<213> ORGANISM: Artificial Sequence
<220> FEATURE:
<223> OTHER INFORMATION: Synthetic peptide

<400> SEQUENCE: 120

Cys Arg Tyr Ile Pro Ser
1               5
```